United States Patent
Rana et al.

(10) Patent No.: US 6,420,591 B1
(45) Date of Patent: Jul. 16, 2002

(54) CARBAMATES AND COMPOSITIONS THEREOF, AND METHODS FOR THEIR USE FOR TREATING CANCER, INFLAMMATION, OR A VIRAL INFECTION

(75) Inventors: Tariq M Rana, Piscataway; Seongwoo Hwang, Somerset; Natarajan Tamilarasu, Highland Park, all of NJ (US)

(73) Assignee: University of Medicine and Dentistry of New Jersey, New Brunswick, NJ (US)

( * ) Notice: Subject to any disclaimer, the term of this patent is extended or adjusted under 35 U.S.C. 154(b) by 0 days.

(21) Appl. No.: 09/679,728

(22) Filed: Oct. 4, 2000

Related U.S. Application Data

(60) Provisional application No. 60/157,646, filed on Oct. 4, 1999.

(51) Int. Cl.[7] .............................................. C07C 261/00
(52) U.S. Cl. ............................ 560/24; 424/604; 514/18
(58) Field of Search ........................... 560/24; 424/604; 514/18

(56) References Cited

U.S. PATENT DOCUMENTS

| | | | |
|---|---|---|---|
| 5,627,210 A | * | 5/1997 | Valerio et al. |
| 5,843,995 A | | 12/1998 | Rana et al. |

OTHER PUBLICATIONS

Berkhout & Jeang (1989) Trans activation of human immunodeficiency virus type 1 is sequence specific for both the single–stranded bulge and loop of the trans–acting–responsive hairpin: a quantitative analysis. *J. Virol.* 63: 5501–5504.

Berkhout et al. (1989) Tat trans–activates the human immunodeficiency virus through a nascent RNA target. *Cell* 59:273–282.

Burgess et al. (1997) Solid phase syntheses of oligoureas. *J. Am. Chem. Soc.* 119:1556–1564.

Chastain & Tinoco (1991) Structural elements in RNA. *Progress in Nucleic Acid Res. & Mol. Biol.* 41: 131–177.

Cho et al., (1993) An unnatural biopolymer. *Science* 261:1303–1305.

Chow & Bogdan, (1997) A structural basis for RNA–ligand interactions. *Chemical Reviews* 97:1489–1514.

Dayton et al. (1986) The trans–activator gene of the human T cell lymphotropic virus type III is required for replication. *Cell* 44:941–947.

Dingwall et al. (1990) HIV–1 tat protein stimulates transcription by binding to a U–rich bulge in the stem of the TAR RNA structure. *EMBO J.* 9:4145–4153.

Emerman et al. (1987) The specificity of the human immunodeficiency virus type 2 transactivator is different from that of human immunodeficiency virus type 1. *EMBO J.* 6:3755–3760.

Feinberg et al. (1986) HTLV–III expression and production involve complex regulation at the levels of splicing and translation of viral RNA. *Cell* 46:807–817.

Fisher et al. (1986) The trans–activator gene of HTLV–III is essential for virus replication. *Nature* 320:367–371.

Garcia et al. (1989) Human immunodeficiency virus type 1 LTR TATA and TAR region sequences required for transcriptional regulation. *EMBO J.* 8:765–778.

(List continued on next page.)

*Primary Examiner*—Gary Geist
*Assistant Examiner*—Hector M Reyes
(74) *Attorney, Agent, or Firm*—Pennie & Edmonds LLP

(57) ABSTRACT

The present invention relates to novel carbamates and pharmaceutically acceptable salts thereof; compositions comprising the carbamate or a pharmaceutically acceptable salt thereof; and methods for treating cancer, inflammation, or a viral infection comprising administering to a patient in need of such treatment a therapeutically effective amount of the carbamate or pharmaceutically acceptable salt thereof.

15 Claims, 5 Drawing Sheets

OTHER PUBLICATIONS

Hauber et al. (1988) Mutational analysis of the human immunodeficiency virus type I long terminal repeat. J. Virol. 62:673–679.

Jakobovits et al. (1988) A discrete element 3' of human immunodeficiency virus 1 (HIV–1) and HIV–2 mRNA initiation sites mediates transcriptional activation by an HIV transactivator. Mol. Cell Biol. 8:2555–2561.

Kim et al. (1989) Temporal aspects of DNA and RNA synthesis during human immunodeficiency virus infection: evidence for differential gene expression. J. Virol. 63:3708–3713.

Knight et al. (1987) Expression of the art/trs protein of HIV and study of its role in viral envelope synthesis. Science 236:837–840.

Muesing et al. (1987) Regulation of Messenger RNA accumulation by a human immunodeficiency virus trans–activator protein. Cell 48:691–701.

Paikoff et al. (1996) The solid phase synthesis of N–alkyl-carbamate oligomers. Tetrahedron Letters 37:5653–5656.

Peterlin et al. (1986) Elevated levels of mRNA can account for the trans–activation of human immunodeficiency virus. Proc. Natl. Acad. Sci. U.S.A. 83:9734–9738.

Roy et al. (1990) Structural requirements for trans activation of human immunodeficiency virus type 1 long terminal repeat–directed gene expression by tat: importance of base pairing, loop sequence, and bulges in the tat–responsive sequence. J Virol. 64:1402–1406.

Selby et al. (1989) Structure, sequence, and position of the stem–loop in tar determine transcriptional elongation by tat through the HIV–1 long terminal repeat. Genes & Dev. 3:547–558.

Sodrowski et al. (1986) A second post–transcriptional trans–activator gene required for HTLV–III replication. Nature (London) 321:412–417.

Weeks & Crothers (1993) Major groove accessibility of RNA. Science 261:1574–1577.

Tamilarasu et al., "Highly Affinity and Specific Binding of HIV–1 TAR RNA by a Tat–Derived Oligourea," J. Am. Chem. Soc. 1999, vol. 121, No. 7, pp. 1597–1598.

* cited by examiner

CARBAMATES AND COMPOSITIONS THEREOF, AND METHODS FOR THEIR USE FOR TREATING CANCER, INFLAMMATION, OR A VIRAL INFECTION This application claims the benefit of U.S. Provisional Application No. 60/157,646, filed Oct. 4, 1999, which is incorporated herein by reference in its entirety.

This invention was made with government support under grant Nos. AI45466 and AI01369 awarded by the National Institute of Health. The government has certain rights in the invention.

1. FIELD OF THE INVENTION

The present invention relates to novel carbamates, ureas, and pharmaceutically acceptable salts thereof; compositions comprising the carbamate, urea, or a pharmaceutically acceptable salt thereof; and methods for treating or preventing cancer, inflammation, or a viral infection comprising administering to a patient in need of such treatment or prevention a therapeutically effective amount of the carbamate, urea, or pharmaceutically acceptable salt thereof.

2. BACKGROUND OF THE INVENTION

Protein-nucleic acid interactions are involved in many cellular functions, including transcription, RNA splicing, RNA maturation, telomere synthesis, and mRNA translation. Molecules that can bind with high affinity to specific sequences of single- or double-stranded nucleic acids have the potential to interfere with these interactions in a controllable way, making them attractive tools for molecular biology and medicine. Nucleic acids, and in particular RNA, however, can fold into complex tertiary structures consisting of local motif's such as loops, bulges, pseudoknots and turns (Chastain, M. & Tinoco, I., Jr. (1991) *Progress in Nucleic Acid Res.& Mol. Biol.* 41:131–177; Chow, C. S. & Bogdan, F. M. (1997) *Chemical Reviews* 97:1489–1514), which are critical for protein-RNA interactions (Weeks, K. M. & Crothers, D. M. (1993) *Science* 261:1574–1577). The dependence of these interactions on the native three-dimensional structure of RNA makes it difficult to design synthetic agents with general, simple-to-use recognition rules analogous to those for the formation of double- and triple-helical nucleic acids. Transcription of the HIV genome during virus replication shows distinct kinetic phases (see e.g., Feinberg et al. (1986) *Cell* 46:807–817; Kim et al. (1989) *J. Virol.* 63:3708–3713; Knight et al. (1987) *Science* 236:837–840; Sodrowski et al. (1986) *Nature* (London) 321:412–417). The initial products of HIV gene expression are short, multiply spliced mRNAs approximately 1.8 to 2.0 kb in length, which encode the trans-acting regulatory proteins TAT, REV, and possibly NEF. As infection by the virus develops, and the levels of the TAT and REV proteins rise in the infected cells, mRNA production shifts progressively towards production of a family of singly-spliced 4.3 kb mRNAs encoding ENV and other HIV gene products such as VIF and VPR. To achieve this control of gene expression, the HIV virus relies on the interaction of cellular and virus-encoded trans-acting factors with cis-acting viral regulatory sequences (Dayton et al. (1986) *Cell* 44:941–947; Fisher et al. (1986) *Nature* 320:367–371; Feinberg et al. (1986) *Cell* 46:807–817). Initiation of transcription relies largely on the presence of binding sites for cellular transcription factors in the viral long terminal repeat (LTR) (Garcia et al. (1989) *EMBO J.* 8:765–778). The virally encoded regulatory proteins TAT and REV exert their activity via cis-acting sequences encoded within HIV messenger RNAs. The trans activation-responsive region (TAR) is required for TAT activity, and is located in the viral long terminal repeat (LTR) between residues +1 and +79 (Muesing et al. (1987) *Cell* 48:691–701; Emerman et al. (1987) *EMBO J.* 6:3755-3760; Roy et al. (1 990) *J Virol.* 64:1402–1406 (1990); Berkhout et al. (1989)*J. Virol.* 63:5501–5504).

The distinct kinetic phases of HIV transcription are now believed to reflect the intracellular levels of the regulatory proteins TAT and REV. As TAT levels rise, increased transcription from the LTR is stimulated by the trans-activation mechanism. This leads to further increases in TAT levels, and also stimulates production of REV. Production of the viral structural proteins begins once REV levels have risen to sufficiently high levels to promote export of messenger RNAs carrying the rev-responsive element (RRE)sequence. Significant levels of HIV gene expression are only achieved in the presence of TAT protein. Experiments strongly suggest that TAT activity requires RNA target sequences. Deletion analysis of the viral LTR showed that TAT activity requires a regulatory element located downstream of the initiation site for transcription, at the 5-terminus of all the mRNA transcripts between residues +1 and +79, called the trans-activation-response region (TAR) (Muesing et al. (1987) *Cell* 48:691–701; Emerman et al. (1987) *EMBO J.* 6:3755–3760; Roy et al. (1990) *J Virol.* 64:1402–1406 (1990); Berkhout et al. (1989) *J. Virol.* 63:5501–5504). The placement of TAR in a transcribed region suggested that it could function as an RNA rather than as a DNA element. (Muesing et al. (1987) *Cell* 48:691–701; Emerman et al. (1987) *EMBO J.* 6:3755–3760; Selby et al. (1989) *Genes Dev.* 3:547–558; Hauber et al. (1988) *J. Virol.* 62:673–679; Jakobovits et al. (1988) *J. Mol. Cell Biol.* 8:2555–2561; Peterlin et al. (1986) *Proc. Natl. Acad. Sci. U.S.A.* 83:9734–9738).

Furthermore, the TAR RNA sequence forms a highly stable, nuclease-resistant, stem-loop structure (Selby et al. (1989) *Genes & Dev.* 3:547–558). It appears that the TAR RNA sequence must be transcribed in the nucleus and correctly folded in order for trans-activation to occur (Berkhout (1989) *Cell* 59:273–282).

And it has been demonstrated that TAT is able to specifically recognize TAR RNA. Binding shows high affinity (Kd=12 nM) and TAT forms one-to-one complexes with TAR RNA (Dingwall et al. (1990) *EMBO J.* 9:4145–4153). This provides strong evidence for the ability of TAT to stimulate transcription from promoters that carry the TAR sequence by direct binding to TAR RNA. Compounds that bind TAR RNA inhibit the activity of the regulatory protein TAT in the viral growth cycle of HIV and, accordingly, are useful for treating or preventing HIV infection.

Moreover, compounds that bind to specific sequences and/or structures in nucleic acids and thereby modulate or interfere with protein-nucleic acids, and in particular, protein-RNA interactions, are potentially valuable therapeutic agents useful for the prevention and treatment of cancer, and inflammatory conditions, as well as disease arising from viral infection, including HIV infection and AIDS.

Therefore, there is a clear need in the art for compounds that bind RNA and interfere with protein-RNA interactions, and in particular, there is a clear need in the art for compounds that bind TAR RNA.

Citation or identification of any reference in Section 2 of this application is not an admission that such reference is available as prior art to the present invention.

3. SUMMARY OF THE INVENTION

The present invention provides compounds of formula I:

I and pharmaceutically acceptable salts thereof, wherein each Y is independently a radical having the structure of II, III, or IV:

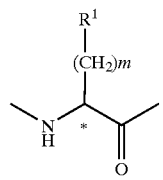

II

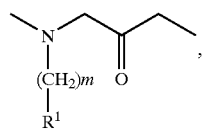

III or

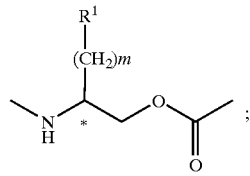

IV each $R_1$ is independently selected from the group consisting of —$NH_2$, —$NHC(=NH)NH_2$, and —$CH_2C(=NH)NH_2$;

each m is independently an integer ranging from 3 to 7;

each * is an (R) or (S) chiral center; and with the proviso that at least one Y is a radical having the structure of IV.

In one embodiment, the compounds of formula I and pharmaceutically acceptable salts thereof are those wherein at least two Y are independently a radical having the structure of IV.

In another embodiment, the compounds of formula I and pharmaceutically acceptable salts thereof are those wherein each Y is independently a radical having the structure of IV.

The compounds of formula I and pharmaceutically acceptable salts thereof are useful for treating or preventing cancer, inflammation, or a viral infection in a patient.

The present invention further provides compositions comprising a therapeutically effective amount of a compound of formula I or a pharmaceutically acceptable salt thereof. The compositions comprising a compound of formula I or a pharmaceutically acceptable salt thereof can additionally comprise a pharmaceutically acceptable vehicle. These compositions are useful for treating or preventing cancer, inflammation, or a viral infection in a patient.

The present invention still further provides a method for treating or preventing cancer, inflammation, or a viral infection in a patient, comprising administering to a patient in need of such treatment or prevention a therapeutically effective amount of a compound of formula I or a pharmaceutically acceptable salt thereof.

The present invention still further provides compounds of formula V:

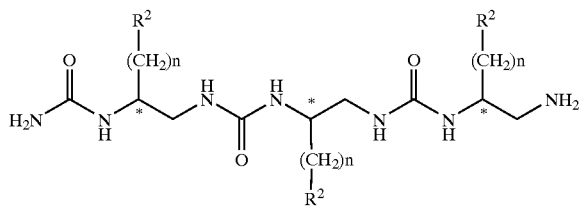

V and pharmaceutically acceptable salts thereof, wherein each $R^2$ is independently selected from the group consisting of —$NH_2$, —$NHC(=NH)NH_2$, —$CH_2C(=NH)NH_2$, and —$C(O)NH_2$;

each n is independently an integer ranging from 3 to 7; and each * is an (R) or (S) chiral center.

The compounds of formula V and pharmaceutically acceptable salts thereof are useful for treating or preventing cancer, inflammation, or a viral infection in a patient.

The present invention still further provides compositions comprising a therapeutically effective amount of a compound of formula V or a pharmaceutically acceptable salt thereof. The compositions comprising a compound of formula V or a pharmaceutically acceptable salt thereof can additionally comprise a pharmaceutically acceptable vehicle. These compositions are useful for treating or preventing cancer, inflammation, or a viral infection in a patient.

The present invention still further provides a method for treating or preventing cancer, inflammation, or a viral infection in a patient, comprising administering to a patient in need of such treatment or prevention a therapeutically effective amount of a compound of formula V or a pharmaceutically acceptable salt thereof.

The present invention may be understood more fully by reference to the figures, detailed description, and examples, which are intended to exemplify non-limiting embodiments of the invention.

4. BRIEF DESCRIPTION OF THE FIGURES

5. DETAILED DESCRIPTION OF THE INVENTION

5.1 DEFINITIONS AND ABBREVIATIONS

Figure 1:
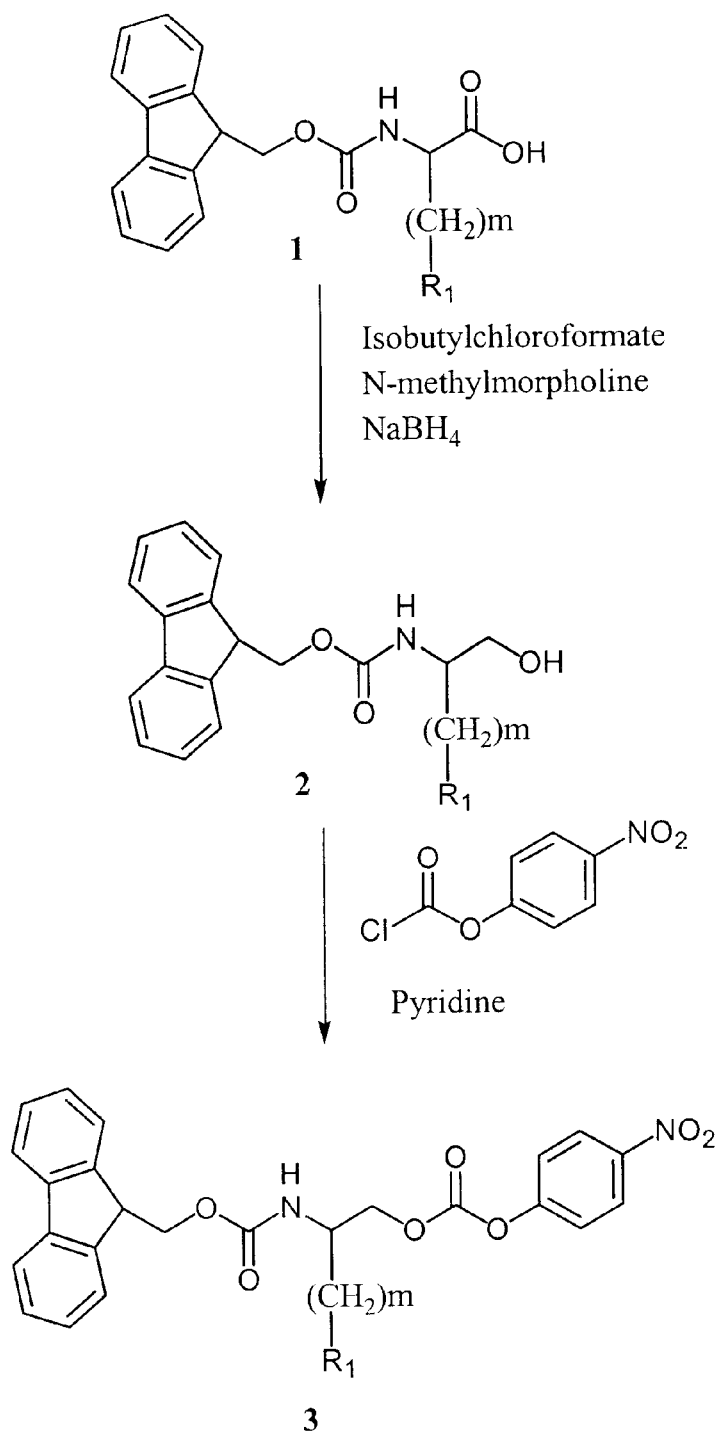
FIG. 1 is a schematic depiction of a synthesis of a carbamate monomer useful for installing the radical having the structure IV in the compounds of formula I. $R_1$ is —$NH_2$, —$NHC(=NH)NH_2$, or —$CH_2C(=NH)NH_2$. m is an integer ranging from 3 to 7.

"HMBA" is 4-(2',4'-dimethoxyphenyl-Fmoc aminomethyl)phenoxyacetamido-norleucyl-methylbenzhydrylamine resin.

"Mtr" is a (4-methoxy-2,3,6-trimethylphenyl)sulfonyl group.

"tBOC" and "BOC" are t-butoxycarbonyl groups.

"Fmoc" is a 9-fluorenylmethoxycarbonyl protecting group.

"Teoc-ONP" is 2-(trimethylsilyl)ethyl-4-nitrophenyl carbonate.
"MsCl" is methanesulfonyl chloride.
"TEA" is triethylamine.
"DIPEA" is diisopropylethylamine.
"TIPS" is trisisopropylsilane.
"TFA" is trifluoroacetic acid.
"THF" is tetrahydrofuran.
"TBAF" is tetrabutylammonium fluoride.
"HOBT" is 1-hydroxybenzotriazole.
"DIPDCI" is 1,3-diisopropyldicarboimide.
"NMP" is N-methylpyrrolidinone.
"DMF" is N,N-dimethylformamide.

As used herein, the term "compounds of the invention" means, collectively, the compounds of formula I, formula V, pharmaceutically acceptable salts thereof.

The compounds of the invention are identified herein by their chemical structure and/or chemical name. Where a compound is referred to by both a chemical structure and a chemical name, and that chemical structure and chemical name conflict, the chemical structure is determinative of the compound's identity.

The compounds of the invention contain one or more chiral centers, depicted by an asterisk (*) in formula I and formula V and by a bold or dashed line in compounds specific to formula I or formula V. Therefore, the compounds of the invention exist as enantiomers or diastereomers. According to the invention, formula I and formula V encompass all of the corresponding compounds' enantiomers, i.e., each (+)- and (−)-enantiomer, and diastereomers, i.e., each chiral center's (R) and (S) isomer. (R) and (S) assignments are made according to well-known sequence-rule procedures for determining (R) and (S) priority (see, for example, *IUPAC Nomenclature of Organic Chemistry*, Section E (1979); R. S. Cahn et al., *Angew. Chem.* 78:413–447 (1966); and V. Prelog et al., *Angew. Chem., Int. Ed.*, 21:567–583 (1982)).

In the compounds of formula I, and pharmaceutically acceptable salts thereof, each radical having the structure of II, III, or IV binds as written from left to right to H—, II, III, IV, or —NH$_2$, as the case may be.

As used herein, the term "patient" means an animal, including, but not limited, to an animal such a cow, monkey, horse, sheep, pig, chicken, turkey, quail, cat, dog, mouse, rat, rabbit, and guinea pig, and is more preferably a mammal, and most preferably a human.

When administered to a patient, e.g., an animal for veterinary use or for improvement of livestock, or to a human for clinical use, the compounds of the invention are administered in isolated form. As used herein, "isolated" means that the compounds of the invention are separated from other components of either (a) a natural source, such as a plant or cell, preferably bacterial culture, or (b) a synthetic organic chemical reaction mixture. Preferably, via conventional techniques, the compounds of the invention are purified. As used herein, "purified" means that when isolated, the isolate contains at least 95%, preferably at least 98%, by weight, of a particular enantiomer, racemate, or diastereomer of a compound of formula I or formula V.

As used herein, the phrase "pharmaceutically acceptable salt(s)," means salt(s) formed from an acid and a primary, secondary, or tertiary amino group of a compound of formula I or formula V. Preferred salts include, but not limited, to sulfate, citrate, acetate, oxalate, chloride, bromide, iodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylenebis-(2-hydroxy-3-naphthoate)) salts.

5.2 SYNTHESIS OF THE COMPOUNDS OF THE INVENTION

The compounds of the invention can be obtained via conventional organic synthesis, preferably on a solid support. Generally, in a process well known to those of ordinary skill in the art, activated monomers are introduced to and bound by reactive moieties on the solid support, or to linker molecules attached to the support.

After introduction, the first monomer is completely coupled to substantially all the sites of the solid support. Complete coupling means that the coupling reaction is driven to completion irrespective of the differences in the coupling rates of individual monomeric units to be attached. In addition, the monomers are coupled to substantially all available coupling sites on the solid support so that each solid support will contain essentially only one molecular species.

The coupling of the monomers to the support may be accomplished by techniques familiar to those in the art and as provided below as well as, for example, in Stewart and Young, 1984, Solid Phase Synthesis, Second Edition, Pierce Chemical Co., Rockford, Ill. As would be known to those of ordinary skill in the art, the process of synthesis on solid supports generally involves building an oligomeric or polymeric compound, proceeding from one defined and activated end. After attachment of the first monomeric unit to the solid support, the protecting group(s) are then cleaved off, and the next monomer, also protected, is coupled to the first monomer attached to the solid support. The cycle of deprotection and coupling is repeated until the oligomeric compound is completed. Any reactive side chains are protected by chemical groups that can withstand the coupling and deprotection procedure but can be removed at the end of the synthesis.

In order to couple each monomeric unit to the growing synthetic chain, one reactive moiety of the protected monomer must be activated. Many methods of activation may be used in the practice of the invention and include, for example, preformed symmetrical anhydrides (PSA), preformed mixed anhydride (PMA), acid chlorides, active esters, and in situ activation, as set forth in Fields and Noble, 1990, "Solid phase peptide synthesis utilizing 9-fluorenylmethoxycarbonyl amino acids", Int. J. Pept. Protein Res. 35:161–214.

The use of Fmoc amino acids is but one strategy of peptide synthesis. A Boc (t-butyloxycarbonyl-protected amino group) strategy may also be used to prepare a library of peptides bound to the solid support (e.g., Geysen et al., 1987, J. Immunol. Methods 102:259–274).

5.2.1 THE COMPOUNDS OF FORMULA I

The compounds of formula I and pharmaceutically acceptable salts thereof are carbamates and can be obtained via conventional methods (see, for example, S. J. Paikoff et al., *Tetrahedron Lett.* 37(32):5653–5656 (1996) and C. Y. Cho et al., *Science* 261:1303–1305 (1993)).

The radical having the structure IV can be installed in the compounds of formula I using a carbamate monomer 3 (FIG. 1). The carbamate monomers preferably have an Fmoc protecting group. The carbamate monomers are those wherein R$_1$ is —NH$_2$, —NHC(=NH)NH$_2$, or —CH$_2$C(=NH)NH$_2$; and m is an integer ranging from 3 to 7. Carbamate monomers 3 can be obtained from N$^\alpha$-Fmoc-protected amino acids 1. N$^\alpha$-Fmoc-protected amino acids are available commercially, for example, from Aldrich Chemical Co. Milwaukee, Wis. or by using known synthetic methods, for example, by those described in Carpino et al., *J. Org. Chem.* 37:3404 (1972). N$^\alpha$-Fmoc-protected amino acids 1 can be reduced to their corresponding amino alcohols 2 using, for example, N-methyl morpholine and isobutyl chloroformate, followed by treatment with NaBH$_4$. Amino alcohols 2 are then activated using 4-nitrophenylchloroformate to provide carbamate monomers 3, which can be purified using conventional silica gel chromatography.

Preferred compounds of formula I are:

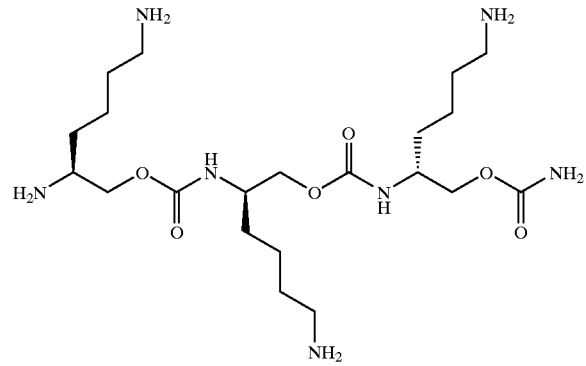

Carbamic acid 6-amino-2-[6-amino-2-(2,6-diamino-hexyloxycarbonylamino)-hexyloxycarbonylamino]-hexyl ester (Compound AA);

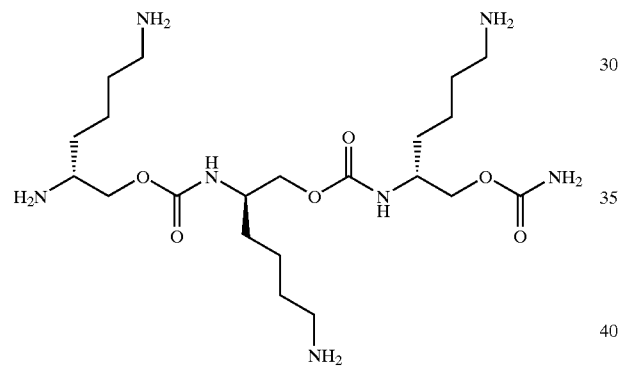

Carbamic acid 6-amino-2-[6-amino-2-(2,6-diamino-hexyloxycarbonylamino)-hexyloxycarbonylamino]-hexyl ester (Compound AB);

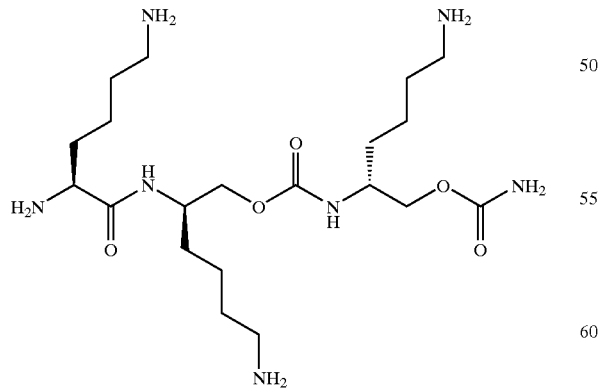

Carbamic acid 6-amino-2-[6-amino-2-(2,6-diamino-hexanoylamino)-hexyloxycarbonylamino]-hexyl ester (Compound AC);

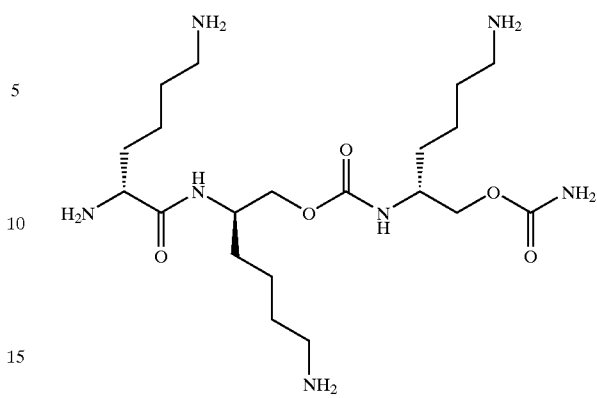

Carbamic acid 6-amino-2-[6-amino-2-(2,6-diamino-hexanoylamino)-hexyloxycarbonylamino]-hexyl ester (Compound AD);

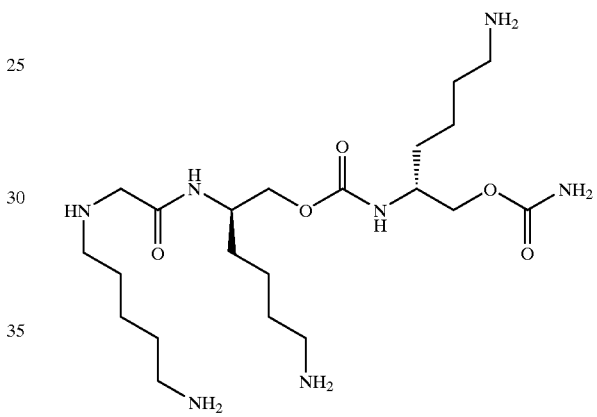

Carbamic acid 6-amino-2-{6-amino-2-[2-(5-amino-pentylamino)-acetylamino]-hexyloxycarbonylamino)-hexyl ester (Compound AE);

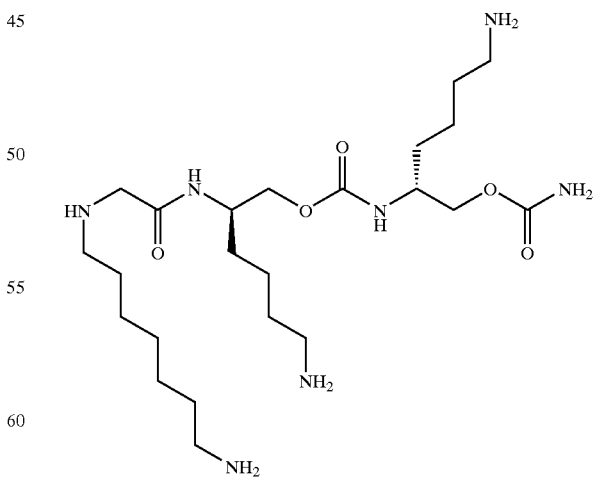

Carbamic acid 6-amino-2-{6-amino-2-[2-(7-amino-heptylamino)-acetylamino]-hexyloxycarbonylamino}-hexyl ester (Compound AF);

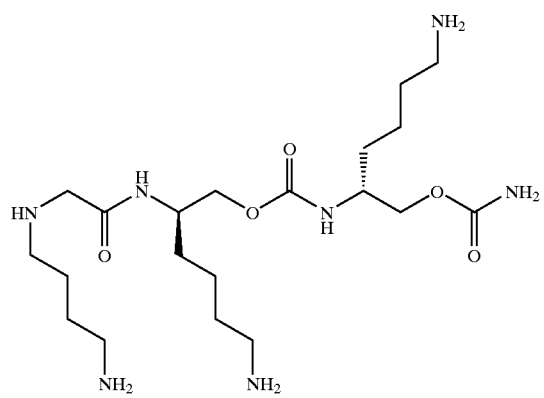

Carbamic acid 6-amino-2-{6-amino-2-[2-(4-amino-butylamino)-acetylamino]-hexyloxycarbonylamino}-hexyl ester (Compound AG);

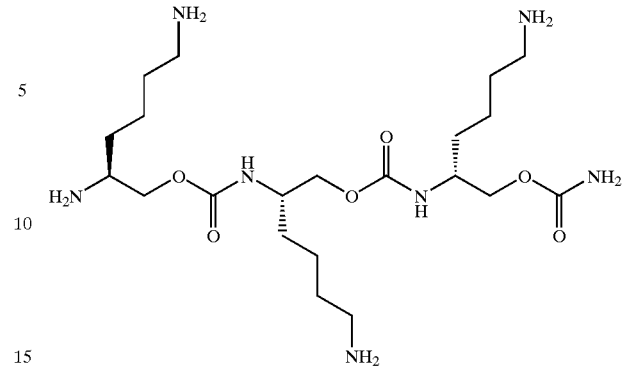

Carbamic acid 6-amino-2-[6-amino-2-(2,6-diamino-hexyloxycarbonylamino)-hexyloxycarbonylamino]-hexyl ester (Compound AJ);

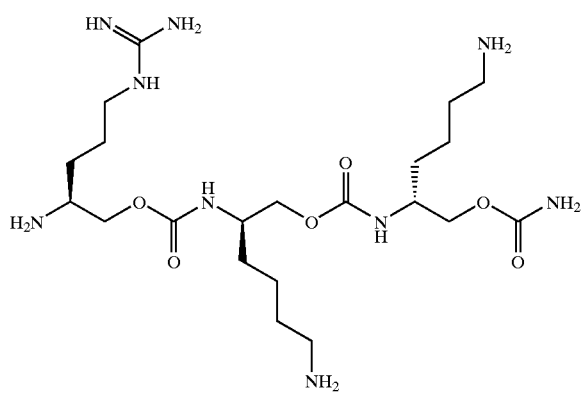

Carbamic acid 6-amino-2-[6-amino-2-(2-amino-5-guanidino-pentyloxycarbonylamino)-hexyloxycarbonylamino]-hexyl ester (Compound AH);

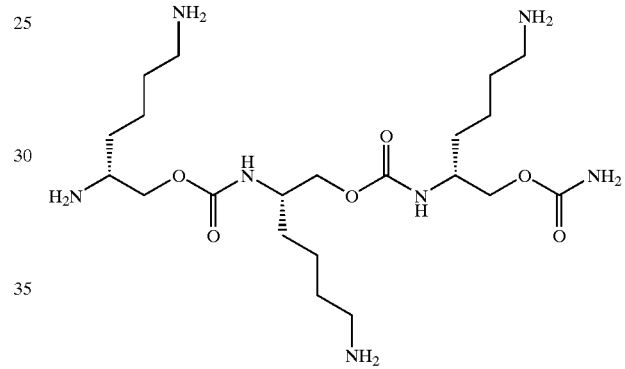

Carbamic acid 6-amino-2-[6-amino-2-(2,6-diamino-hexyloxycarbonylamino)-hexyloxycarbonylamino]-hexyl ester (Compound AK);

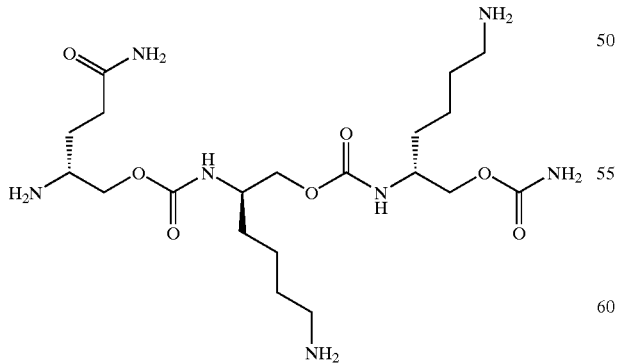

Carbamic acid 6-amino-2-[6-amino-2-(2-amino-4-carbamoyl-butoxycarbonylamino)-hexyloxycarbonylamino]-hexyl ester (Compound AI);

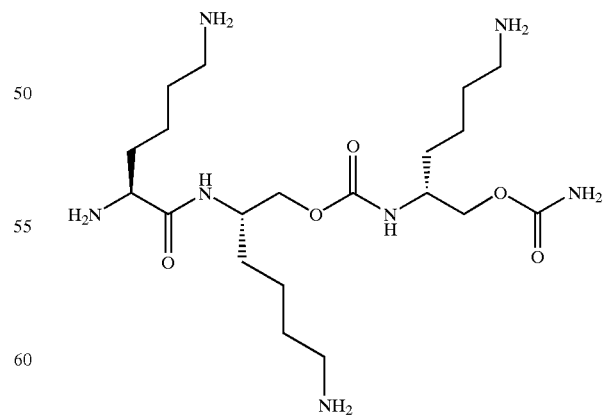

Carbamic acid 6-amino-2-[6-amino-2-(2,6-diamino-hexanoylamino)-hexyloxycarbonylamino]-hexyl ester (Compound AL);

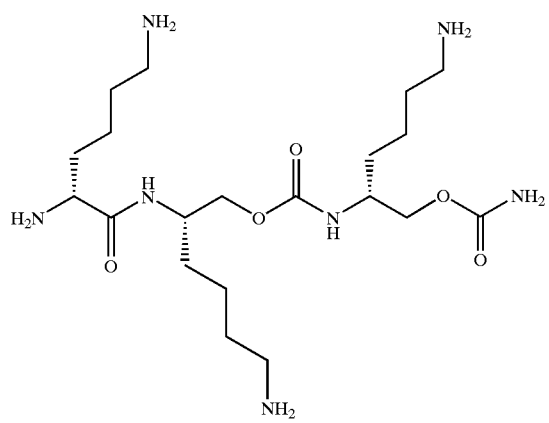

Carbamic acid 6-amino-2-[6-amino-2-(2,6-diamino-hexanoylamino)-hexyloxycarbonylamino]-hexyl ester (Compound AM);

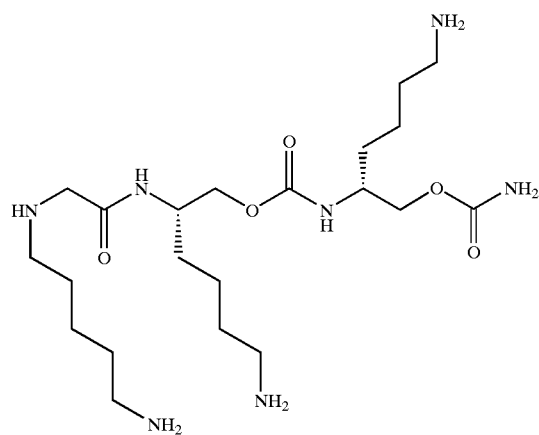

Carbamic acid 6-amino-2-{6-amino-2-[2-(5-amino-pentylamino)-acetylamino]-hexyloxycarbonylamino}-hexyl ester (Compound AN);

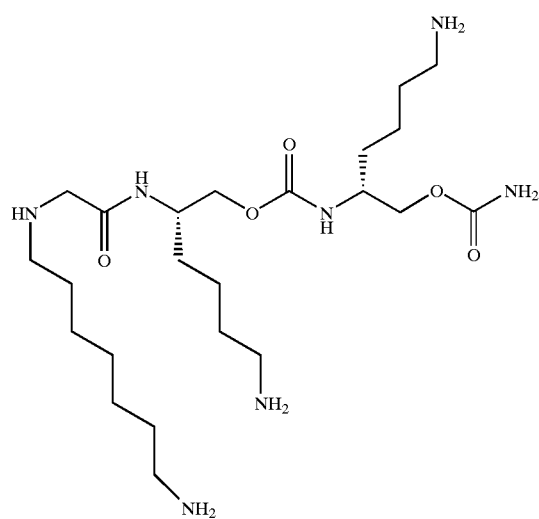

Carbamic acid 6-amino-2-{6-amino-2-[2-(7-amino-heptylamino)-acetylamino]-hexyloxycarbonylamino}-hexyl ester (Compound AO);

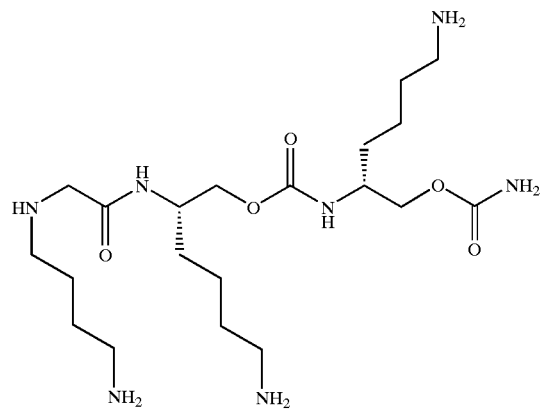

Carbamic acid 6-amino-2-{6-amino-2-[2-(4-amino-butylamino)-acetylamino]-hexyloxycarbonylamino}-hexyl ester (Compound AP);

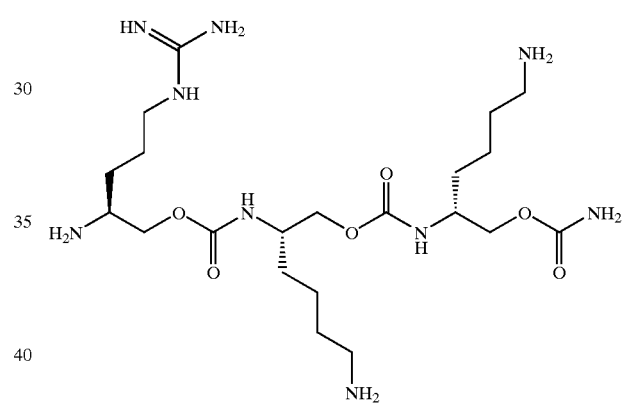

Carbamic acid 6-amino-2-[6-amino-2-(2-amino-5-guanidino-pentyloxycarbonylamino)-hexyloxycarbonylamino]-hexyl ester (Compound AQ);

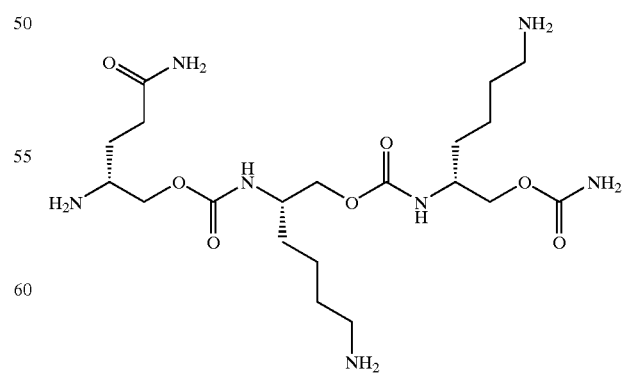

Carbamic acid 6-amino-2-[6-amino-2-(2-amino-4-carbamoyl-butoxycarbonylamino)-hexyloxycarbonylamino]-hexyl ester (Compound AR);

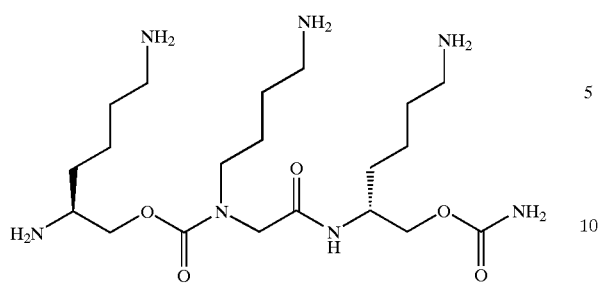

Carbamic acid 6-amino-2-{2-[(4-amino-butyl)-(2,6-diamino-hexyloxycarbonyl)-amino]-acetylamino}-hexyl ester (Compound AS);

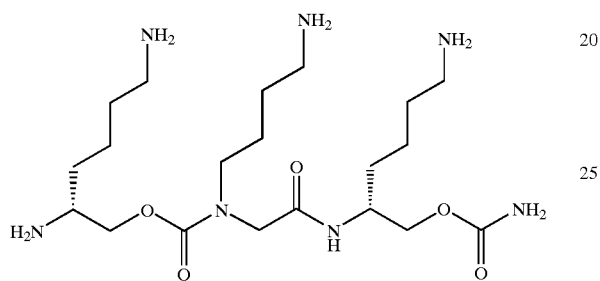

Carbamic acid 6-amino-2-{2-[(4-amino-butyl)-(2,6-diamino-hexyloxycarbonyl)-amino]-acetylamino}-hexyl ester (Compound AT);

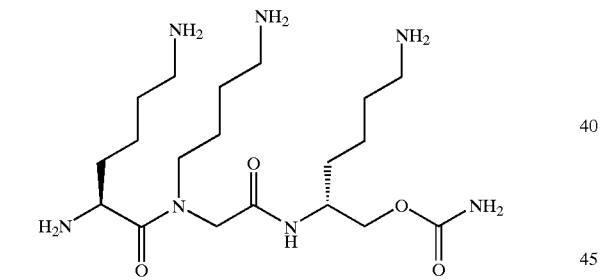

Carbamic acid 6-amino-2-{2-[(4-amino-butyl)-(2,6-diamino-hexanoyl)-amino]-acetylamino}-hexyl ester (Compound AU);

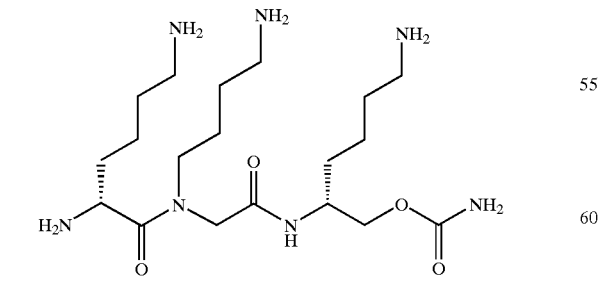

Carbamic acid 6-amino-2-{2-[(4-amino-butyl)-(2,6-diamino-hexanoyl)-amino]-acetylamino}-hexyl ester (Compound AV);

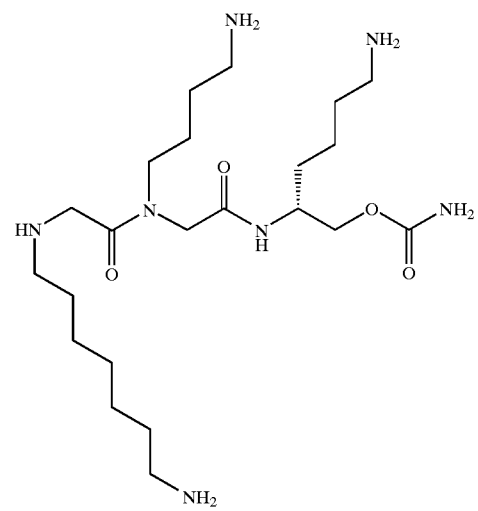

Carbamic acid 6-amino-2-(2-{(4-amino-butyl)-[2-(4-amino-butylamino)-acetyl]-amino}-acetylamino)-hexyl ester (Compound AW);

Carbamic acid 6-amino-2-(2-{(4-amino-butyl)-[2-(7-amino-heptylamino)-acetyl]-amino}-acetylamino)-hexyl ester (Compound AX);

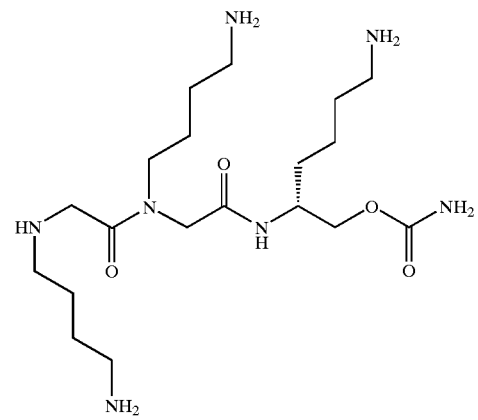

Carbamic acid 6-amino-2-(2-{(4-amino-butyl)-[2-(4-amino-butylamino)-acetyl]-amino}-acetylamino)-hexyl ester (Compound AY);

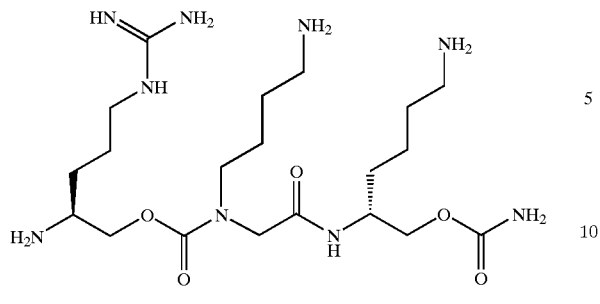

Carbamic acid 6-amino-2-{2-[(4-amino-butyl)-(2-amino-5-guanidino-pentyloxycarbonyl)-amino]-acetylamino}-hexyl ester (Compound AZ);

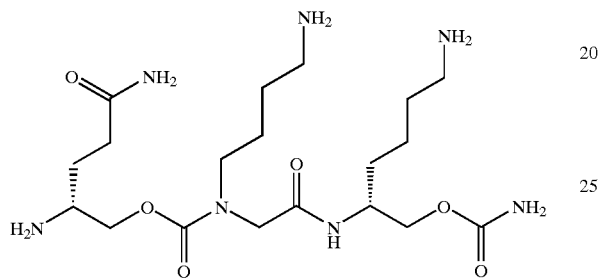

Carbamic acid 6-amino-2-{2-[(4-amino-butyl)-(2-amino-4-carbamoyl-butoxycarbonyl)-amino]-acetylamino}-hexyl ester (Compound BA);

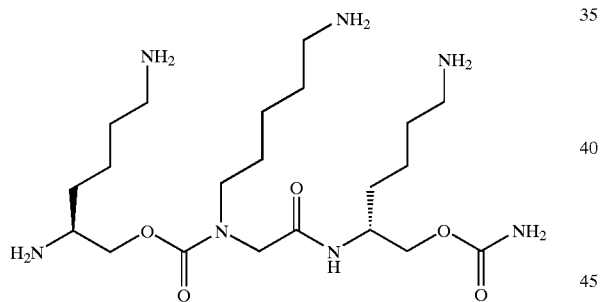

Carbamic acid 6-amino-2-{2-[(5-amino-pentyl)-(2,6-diamino-hexyloxycarbonyl)-amino]-acetylamino}-hexyl ester (Compound BB);

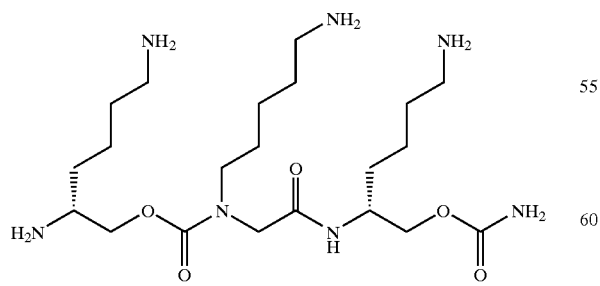

Carbamic acid 6-amino-2-{2-[(5-amino-pentyl)-(2,6-diamino-hexyloxycarbonyl)-amino]-acetylamino}-hexyl ester (Compound BC);

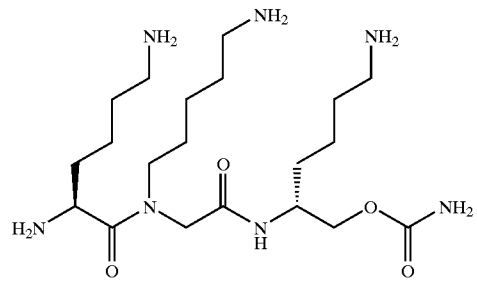

Carbamic acid 6-amino-2-{2-[(5-amino-pentyl)-(2,6-diamino-hexanoyl)-amino]-acetylamino}-hexyl ester (Compound BD);

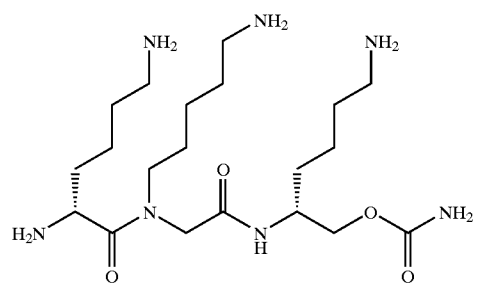

Carbamic acid 6-amino-2-12-[(5-amino-pentyl)-(2,6-diamino-hexanoyl)-amino]-acetylamino}-hexyl ester (Compound BE);

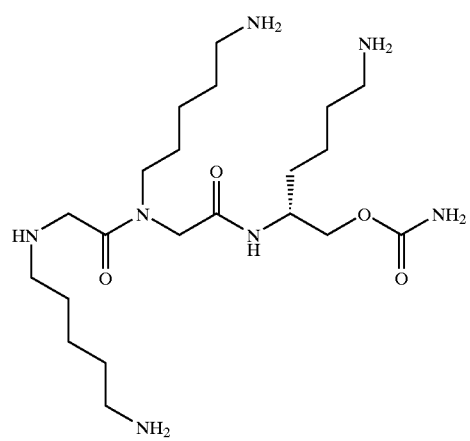

Carbamic acid 6-amino-2-(2-{(5-amino-pentyl)-[2-(5-amino-pentylamino)-acetyl]-amino}-acetylamino)-hexyl ester (Compound BF);

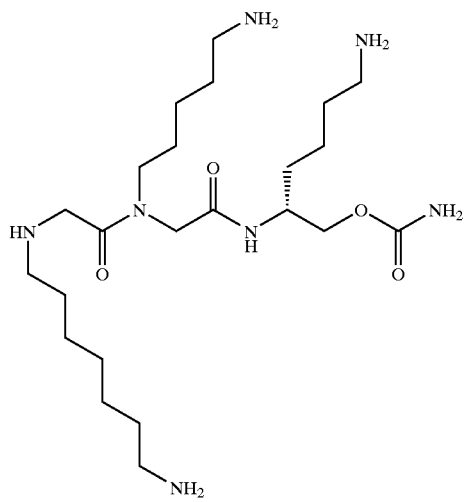

Carbamic acid 6-amino-2-{2-[[2-(7-amino-heptylamino)-acetyl]-(5-amino-pentyl)-amino]-acetylamino}-hexyl ester (Compound BG);

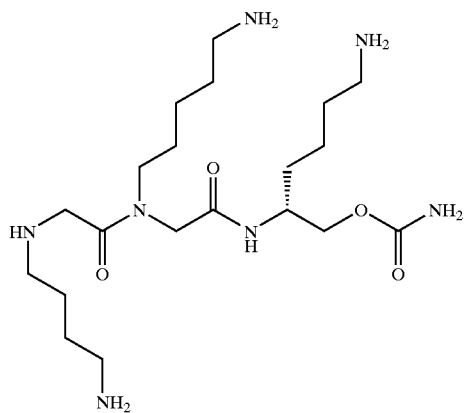

Carbamic acid 6-amino-2-{2-[[2-(4-amino-butylamino)-acetyl]-(5-amino-pentyl)-amino]-acetylamino}-hexyl ester (Compound BH);

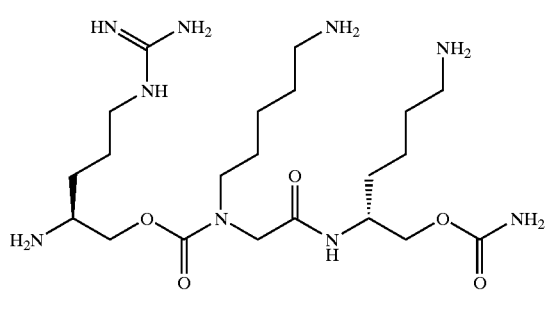

Carbamic acid 6-amino-2-{2-[(2-amino-5-guanidino-pentyloxycarbonyl)-(5-amino-pentyl)-amino]-acetylamino}-hexyl ester (Compound BI);

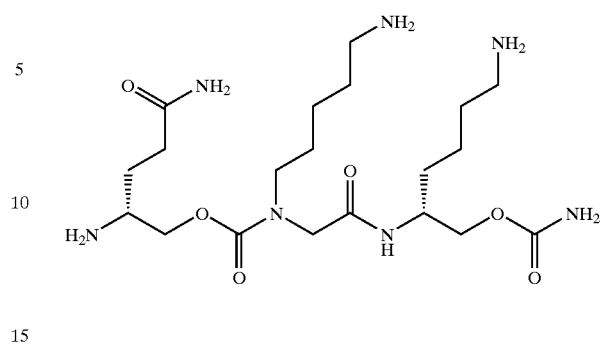

Carbamic acid 6-amino-2-{2-[(2-amino-4-carbamoyl-butoxycarbonyl)-(5-amino-pentyl)-amino]-acetylamino}-hexyl ester (Compound BJ);

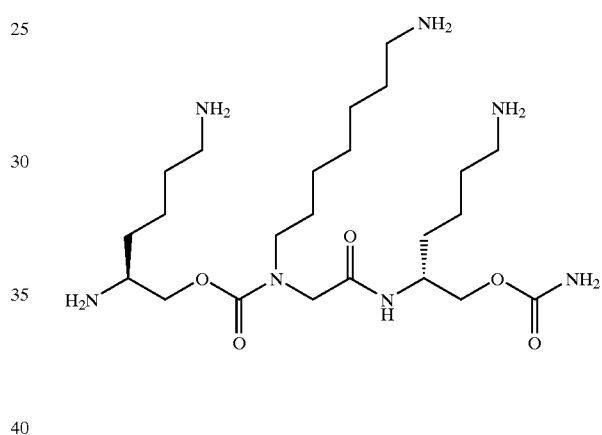

Carbamic acid 6-amino-2-{2-[(7-amino-heptyl)-(2,6-diamino-hexyloxycarbonyl)amino]-acetylamino}-hexyl ester (Compound BK);

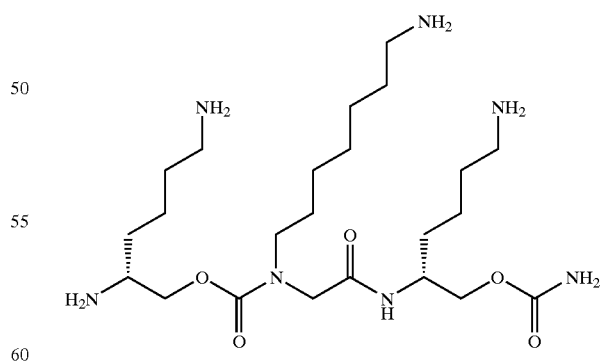

Carbamic acid 6-amino-2-{2-[(7-amino-heptyl)-(2,6-diamino-hexyloxycarbonyl)-amino]-acetylamino}-hexyl ester (Compound BL);

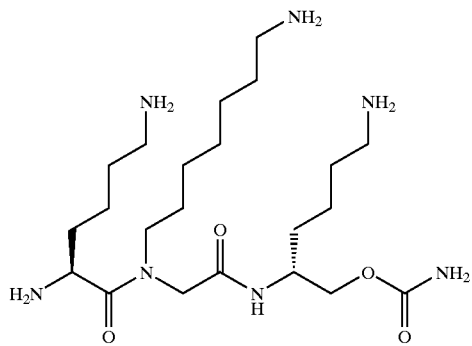

Carbamic acid 6-amino-2-{2-[(7-amino-heptyl)-(2,6-diamino-hexanoyl)-amino]-acetylamino)-hexyl ester (Compound BM);

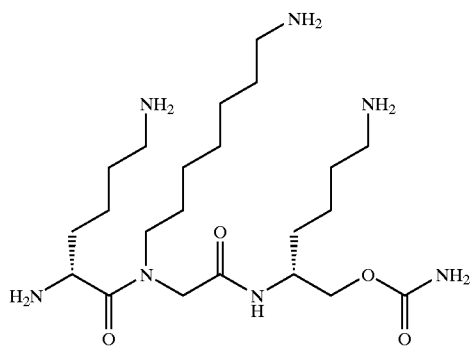

Carbamic acid 6-amino-2-{2-[(7-amino-heptyl)-(2,6-diamino-hexanoyl)-amino]-acetylamino}-hexyl ester (Compound BN);

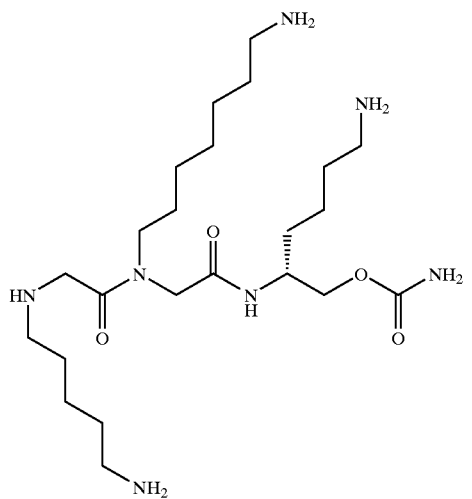

Carbamic acid 6-amino-2-(2-{(7-amino-heptyl)-[2-(5-amino-pentylamino)-acetyl]-amino}-acetylamino)-hexyl ester (Compound BO);

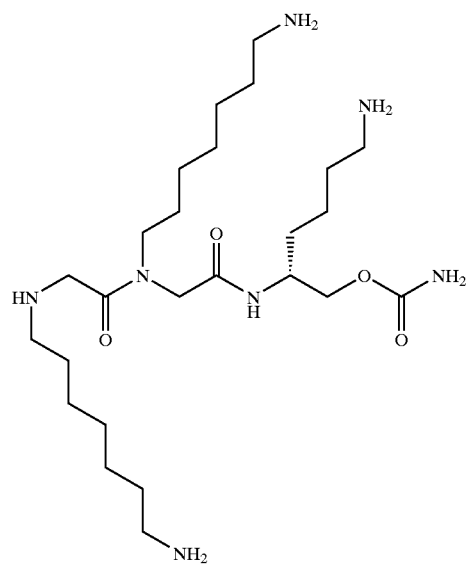

Carbamic acid 6-amino-2-(2-{(7-amino-heptyl)-[2-(7-amino-heptylamino)-acetyl]-amino}-acetylamino)-hexyl ester (Compound BP);

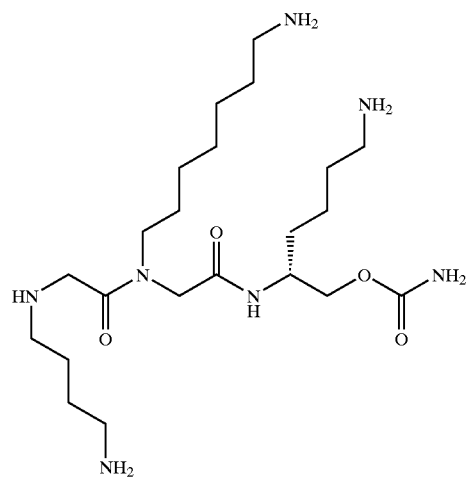

Carbamic acid 6-amino-2-{2-[[2-(4-amino-butylamino)-acetyl]-(7-amino-heptyl)-amino]-acetylamino}-hexyl ester (Compound BQ);

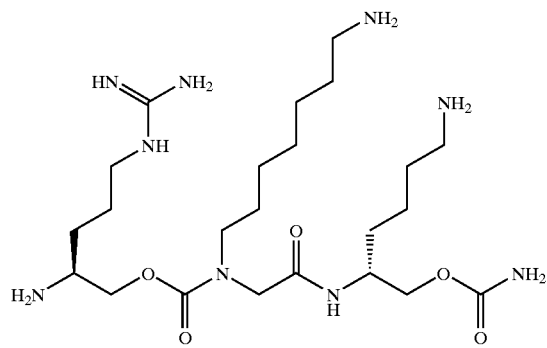

Carbamic acid 6-amino-2-{2-[(2-amino-5-guanidino-pentyloxycarbonyl)-(7-amino-heptyl)-amino]-acetylamino}-hexyl ester (Compound BR);

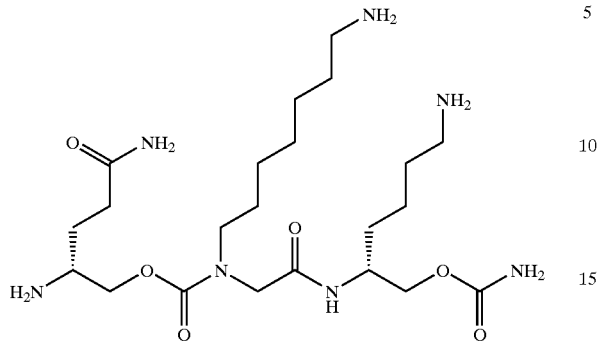

Carbamic acid 6-amino-2-{2-[(2-amino-4-carbamoyl-butoxycarbonyl)-(7-amino-heptyl)-amino]-acetylamino}-hexyl ester (Compound BS);

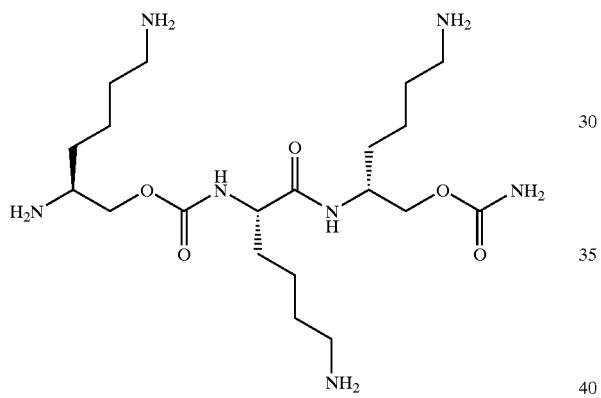

Carbamic acid 6-amino-2-[6-amino-2-(2,6-diamino-hexyloxycarbonylamino)-hexanoylamino]-hexyl ester (Compound BT);

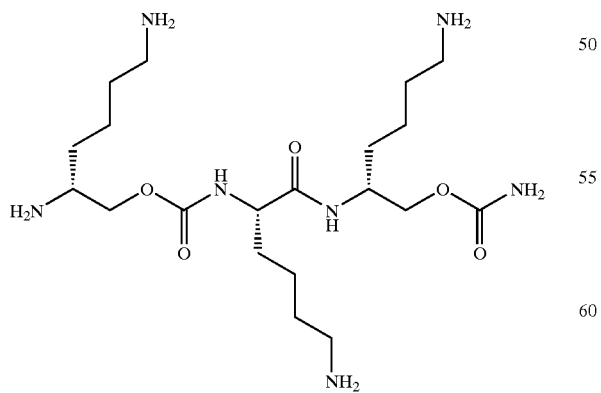

Carbamic acid 6-amino-2-[6-amino-2-(2,6-diamino-hexyloxycarbonylamino)-hexanoylamino]-hexyl ester (Compound BU);

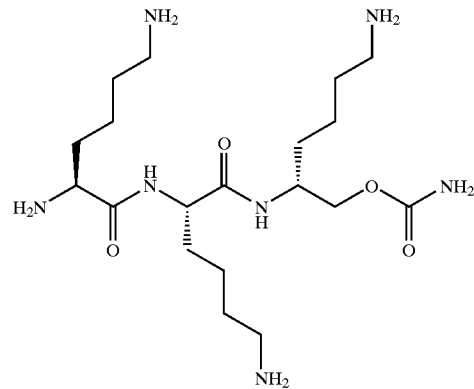

Carbamic acid 6-amino-2-[6-amino-2-(2,6-diamino-hexanoylamino)-hexanoylamino]-hexyl ester (Compound BV);

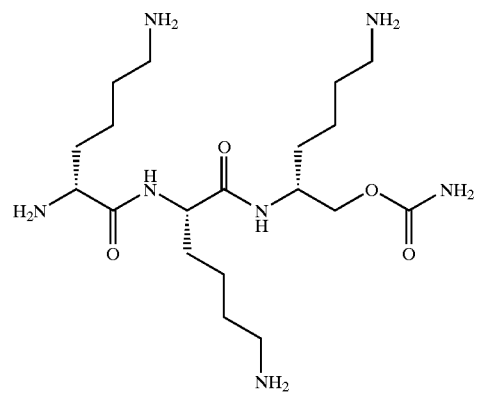

Carbamic acid 6-amino-2-[6-amino-2-(2,6-diamino-hexanoylamino)-hexanoylamino]-hexyl ester (Compound BW);

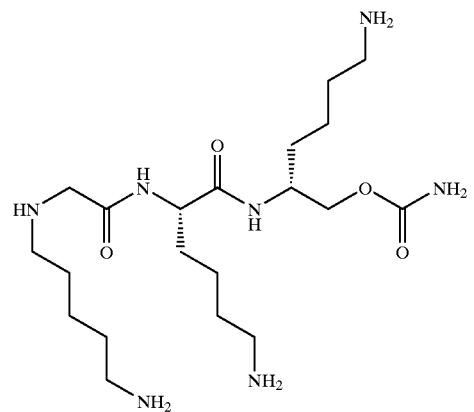

Carbamic acid 6-amino-2-{6-amino-2-[2-(5-amino-pentylamino)-acetylamino]-hexanoylamino}-hexyl ester (Compound BX);

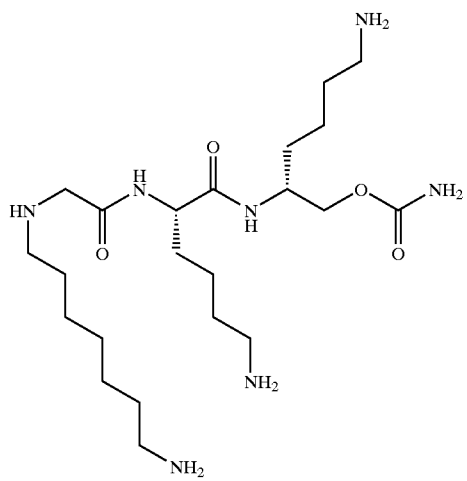

Carbamic acid 6-amino-2-{6-amino-2-[2-(7-amino-heptylamino)-acetylamino]-hexanoylamino}-hexyl ester (Compound BY);

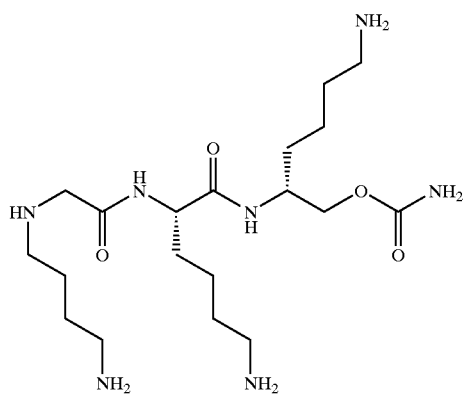

Carbamic acid 6-amino-2-{6-amino-2-[2-(4-amino-butylamino)-acetylamino]-hexanoylamino}-hexyl ester (Compound BZ);

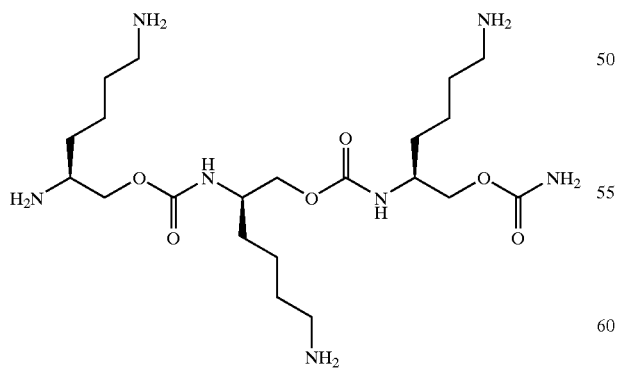

Carbamic acid 6-amino-2-[6-amino-2-(2,6-diamino-hexyloxycarbonylamino)-hexyloxycarbonylamino]-hexyl ester (Compound CA);

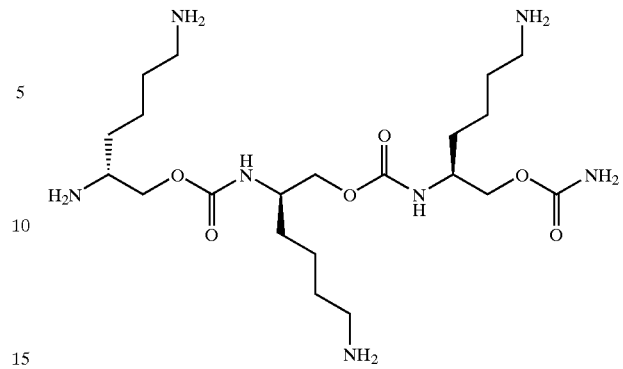

Carbamic acid 6-amino-2-[6-amino-2-(2,6-diamino-hexyloxycarbonylamino)-hexyloxycarbonylamino]-hexyl ester (Compound CB);

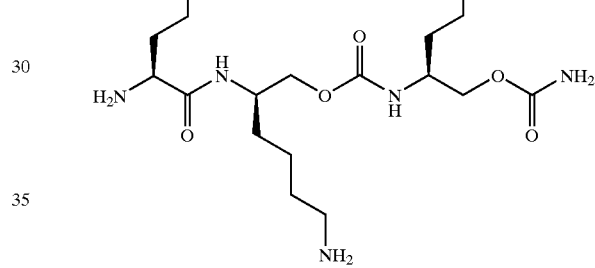

Carbamic acid 6-amino-2-[6-amino-2-(2,6-diamino-hexanoylamino)-hexyloxycarbonylamino]-hexyl ester (Compound CC);

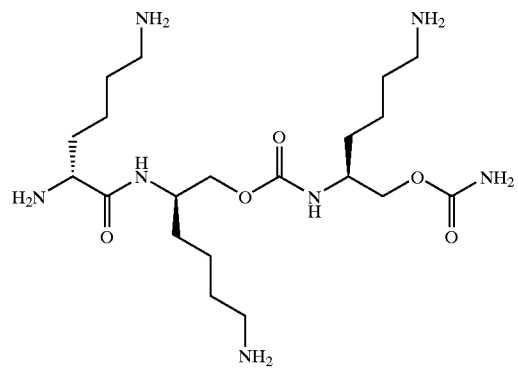

Carbamic acid 6-amino-2-[6-amino-2-(2,6-diamino-hexanoylamino)-hexyloxycarbonylamino]-hexyl ester (Compound CD);

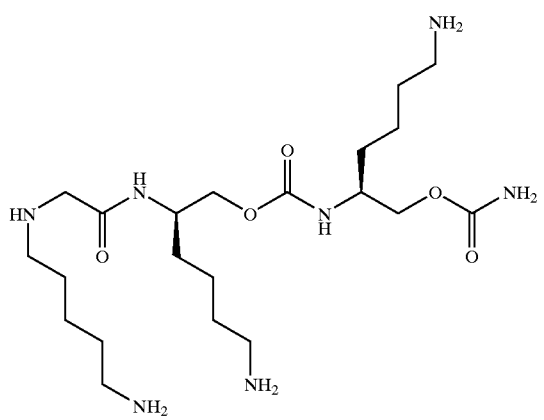

Carbamic acid 6-amino-2-(6-amino-2-[2-(5-amino-pentylamino)-acetylamino]-hexyloxycarbonylamino}-hexyl ester (Compound CE);

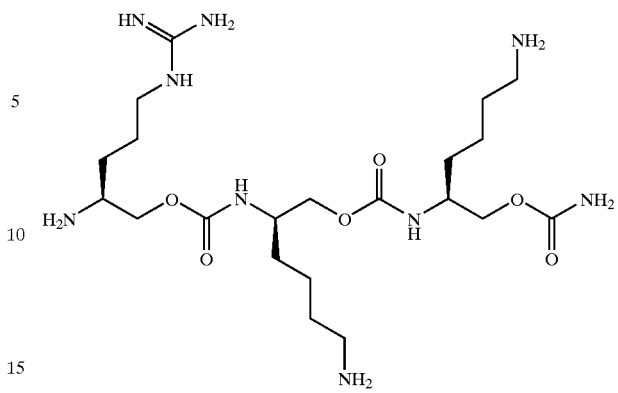

Carbamic acid 6-amino-2-[6-amino-2-(2-amino-5-guanidino-pentyloxycarbonylamino)-hexyloxycarbonylamino]-hexyl ester (Compound CH);

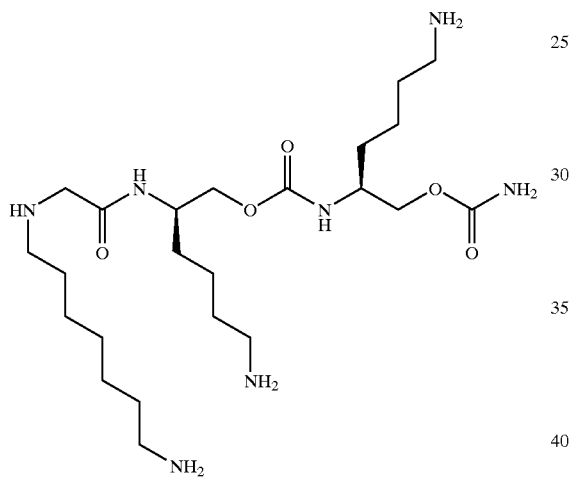

Carbamic acid 6-amino-2-{6-amino-2-[2-(7-amino-heptylamino)-acetylamino]-hexyloxycarbonylamino}-hexyl ester (Compound CF);

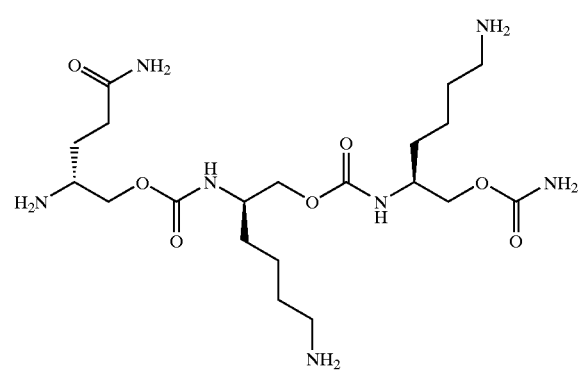

Carbamic acid 6-amino-2-[6-amino-2-(2-amino-5-guanidino-pentyloxycarbonylamino)-hexyloxycarbonylamino]-hexyl ester (Compound CI);

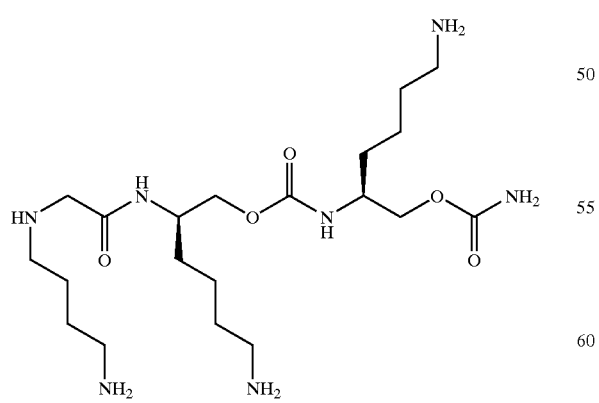

Carbamic acid 6-amino-2-{6-amino-2-[2-(4-amino-butylamino)-acetylamino]-hexyloxycarbonylamino}-hexyl ester (Compound CG);

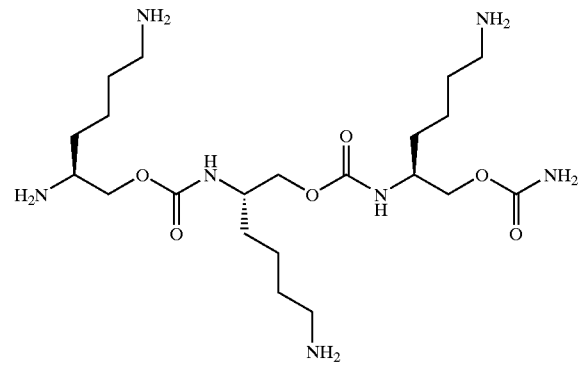

Carbamic acid 6-amino-2-[6-amino-2-(2,6-diamino-hexyloxycarbonylamino)-hexyloxycarbonylamino]-hexyl ester (Compound CJ);

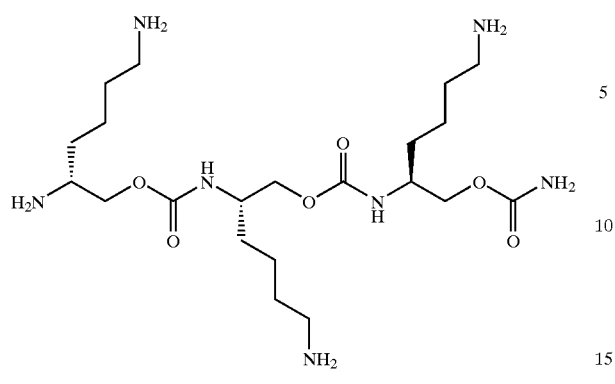

Carbamic acid 6-amino-2-[6-amino-2-(2,6-diamino-hexyloxycarbonylamino)-hexyloxycarbonylamino]-hexyl ester (Compound CK);

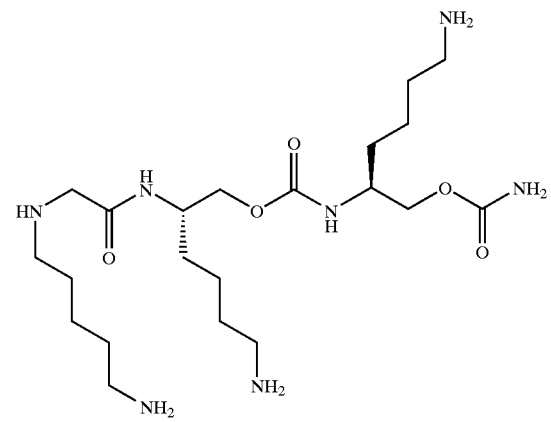

Carbamic acid 6-amino-2-{6-amino-2-[2-(5-amino-pentylamino)-acetylamino]-hexyloxycarbonylamino}-hexyl ester (Compound CN);

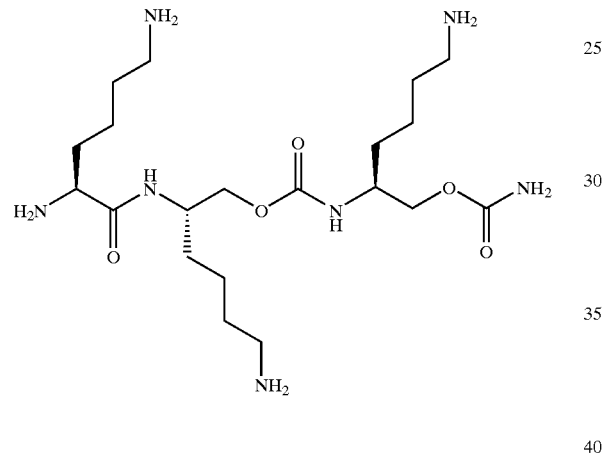

Carbamic acid 6-amino-2-[6-amino-2-(2,6-diamino-hexanoylamino)-hexyloxycarbonylamino]-hexyl ester (Compound CL);

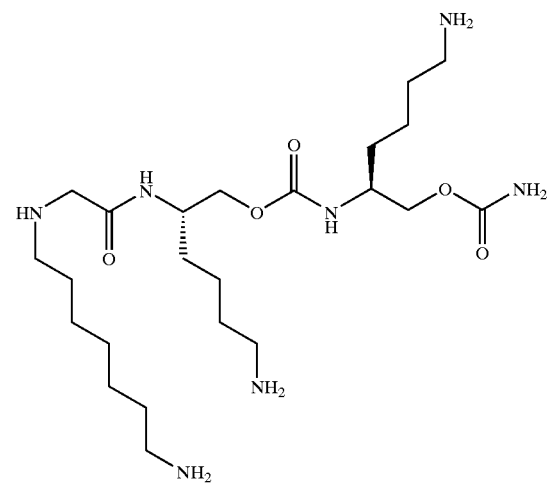

Carbamic acid 6-amino-2-{6-amino-2-[2-(7-amino-heptylamino)-acetylamino]-hexyloxycarbonylamino}-hexyl ester (Compound CO);

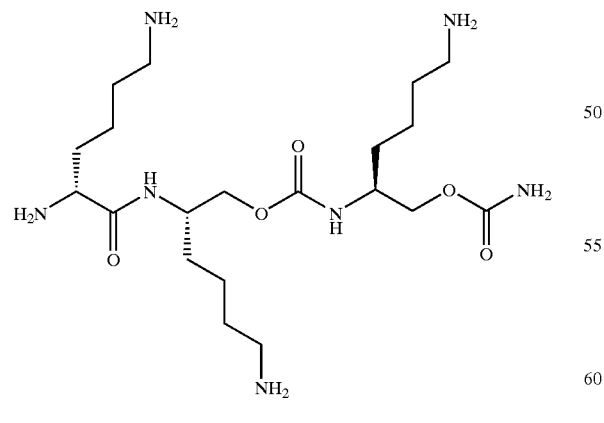

Carbamic acid 6-amino-2-[6-amino-2-(2,6-diamino-hexanoylamino)-hexyloxycarbonylamino]-hexyl ester (Compound CM);

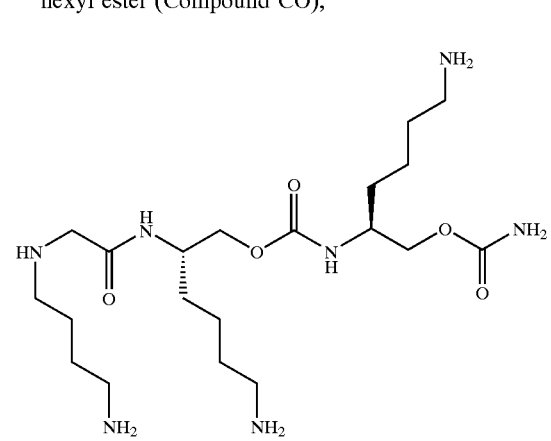

Carbamic acid 6-amino-2-{6-amino-2-[2-(4-amino-butylamino)-acetylamino]-hexyloxycarbonylamino}-hexyl ester (Compound CP);

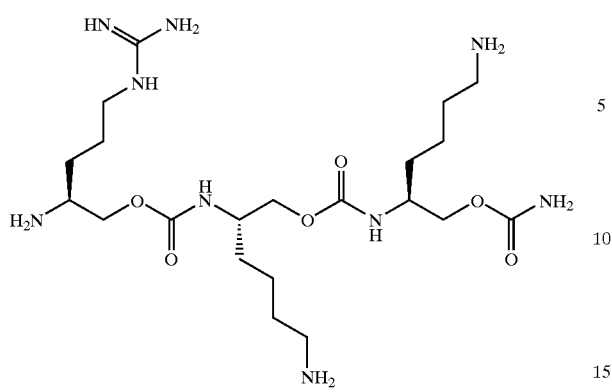

Carbamic acid 6-amino-2-[6-amino-2-(2-amino-5-guanidino-pentyloxycarbonylamino)-hexyloxycarbonylamino]-hexyl ester (Compound CQ);

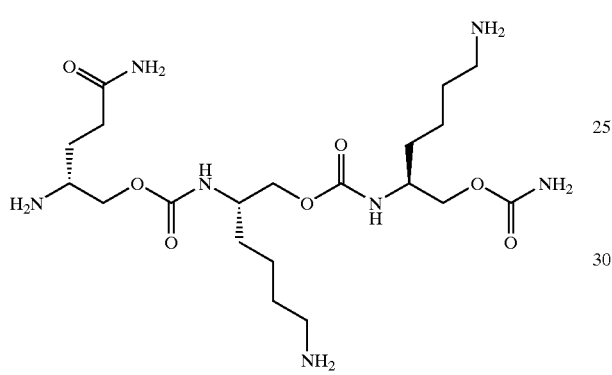

Carbamic acid 6-amino-2-[6-amino-2-(2-amino-4-carbamoyl-butoxycarbonylamino)-hexyloxycarbonylamino]-hexyl ester (Compound CR);

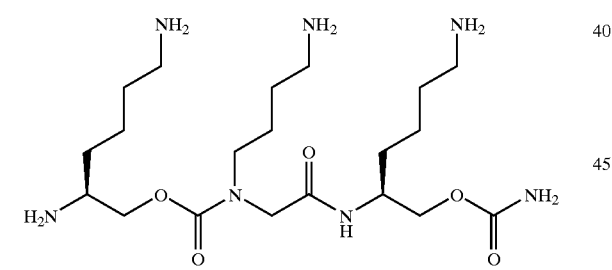

Carbamic acid 6-amino-2-{2-[(4-amino-butyl)-(2,6-diamino-hexyloxycarbonyl)-amino]-acetylamino}-hexyl ester (Compound CS);

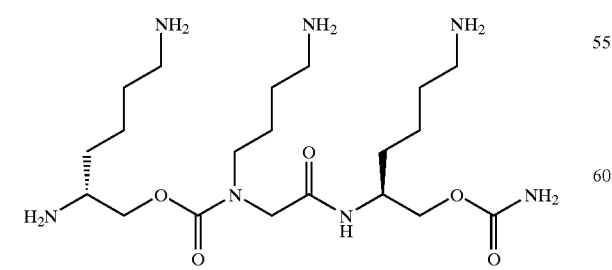

Carbamic acid 6-amino-2-{2-[(4-amino-butyl)-(2,6-diamino-hexyloxycarbonyl)-amino]-acetylamino)-hexyl ester (Compound CT);

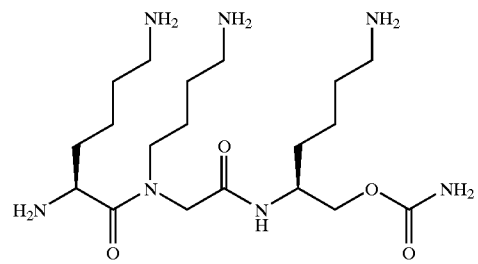

Carbamic acid 6-amino-2-{2-[(4-amino-butyl)-(2,6-diamino-hexanoyl)-amino]-acetylamino}-hexyl ester (Compound CU);

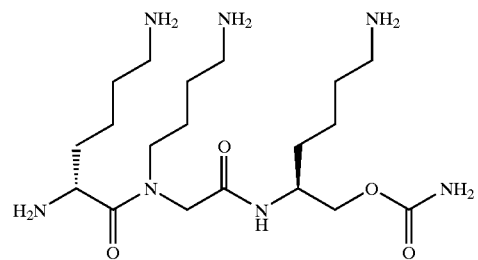

Carbamic acid 6-amino-2-{2-[(4-amino-butyl)-(2,6-diamino-hexanoyl)-amino]-acetylamino}-hexyl ester (Compound CV);

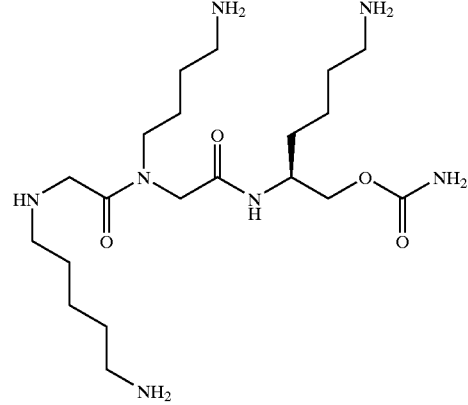

Carbamic acid 6-amino-2-(2-{(4-amino-butyl)-[2-(5-amino-pentylamino)-acetyl]-amino}-acetylamino)-hexyl ester (Compound CW);

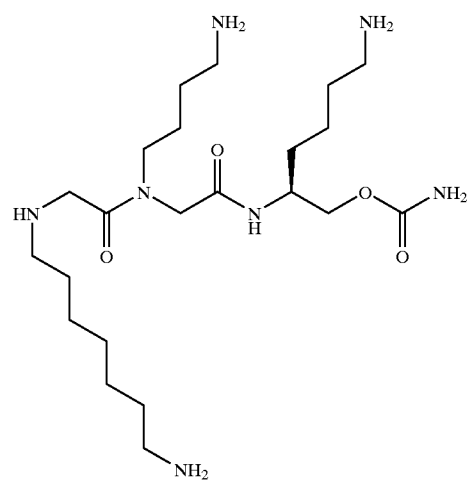

Carbamic acid 6-amino-2-(2-{(4-amino-butyl)-[2-(7-amino-heptylamino)-acetyl]-amino}-acetylamino)-hexyl ester (Compound CX);

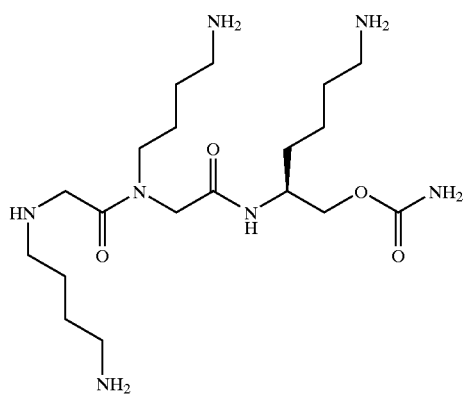

Carbamic acid 6-amino-2-(2-{(4-amino-butyl)-[2-(4-amino-butylamino)-acetyl]-amino}-acetylamino)-hexyl ester (Compound CY);

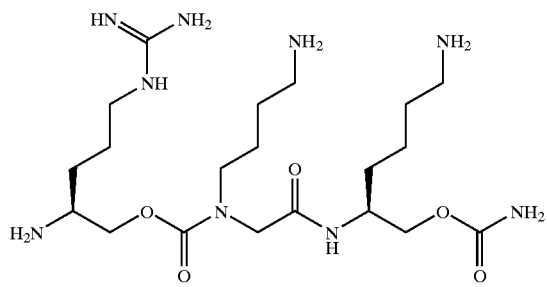

Carbamic acid 6-amino-2-{2-[(4-amino-butyl)-(2-amino-5-guanidino-pentyloxycarbonyl)-amino]-acetylamino}-hexyl ester (Compound CZ);

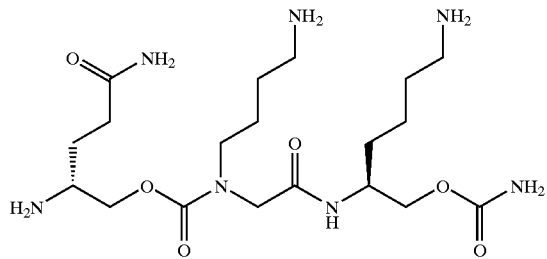

Carbamic acid 6-amino-2-{2-[(4-amino-butyl)-(2-amino-4-carbamoyl-butoxycarbonyl)-amino]-acetylamino}-hexyl ester (Compound DA);

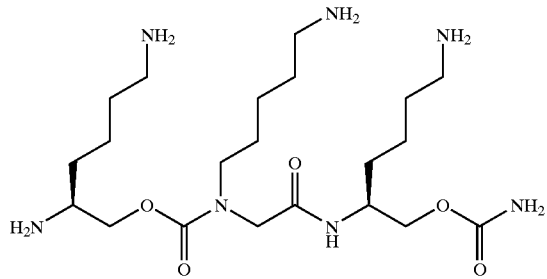

Carbamic acid 6-amino-2-2-[(5-amino-pentyl)-(2,6-diamino-hexyloxycarbonyl)-amino]-acetylamino}-hexyl ester (Compound DB);

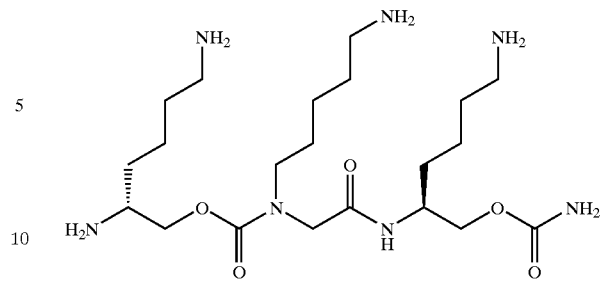

Carbamic acid 6-amino-2-{2-[(5-amino-pentyl)-(2,6-diamino-hexyloxycarbonyl)-amino]-acetylamino}-hexyl ester (Compound DC);

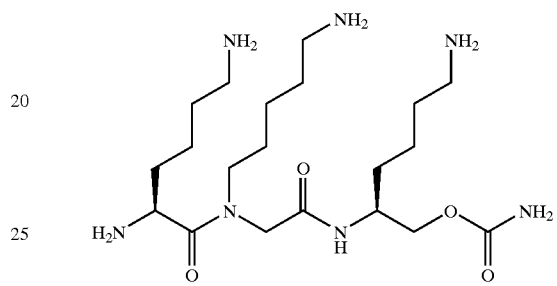

Carbamic acid 6-amino-2-{2-[(5-amino-pentyl)-(2,6-diamino-hexanoyl)-amino]-acetylamino}-hexyl ester (Compound DD);

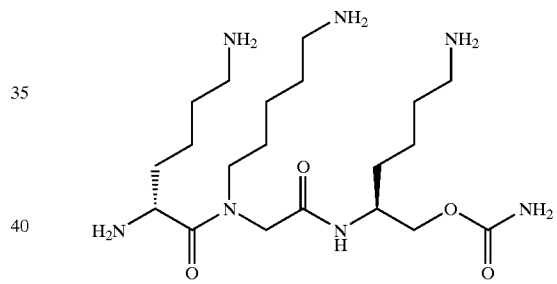

Carbamic acid 6-amino-2-{2-[(5-amino-pentyl)-(2,6-diamino-hexanoyl)-amino]-acetylamino}-hexyl ester (Compound DE);

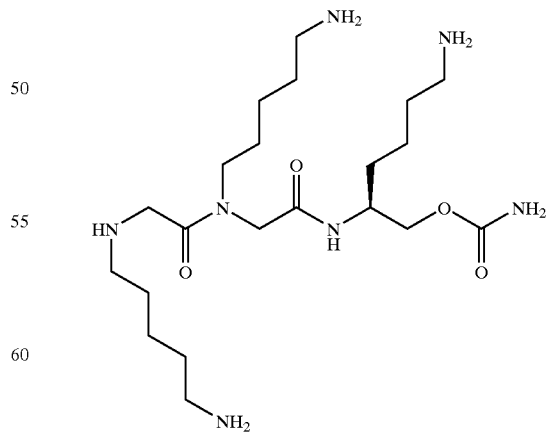

Carbamic acid 6-amino-2-(2-{(5-amino-pentyl)-[2-(5-amino-pentylamino)-acetyl]-amino}-acetylamino)-hexyl ester (Compound DF);

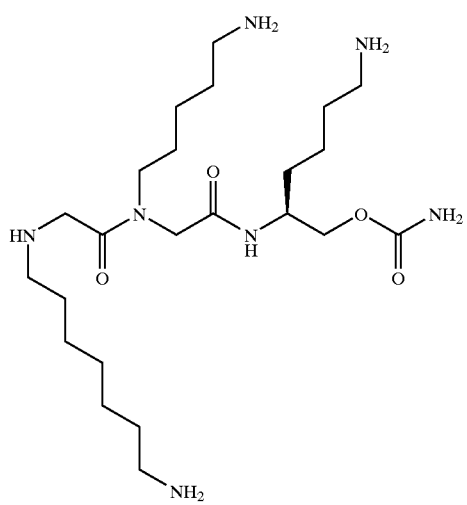

Carbamic acid 6-amino-2-{2-[[2-(7-amino-heptylamino)-acetyl]-(5-amino-pentyl)-amino]-acetylamino}-hexyl ester (Compound DG);

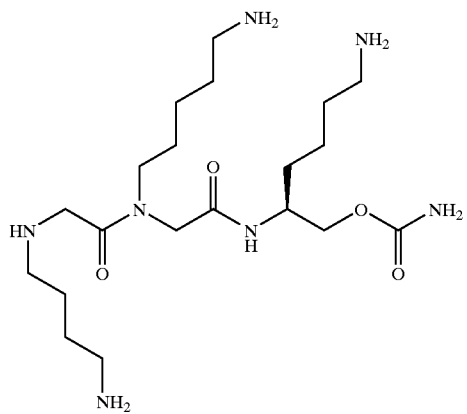

Carbamic acid 6-amino-2-{2-[[2-(4-amino-butylamino)-acetyl]-(5-aminopentyl)-amino]-acetylamino}-hexyl ester (Compound DH);

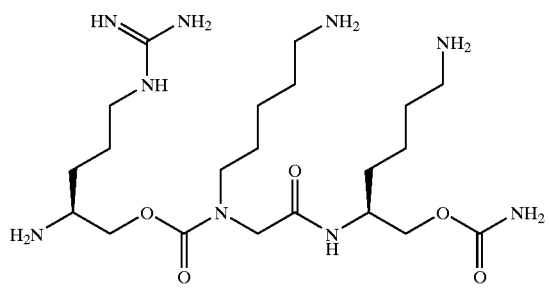

Carbamic acid 6-amino-2-{2-[(2-amino-5-guanidino-pentyloxycarbonyl)-(5-amino-pentyl)-amino]-acetylamino}-hexyl ester (Compound DI);

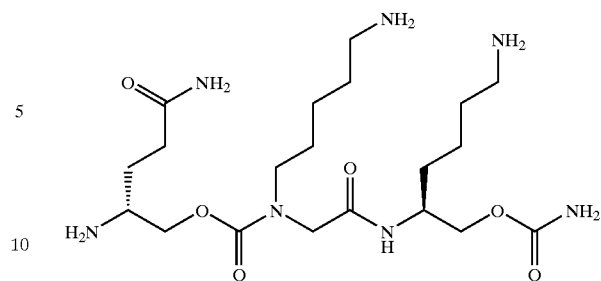

Carbamic acid 6-amino-2-{2-[(2-amino-4-carbamoyl-butoxycarbonyl)-(5-amino-pentyl)-amino]-acetylamino}-hexyl ester (Compound DJ);

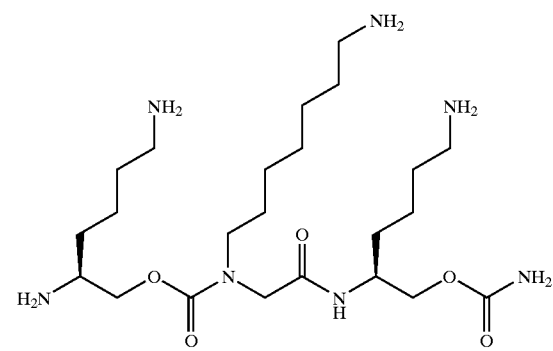

Carbamic acid 6-amino-2-{2-[(7-amino-heptyl)-(2,6-diamino-hexyloxycarbonyl)-amino]-acetylamino}-hexyl ester (Compound DK);

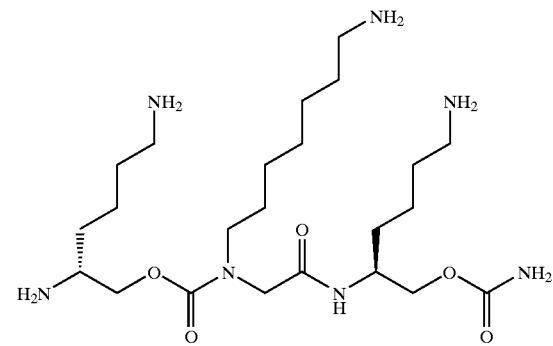

Carbamic acid 6-amino-2-{2-[(7-amino-heptyl)-(2,6-diamino-hexyloxycarbonyl)-amino]-acetylamino}-hexyl ester (Compound DL);

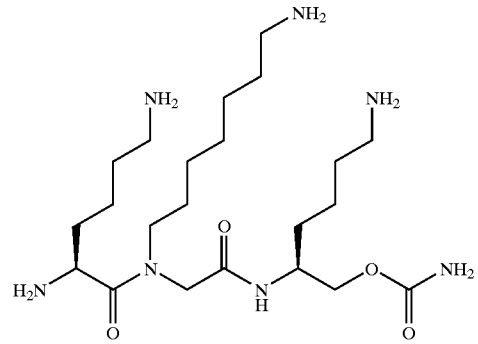

Carbamic acid 6-amino-2-{2-[(7-amino-heptyl)-(2,6-diamino-hexanoyl)-amino]-acetylamino}-hexyl ester (Compound DM);

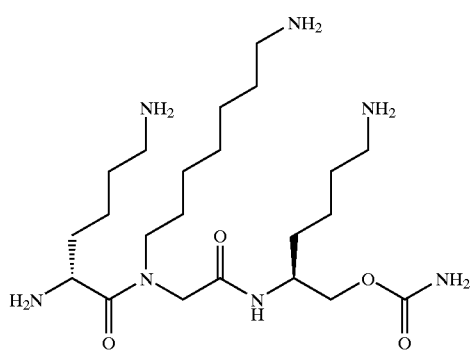

Carbamic acid 6-amino-2-{2-[(7-amino-heptyl)-(2,6-diamino-hexanoyl)-amino]-acetylamino}-hexyl ester (Compound DN);

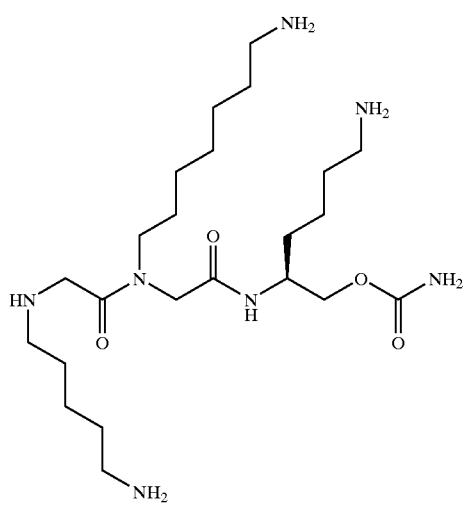

Carbamic acid 6-amino-2-(2-{(7-amino-heptyl)-[2-(5-amino-pentylamino)-acetyl]-amino}-acetylamino)-hexyl ester (Compound DO);

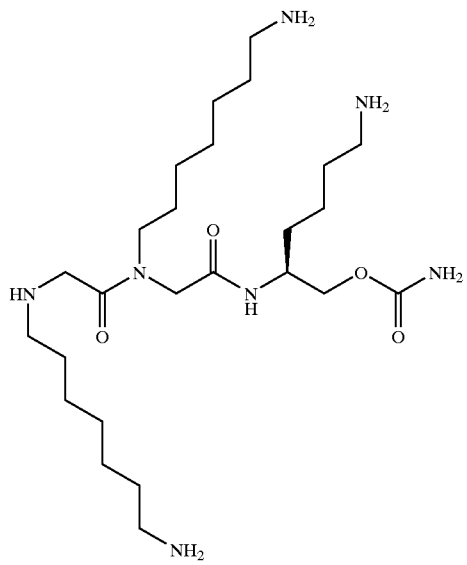

Carbamic acid 6-amino-2-(2-{(7-amino-heptyl)-[2-(7-amino-heptylamino)-acetyl]-amino}-acetylamino)-hexyl ester (Compound DP);

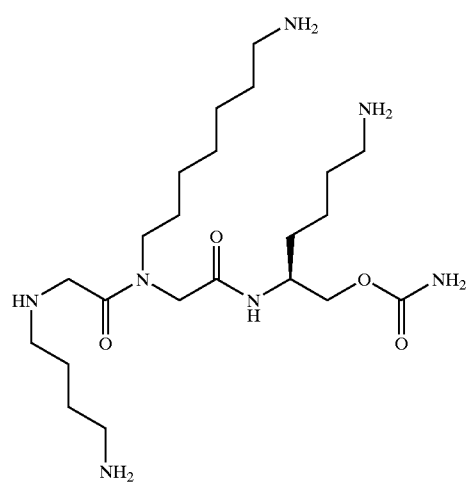

Carbamic acid 6-amino-2-{2-[[2-(4-amino-butylamino)-acetyl]-(7-amino-heptyl)-amino]-acetylamino}-hexyl ester (Compound DQ);

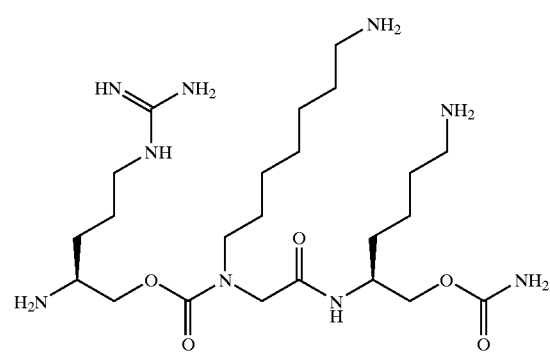

Carbamic acid 6-amino-2-{2-[(2-amino-5-guanidino-pentyloxycarbonyl)-(7-amino-heptyl)-amino]-acetylamino}-hexyl ester (Compound DR);

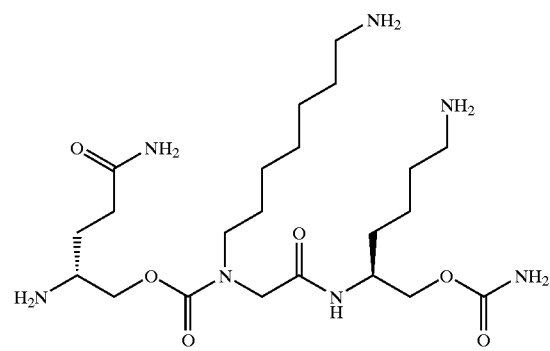

Carbamic acid 6-amino-2-{2-[(2-amino-4-carbamoyl-butoxycarbonyl)-(7-amino-heptyl)-amino]-acetylamino}-hexyl ester (Compound DS);

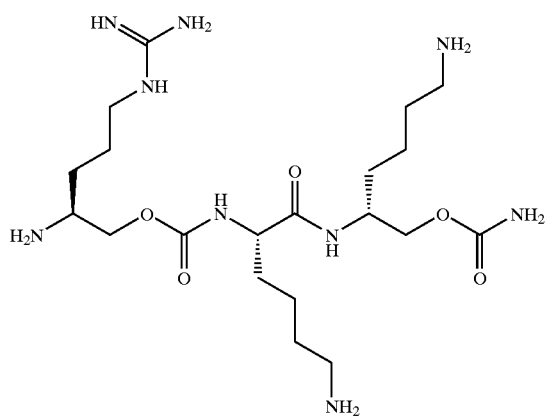

Carbamic acid 6-amino-2-[6-amino-2-(2-amino-5-guanidino-pentyloxycarbonylamino)-hexanoylamino]-hexyl ester (Compound DT);

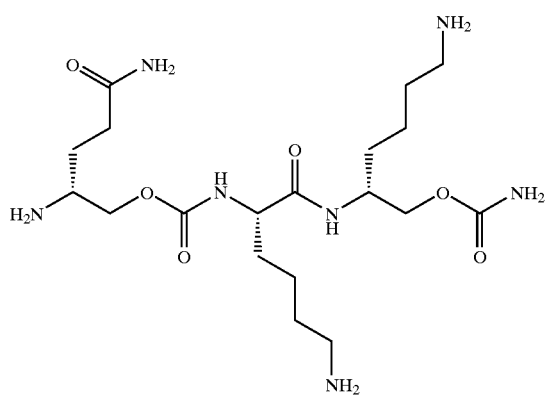

Carbamic acid 6-amino-2-[6-amino-2-(2-amino-4-carbamoyl-butoxycarbonylamino)-hexanoylamino]-hexyl ester (Compound DU); and pharmaceutically acceptable salts thereof.

5.2.2 THE COMPOUNDS OF FORMULA V

The compounds of formula V and pharmaceutically acceptable salts thereof are ureas and can be obtained via conventional methods (see, for example, K. Burgess et al., *J. Am. Chem. Soc.* 119:1556–1564 (1997)).

Figure 2:
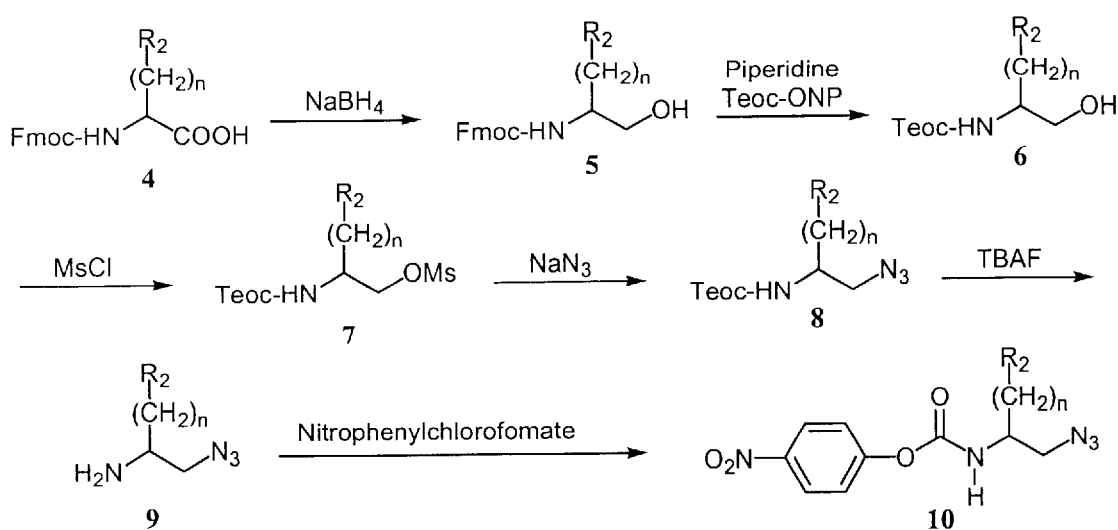
FIG. 2 is a schematic depiction of a general method for synthesizing momoners useful for synthesizing the compounds of formula V. $R_2$ is —$NH_2$, —$NHC(=NH)NH_2$, or —$CH_2C(=NH)NH_2$. n is an integer ranging from 3 to 7.

Urea monomers 10 useful for preparing the compounds of formula V can be obtained according to FIG. 2. The urea monomers are those wherein $R_1$ is —$NH_2$, —NHC(=H)$NH_2$, or —$CH_2$C(=NH)$NH_2$, and m is an integer ranging from 3 to 7. For example, $N^\alpha$-Fmoc protected amino acids 4 can be reduced to their corresponding amino alcohols 5 by reaction with, for example, N-methyl morpholine and isobutyl chloroformate, followed by treatment with, for example, $NaBH_4$. Deprotection of Fmoc group with, for example, 20% piperidine, followed by reaction with Teoc-ONP and pyridine provides N-Teoc-protected amino alcohols 6. Amino alcohols 6 can be converted to their corresponding azide derivatives 8 via, for example, mesylation with methanesulfonylchloride, which provides mesylate intermediates 7. Mesylate intermediates 7 can then be treated with an azide source to provide azide derivatives 8. The Teoc protecting group can be removed from azide derivatives 8 using, for example, TBAF, to provide deprotected intermediates 9. Deprotected intermediates 9 can then be activated as their nitrophenyloxycarbonyl derivatives using 4-nitrophenylchloroformate to provide urea monomers 10. Urea monomers 10 can be purified using conventional silica gel chromatography.

Preferred compounds of formula V are:

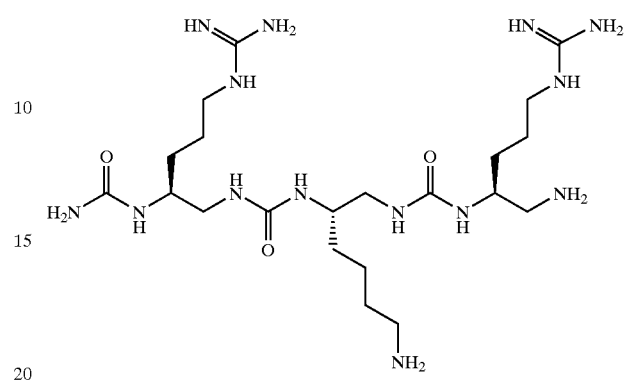

1-{5-Amino-1-[3-(1-aminomethyl-4-guanidino-butyl)-ureidomethyl]-pentyl}-3-(5-guanidino-2-ureido-pentyl)-urea (Compound DV);

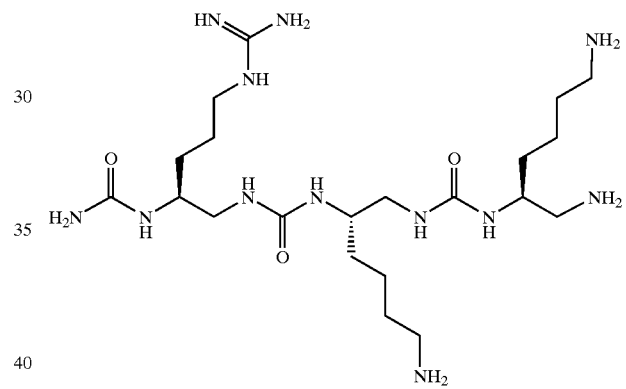

1-{5-Amino-1-[3-(5-amino-1-aminomethyl-pentyl)-ureidomethyl]-pentyl}-3-(5-guanidino-2-ureido-pentyl)-urea (Compound DW);

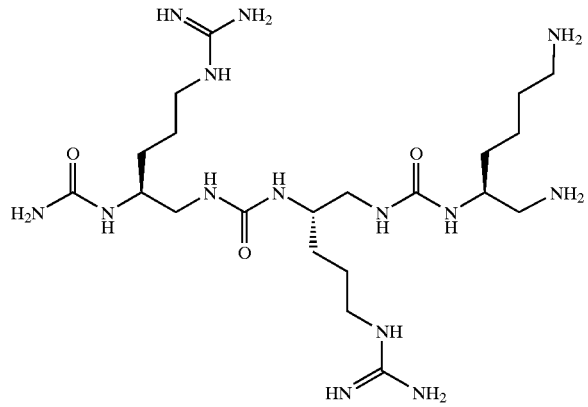

1-{1-[3-(5-Amino-1-aminomethyl-pentyl)-ureidomethyl]-4-guanidino-butyl}-3-(5-guanidino-2-ureido-pentyl)-urea (Compound DX);

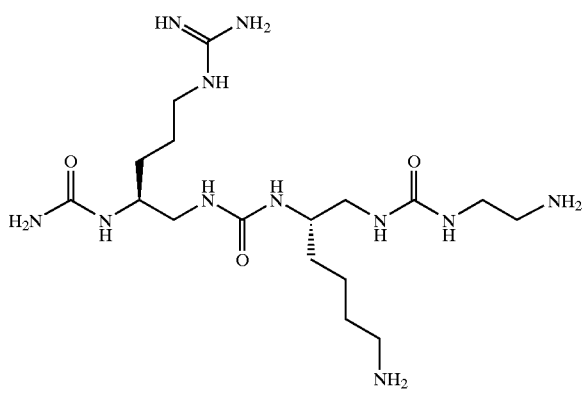

1-{5-Amino-1-[3-(2-amino-ethyl)-ureidomethyl]-pentyl}-3-(5-guanidino-2-ureido-pentyl)-urea (Compound DY); and pharmaceutically acceptable salts thereof.

6. THERAPEUTIC USES OF THE COMPOUNDS OF THE INVENTION

In accordance with the invention, the compounds of the invention can be administered to a patient, preferably a mammal, more preferably a human, suffering from cancer, inflammation, or a viral infection. In one embodiment, "treatment" or "treating" refers to an amelioration of cancer, inflammation, or a viral infection, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of cancer, inflammation, or a viral infection, either physically, e.g., stabilization of a discernible symptom, physiologically, e.g., stabilization of a physical parameter, or both. In yet another embodiment, "treatment" or "treating" refers to delaying the onset of cancer, inflammation, or a viral infection.

In certain embodiments, a compound of the invention is administered to a patient, preferably a mammal, more preferably a human, as a preventative measure against cancer, inflammation, or a viral infection. As used herein, "prevention" or "preventing" refers to a reduction of the risk of acquiring cancer, inflammation, or a viral infection. In one embodiment, a compound of the invention is administered as a preventative measure to a patient. According to this embodiment, the patient can have a genetic or a non-genetic predisposition to cancer, inflammation, or a viral infection. Accordingly, the compounds of the invention can be used for the treatment of one manifestation of cancer, inflammation, or a viral infection and prevention of another.

6.1 TYPES OF CANCER TREATABLE OR PREVENTABLE USING THE COMPOUNDS OF THE INVENTION

The compounds of the invention are useful for treating or preventing a variety of cancers, including, but not limited to, Leukemias, including but not limited to acute leukemia, acute lymphocytic leukemia, acute myelocytic leukemia, myeloblastic, promyelocytic, myelomonocytic, monocytic, erythroleukemia, chronic leukemia, chronic myelocytic, (granulocytic) leukemia, chronic lymphocytic leukemia, Polycythemia vera, Lymphomas including but not limited to Hodgkin's disease, non-Hodgkin's disease, Multiple mycloma, Waldenström's macroglobulinemia, Heavy chain disease, Solid tumors including but not limited to sarcomas and carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, and neuroblastomaretinoblastoma.

6.2 TYPES OF INFLAMMATION TREATABLE OR PREVENTABLE USING THE COMPOUNDS OF THE INVENTION

The compounds of the invention are useful for treating or preventing several types of inflammation, including, but not limited to, eczema, inflammatory bowel disease, rheumatoid arthritis, asthma, psoriasis, ischemia/reperfusion injury, ulcerative colitis and acute respiratory distress syndrome.

6.3 TYPES OF VIRAL INFECTIONS TREATABLE OR PREVENTABLE USING THE COMPOUNDS OF THE INVENTION

The compounds of the invention are useful for treating or preventing a variety of viral infections, including, but not limited to those caused by infection with hepatitis B, hepatitis C, rotavirus, human immunodeficiency virus type I (HIV-I), human immunodeficiency virus type II (HIV-II), human T-cell lymphotropic virus type I (HTLV-I), human T-cell lymphotropic virus type II (HTLV-II), AIDS, DNA viruses such as hepatitis type B and hepatitis type C virus; parvoviruses, such as adeno-associated virus and cytomegalovirus; papovaviruses such as papilloma virus, polyoma viruses, and SV40; adenoviruses; herpes viruses such as herpes simplex type I (HSV-I), herpes simplex type II (HSV-II), and Epstein-Barr virus; poxviruses, such as variola (smallpox) and vaccinia virus; and RNA viruses, such as human immunodeficiency virus type I (HIV-I), human immunodeficiency virus type II (HIV-II), human T-cell lymphotropic virus type I (HTLV-I), human T-cell lymphotropic virus type II (HTLV-II), influenza virus, measles virus, rabies virus, Sendai virus, picornaviruses such as poliomyelitis virus, coxsackieviruses, rhinoviruses, reoviruses, togaviruses such as rubella virus (German measles) and Semliki forest virus, arboviruses, and hepatitis type A virus.

6.4 THERAPEUTIC/PROPHYLACTIC ADMINISTRATION OF THE COMPOUNDS OF THE INVENTION

Due to their activity, the compounds of the invention are advantageously useful in veterinary and human medicine. As described above, the compounds of the invention are useful for the treatment or prevention of cancer, inflammation, or a viral infection in a patient.

When administered to a patient, a compound of the invention is preferably administered as component of a composition that optionally comprises a pharmaceutically acceptable vehicle. The present compositions, which comprise a compound of the invention, are preferably administered orally. The compositions of the invention may also be administered by any other convenient route, for example, by infusion or bolus injection, by absorption through epithelial or mucocutaneous linings (e.g., oral mucosa, rectal, and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer the compounds of the invention.

In certain embodiments, the present compositions can comprise one or more compounds of the invention.

Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In most instances, administration will result in the release of a compound of the invention into the bloodstream.

In specific embodiments, it may be desirable to a compound of the invention locally. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In certain embodiments, it may be desirable to introduce a compound of the invention into the central nervous system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and vehicles such as triglycerides.

In another embodiment, the compounds of the invention can be delivered in a vesicle, in particular a liposome (see Langer, 1990, *Science* 249:1527–1533; Treat et al., in Liposomes in the Therapy of Infectious Disease and Cancer, Lopez-Berestein and Fidler (eds.), Liss, N.Y., pp. 353–365 (1989); Lopez-Berestein, ibid., pp. 317–327; see generally ibid.).

In yet another embodiment, the compounds of the invention can be delivered in a controlled release system (see, e.g., Goodson, in Medical Applications of Controlled Release, supra, vol. 2, pp. 115–138 (1984)). Other controlled-release systems discussed in the review by Langer, 1990, *Science* 249:1527–1533) may be used. In one embodiment, a pump may be used (see Langer, supra; Sefton, 1987, *CRC Crit. Ref. Biomed. Eng.* 14:201; Buchwald et al., 1980, *Surgery* 88:507 Saudek et al., 1989, *N. Engl. J. Med.* 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105). In yet another embodiment, a controlled-release system can be placed in proximity of a target of a compound of the invention, e.g., a particular RNA, thus requiring only a fraction of the systemic dose.

The present compositions can optionally comprise a suitable amount of a pharmaceutically acceptable vehicle so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, mammals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in *Remington's Pharmaceutical Sciences*, Alfonso R. Gennaro ed., Mack Publishing Co. Easton, Pa., 19th ed., 1995, pp. 1447 to 1676, incorporated herein by reference.

In a preferred embodiment, the compounds of the invention are formulated in accordance with routine procedures as a pharmaceutical composition adapted for oral administration to human beings. Compositions for oral delivery may be in the form of tablets, lozenges, aqueous or oily suspensions, granules, powders, emulsions, capsules, syrups, or elixirs, for example. Orally administered compositions may contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade. Typically, compositions for intravenous administration comprise sterile isotonic aqueous buffer. Where necessary, the compositions may also include a solubilizing agent.

In another embodiment, the compounds of the invention can be formulated for intravenous administration. Compositions for intravenous administration may optionally include a local anesthetic such as lignocaine to lessen pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compounds of the invention are to be administered by infusion, they can be dispensed, for example, with an infusion bottle containing sterile pharmaceutical grade water or saline. Where the compounds of the invention are administered by injection, an ampoule of sterile water for injection or saline can be provided so that the ingredients may be mixed prior to administration.

The amount of a compound of the invention that will be effective in the treatment of a particular type of cancer, inflammation, or viral infection disclosed herein will depend on the nature of the disorder or condition, and can be determined by standard clinical techniques. In addition, in vitro or in vivo assays may optionally be employed to help identify optimal dosage ranges. The precise dose to be employed will also depend on the route of administration, and the seriousness of the disease or disorder, and should be decided according to the judgment of the practitioner and each patient's circumstances. However, suitable dosage ranges for oral administration are generally about 0.001 milligram to about 200 milligrams of a compound of the invention or a pharmaceutically acceptable salt thereof per kilogram body weight per day. In specific preferred embodiments of the invention, the oral dose is about 0.01 milligram to about 100 milligrams per kilogram body weight per day, more preferably about 0.1 milligram to about 75 milligrams per kilogram body weight per day, more preferably about 0.5 milligram to 5 milligrams per kilogram body weight per day. The dosage amounts described herein refer to total amounts administered; that is, if more than one compound of the invention is administered, or if a compound of the invention is administered with a therapeutic agent, then the preferred dosages correspond to the total amount administered. Oral compositions preferably contain about 10% to about 95% active ingredient by weight.

Suitable dosage ranges for intravenous (i.v.) administration are about 0.01 milligram to about 100 milligrams per kilogram body weight per day, about 0.1 milligram to about 35 milligrams per kilogram body weight per day, and about 1 milligram to about 10 milligrams per kilogram body weight per day. Suitable dosage ranges for intranasal administration are generally about 0.01 pg/kg body weight per day to about 1 mg/kg body weight per day. Suppositories generally contain about 0.01 milligram to about 50 milligrams of a compound of the invention per kilogram body weight per day and comprise active ingredient in the range of about 0.5% to about 10% by weight.

Recommended dosages for intradermal, intramuscular, intraperitoneal, subcutaneous, epidural, sublingual, intracerebral, intravaginal, transdermal administration or administration by inhalation are in the range of about 0.001 milligram to about 200 milligrams per kilogram of body weight per day. Suitable doses for topical administration are in the range of about 0.001 milligram to about 1 milligram, depending on the area of administration. Effective doses may be extrapolated from dose-response curves derived from in vitro or animal model test systems. Such animal models and systems are well known in the art.

The invention also provides pharmaceutical packs or kits comprising one or more vessels containing a compound of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains more than one compound of the invention. In another embodiment, the kit comprises a therapeutic agent and a compound of the invention.

The compounds of the invention are preferably assayed in vitro and in vivo, for the desired therapeutic or prophylactic activity, prior to use in humans. For example, in vitro assays can be used to determine whether it is preferable to administer a compound of the invention alone or in combination with another compound of the invention and/or a therapeutic agent. Animal model systems can be used to demonstrate safety and efficacy.

Other methods will be known to the skilled artisan and are within the scope of the invention.

6.5 COMBINATION THERAPY

In certain embodiments of the present invention, a compound of the invention can be used in combination therapy with at least one other therapeutic agent. The compound of the invention and the therapeutic agent can act additively or, more preferably, synergistically. In a preferred embodiment, a composition comprising a compound of the invention is administered concurrently with the administration of another therapeutic agent, which can be part of the same composition as or in a different composition from that comprising the compound of the invention. In another embodiment, a composition comprising a compound of the invention is administered prior or subsequent to administration of another therapeutic agent. As many of the disorders for which the compounds of the invention are useful in treating are chronic, in one embodiment combination therapy involves alternating between administering a composition comprising a compound of the invention and a composition comprising another therapeutic agent, e.g., to minimize the toxicity associated with a particular drug. The duration of administration of the compound of the invention or therapeutic agent can be, e.g., one month, three months, six months, a year, or for more extended periods. In certain embodiments, when a compound of the invention is administered concurrently with another therapeutic agent that potentially produces adverse side effects including, but not limited to, toxicity, the therapeutic agent can advantageously be administered at a dose that falls below the threshold at which the adverse side is elicited.

The therapeutic agent can be an anti-cancer agent. Useful anti-cancer agents include, but are not limited to, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel, γ-radiation, alkylating agents including nitrogen mustard such as cyclophosphamide, Ifosfamide, trofosfamide, Chlorambucil, nitrosoureas such as carmustine (BCNU), and Lomustine (CCNU), alkylsulphonates such as busulfan, and Treosulfan, triazenes such as Dacarbazine, platinum containing compounds such as Cisplatin and carboplatin, plant alkaloids including vinca alkaloids, vincristine, Vinblastine, Vindesine, and Vinorelbine, taxoids including paclitaxel, and Docetaxol, DNA topoisomerase inhibitors including Epipodophyllins such as etoposide, Teniposide, Topotecan, 9-aminocamptothecin, campto irinotecan, and crisnatol, mytomycins such as mytomycin C, and Mytomycin C, anti-metabolites, including anti-folates such as DHFR inhibitors, methotrexate and Trimetrexate, IMP dehydrogenase inhibitors including mycophenolic acid, Tiazofurin, Ribavirin, EICAR, Ribonuclotide reductase Inhibitors such as hydroxyurea, deferoxamine, pyrimidine analogs including uracil analogs 5-Fluorouracil, Floxuridine, Doxifluridine, and Ratitrexed, cytosine analogs such as cytarabine (ara C), cytosine arabinoside, and fludarabine, purine analogs such as mercaptopurine, thioguanine, hormonal therapies including receptor antagonists, the anti-estrogens Tamoxifen, Raloxifene and mcgestrol, LHRH agonists such as goscrclin, and Leuprolide acetate, anti-androgens such as flutamide, and bicalutamide, retinoids/deltoids, Vitamin D3 analogs including EB 1089, CB 1093, and KH 1060, photodyamic therapies including vertoporfin (BPD-MA), Phthalocyanine, photosensitizer Pc4, Demethoxy-hypocrellin A, (2BA-2-DMHA), cytokines including Interferon-α, Interferon-γ, tumor necrosis factor, as well as other compounds having anti-tumor activity including Isoprenylation inhibitors such as Lovastatin, Dopaminergic neurotoxins such as 1-methyl-4-phenylpyridinium ion, Cell cycle inhibitors such as staurosporine, Actinomycins such as Actinomycin D and Dactinomycin, Bleomycins such as bleomycin A2, Bleomycin B2, and Peplomycin, anthracyclines such as daunorubicin, Doxorubicin (adriamycin), Idarubicin, Epirubicin, Pirarubicin, Zorubicin, and Mitoxantrone, MDR inhibitors including verapamil, and $Ca^{2+}$ ATPase inhibitors such as thapsigargin.

The therapeutic agent can be an anti-inflammatory agent. Useful anti-inflammatory agents include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide; leukotriene antagonists including, but not limited to, zileuton, aurothioglucose, gold sodium thiomalate and auranofin; and other anti-inflammatory agents including, but not limited to, colchicine, allopurinol, probenecid, sulfinpyrazone and benzbromarone.

The therapeutic agent can be an antiviral agent. Useful antiviral agents include, but are not limited to, nucleoside analogs, such as zidovudine, acyclovir, gangcyclovir, vidarabine, idoxuridine, trifluridine, and ribavirin, as well as foscarnet, amantadine, rimantadine, saquinavir, indinavir, ritonavir, and the alpha-interferons.

7. EXAMPLES: CHEMICAL SYNTHESIS
7.1 SYNTHESIS OF CARBAMATE MONOMERS 3 DERIVED FROM L-ARG, D-ARG, L-LYS, AND D-LYS 10 mmol of each of $N^\alpha$-Fmoc-protected L-Arg, D-Arg, L-Lys, and D-Lys were reduced to its corresponding amino alcohols by reaction with N-methyl morpholine (10 mmol) and isobutyl chloroformate (10 mmol) in 1,2-dimethoxyethane (10 mL) at −15° C., followed by treatment with $NaBH_4$ (30 mmol) in water (10 mL). The resulting product was dissolved in pyridine (10 mmol) and dichloromethane (25 mL) and treated with 4-nitrochlorophenylchloroformate at 0° C. for 3 h. Purification using silicagel chromatography provided carbamate monomers 3 derived from each of L-Arg, D-Arg, L-Lys, and D-Lys in approximately 85% yield.

7.2. SYNTHESIS OF UREA MONOMERS 10 DERIVED FROM L-ARG, L-LYS, L-GLU, L,-GLN, GLY, AND L-TYR 10 mmol of each of L-Arg, L-Lys, L-Glu, L-Gln, Gly, and L-Tyr were reduced to its corresponding amino alcohol by the reaction with N-methyl morpholine (10 mmol) and isobutyl chlorofornate (10 mmol) in 1,2-dimethoxyethane (10 mL) at −15° C., followed by treatment with $NaBH_4$(30 mmol) in water (10 mL). Deprotection of the resulting product's Fmoc group using 20% piperidine in dichloromethane (50 mL) at room temperature for 1 h, followed by reaction with 2-(trimethylsilyl)ethyl-4-nitrophenyl carbonate (1 equiv.) and pyridine (1 equiv.) in dichloromethane (25 mL) provided a Teoc-protected amino alcohol. The amino alcohol was converted to its corresponding azide through mesylation with methanesulfonylchloride (1.2 equiv.) and pyridine (1.2 equiv.) in dichloromethane (25 mL) at 0° C. The resulting product was treated with $NaN_3$ (10 equiv.) in dimethylformamide (25 mL) at 60° C. for 6 h. The product's Teoc protecting group was removed with 1.0 M tetrabutylammonium fluoride in THF (20 mL). The resulting free amine was activated as its nitrophenyloxycarbonyl derivative with 4-nitrophenylchloroformate (1.2 equiv.) in presence of pyridine (1.2 equiv.) in dichloromethane at 0° C. Purification using silica gel chromatography provided urea monomers 10 derived from each of L-Arg, L-Lys, L-Glu, L-Gin, Gly, and L-Try in approximately 35% yield.

7.3 SYNTHESIS OF COMPOUND DW

Figure 4:
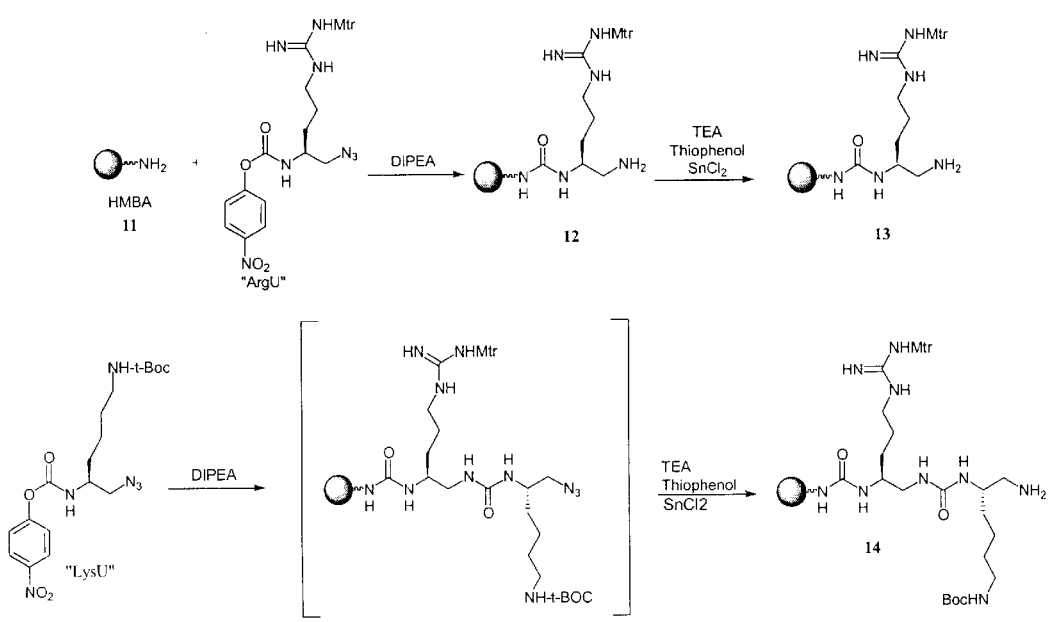
FIG. 4 and FIG. 5 show a synthesis of Compound DW.
Figure 5:
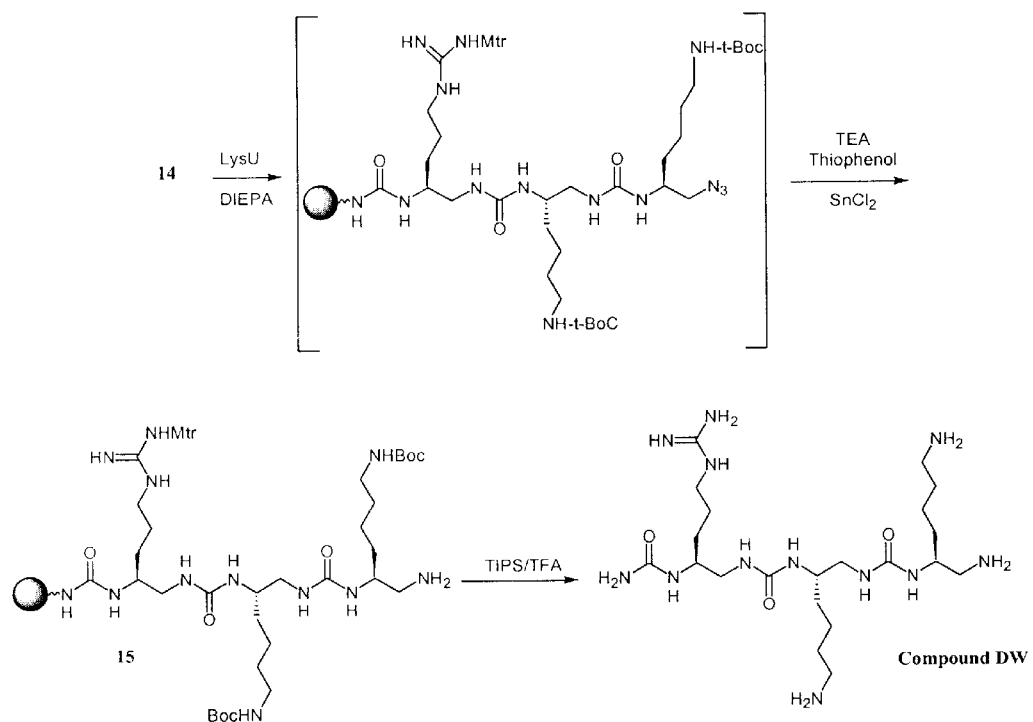

Compound DW was synthesized according to FIG. 4 and FIG. 5. In particular, 54 mg of rink amide HMBA resin (11) (Calbiochem-Novabiochem Corp., La Jolla, Calif.), was washed with methylene chloride (3 mL×5 min×2), and suspended in 20% DMF in methylene chloride (2 mL). To the suspended resin was added ArgU (54 mg) in DIPEA (60 uL), and the resulting suspension was allowed to stir overnight at room temperature to provide resin 12.

Resin 12 was washed with DMF (3 mL×5 min×3) and with methylene chloride (3 mL×5 min×2), suspended in THF (1 mL), and stirred for 20 minutes at room temperature, and to the suspension was added TEA (120 μL), thiophenol (62 uL), and tin(II) chloride (30 mg). The resulting reaction mixture was allowed to stir for 6 h at room temperature, providing resin 13.

Resin 13 was washed with DMF (3 mL×5 mm×3) and methylene chloride (3 mL×5 min×2). Two successive iterations of LysU (40 mg×2) coupling were performed, affording resins 14 and 15, respectively, (FIG. 4 and FIG. 5) as described above for ArgU. The resin 15 was deprotected and cleaved from resin using 2% TIPS and 2% water in TFA (2 mL) for 6 h at room temperature. The reaction suspension was filtrated off, and the filtrate was evaporated under reduced pressure to provide a residue. The residue was dissolved in TFA (100 uL), and a crude product was precipitated by addition of ethyl ether (10 mL). HPLC purification using gradient elution (0.1% $TFA/H_2O$; 0.1% TFA/$CH_3CN$, 100; 0 to 0; 100) of the crude product afforded 3 mg of Compound DW as a white solid trimer: FAB/MS m/z 538 $(M+Na)^+$.

7.4 SYNTHESIS OF COMPOUND AU

Figure 3:
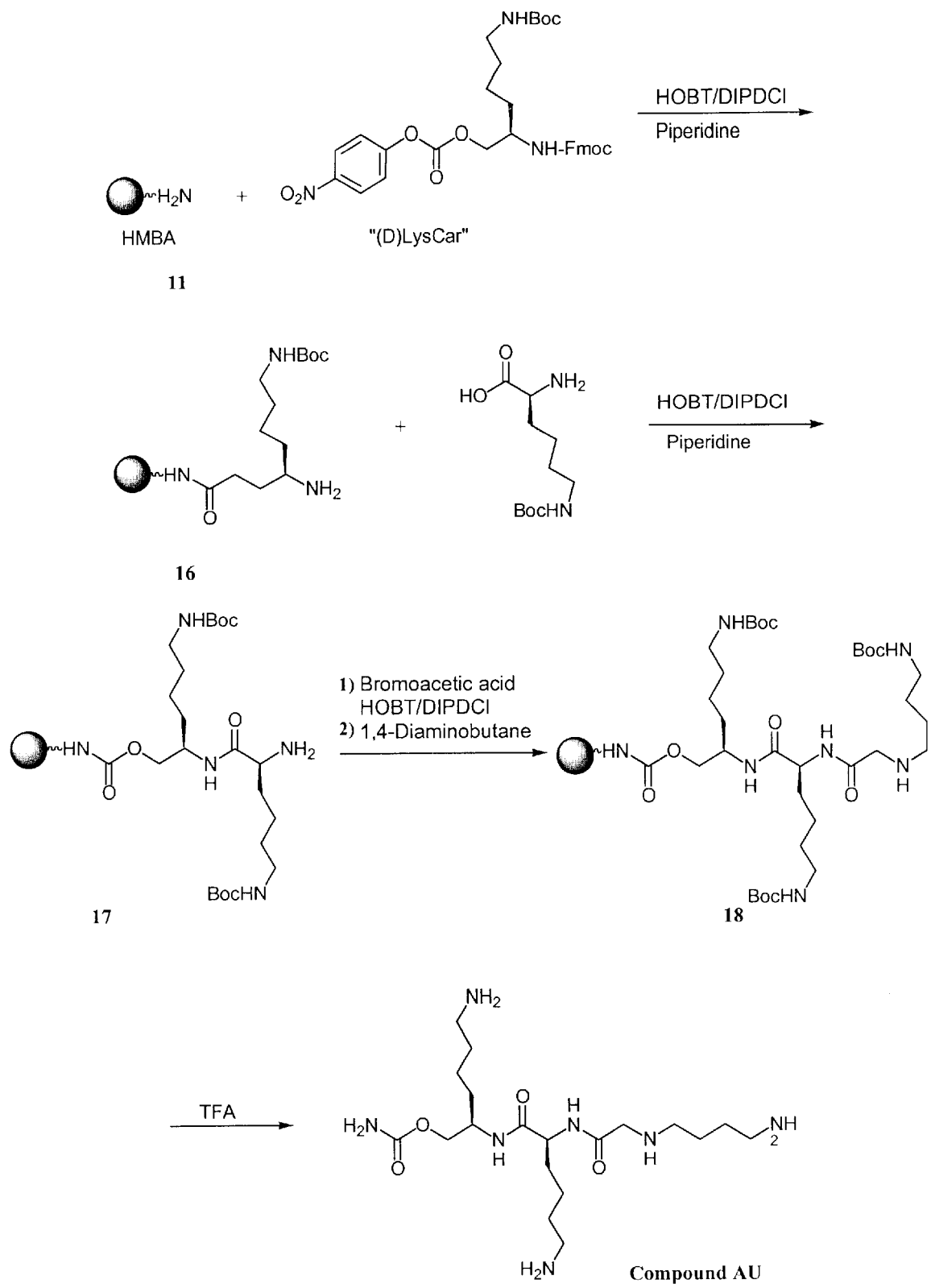
FIG. 3 is a schematic depiction of a synthesis of Compound AU.

Compound AU was synthesized according to FIG. 3. In particular, 54 mg of rink amide MBHA resin, 4-(2',4'-dimethoxyphenyl-Fmoc-aminomethyl)-phenoxyacetamido-norleucyl-methylbenzhydrylamine 11 (Calbiochem-Novabiochem Corp., La Jolla, Calif.), was washed with methylene chloride (3 mL×5 min×2) and suspended in 20% DMF in methylene chloride (2 mL). To the suspension was added HOBT (240 µL of 1M in NMP and (D)-LysCar monomer (0.12 mmol). The resulting mixture was allowed to stir for 20 minutes at room temperature, and then 1,3-diisopropyldicarboimide ("DIPDCI") (0.06 mmol) was added. The resulting mixture was allowed to stir overnight at room temperature. The solvent was drained and the reaction resin was washed with DMF (10 mL×5 min×3) and methylene chloride (10 mL×5 min×2) and treated with 5% piperidine/DMF (2 mL) for 10 minutes at room temperature. The solvent was drained, and the resin was retreated with 5% piperidine/DMF (2 mL) for another 20 min at room temperature and washed extensively with DMF, methanol, and methylene chloride to provide resin 16.

Resin 16 was resuspended in 20% DMF in methylene chloride (2 mL), and then to the suspension was added HOBT (300 uL of 1M in NMP) and N-ε-(tert-butoxycarbonyl)-L-lysine (0.3 mmol). The resulting mixture was allowed to stir for 20 minutes at room temperature, and then DIPDCI (0.06 mmol) was added. The resulting mixture was allowed to stir overnight at room temperature. The solvents were drained, and the resin was washed with DMF (10 mL×5 mm×3) and methylene chloride (10 mL×5 min×2) and treated with 2 mL of 5% piperidine/DMF for 10 min at room temperature. The solvent was drained, and the resin was retreated with 5% piperidine/DMF (2 mL) for another 20 min at room temperature and washed extensively with DMF, methanol, and methylene chloride to provide resin 17.

Resin 17 was resuspended in 5% DMF/methylene chloride (2 mL) and allowed to stir for 20 min at room temperature. Bromoacetic acid (140 mg) and HOBT (1 mL of 1M in NMP) was added to the resulting suspension, which was allowed to stir for 20 min at room temperature. 1,3-Diisopropyldicarboimide (0.06 mmol) was added to the resulting suspension, which was allowed to stir overnight at room temperature. The solvent was drained, and the resulting resin was washed with DMF, methanol, and methylene chloride. The resin was resuspended in DMF (1 mL), to which was added N-Boc-diaminobutane (1 mL, 1M solution in DMF). The resulting mixture was allowed to stir overnight at room temperature. The solvents were drained, and the resulting resin was washed with DMF, methanol, and methylene chloride to provide resin 18.

Resin 18 was treated with methylene chloride (1 ml), thioanisole (0.2 ml), ethanedithiol (0.05 ul), and TFA (2 ml) for 6 hours at room temperature. After stirring, the resin beads were filtrated off, and the filtrate was dried under reduced pressure overnight to provide a crude product. HPLC purification using gradient elution (0.1% TFA/H$_2$O; 0.1% TFA/CH$_3$CN, 100; 0 to 0; 100) of the crude product provided 4 mg of Compound AU as a white solid: ESI/MS m/z 431 (M$^+$).

7.5 SYNTHESIS OF COMPOUNDS AA-AT, AV-DV, DX, AND DY

Compounds AA-AT, AV-DV, DX, and DY were synthesized according to the methods used for synthesizing Compounds AU and DW, described above, using appropriate monomers.

8. EXAMPLE: BINDING TO HIV TAR RNA

Binding of compounds of formula I and V to TAR RNA was measured by evaluating their inhibition of TAR-TAT complex formation in the presence of increasing levels of the compound to be tested. The compounds of formula I were tested in an in vitro assay; the compounds of formula V were tested in an in vivo assay.

The TAR RNA used corresponds to the minimal sequence required for TAT responsiveness in vivo. This 29-residue oligonucleotide has the sequence: 5'-GGCAGAUCUGAG CCUGGGAGCUCUCUGCC-3' (SEQ ID NO.: 1). TAR RNA was prepared by in vitro transcription. A "top strand" single-stranded DNA oligomer having the sequence 5'-TAATACGACTCACTATAG-3' (SEQ ID NO.: 2) was annealed to a "bottom strand" single-stranded DNA template having the following sequence: 3'-ATTATGCTAAGT GATATCCCGTCTAGACTCGGACCCTCGAGAGACGG-5' (SEQ ID NO.: 3), thereby generating a double-stranded region corresponding to a promoter sequence recognized by T7 RNA polymerase. Transcription was carried out in transcription buffer (40 mM Tris-HCl, pH 8.1, 1 mM spermidine, 0.01% Triton® X-100, 5 mM dithiothreitol, 4 mM each of ATP, GTP, CTP, and UTP at 37° C. for 4 to 5 hours. Reactions were performed in a volume of 0.02 ml containing 8 pmole of template (top strand annealed to bottom strand) and 40 to 60 units of T7 RNA polymerase. Transcription was terminated by adding an equal volume of loading buffer (9M urea, 1 mmol EDTA, 0.1M bromophenol blue in 1XTBE buffer; TBE is 45 mmol trisborate at pH 8). Product RNA was purified by electrophoresis through a denaturing 20% polyacrylamide gel containing 8M urea. RNA was extracted from the gel, precipitated, dissolved in dithylpyrocarbonate-treated water, and stored at −20° C. until used.

In vitro assay conditions: Compounds AA-DU were synthesized on TentaGel S—NH$_2$ (4.6 mmole). All Fmoc-amino acids were purchased from Bachem (Torrance, Calif.). 1-hydroxybenzotriazole (HOBT) and diisopropylcarbodiimide (DIPCDI) were obtained from Aldrich Chemical Co., Milwalkee, Wis. Piperidine and trifluoroacetic acid were purchased from Applied Biosystems Division, Perkin-Elmer. Compounds AA-DU were synthesized manually according to standard solid-phase peptide synthesis protocols. Coupling efficiencies of residues at each step were monitored by Kaiser test. Deprotection of trimer peptides was carried out in 10% water in trifluoroacetic acid (1 mL) for 16 hours at room temperature. After filtration of solvents, the resin was washed with water (1 mL×4), DMF (1 mL×4), dichloromethane (1 mL×4), and dried under reduced pressure. The compounds attached to the resin (10 beads) were placed in an Eppendorf tube and washed with TK buffer (200 mL×3). The beads were suspended in TK buffer (300 mL) and incubated with TAR RNA (1.95 mM) overnight at 4° C. The suspension was centrifuged and the supernatant containing unbound RNA was transferred to a cuvette for OD$_{260}$ measurements. The UV absorbance was measured by a Shimadzu UV-1601 spectrometer. Equilibrium concentrations of RNA were determined from these measurements. Given that the initial concentrations of ligand and RNA are known, and assuming simple bimolecular receptor/substrate binding, dissociation constant (K$_D$) was calculated from straightforward equations.

TAT peptide has the amino acid sequence: GRKKRRQRRR (SEQ ID NO.: 4) which corresponds to amino acids 48–57 of the intact protein.

In vivo assay conditions: HL3T1 cells, a HeLa cell line derivative containing an integrated HIV-1 LTR promoter and CAT reporter gene, were used. Cells were grown in 2 mL of Dulbecco's modified Eagle medium (DMEM) supplemented with 10% fetal calf serum in 60 mm dishes at 37° C. in 5%

CO in a tissue culture incubator. Cells were refreshed by 2 mL DMEM before transfection. Transfection was started by dropwise addition of 250 µL 2×HeBS (Hepes-buffered saline) and then keeping at room temperature for 10 minutes. Approximately 10 µg of plasmids (pSV2Tat and pAL) and increasing amounts of the Compounds DV, DW, DX or DY were transfected in the presence of $CaCl_2$ (final concentration 125 mM) and the cells were incubated for 4 hour at 37° C. in a tissue culture incubator. The medium was then discarded and the cells were subjected to glycerol (1.5 mL of 15%) shock for 45 seconds. Finally the cells were washed twice with PBS (5 mL) and were grown in 3 mL DMEM. The cells were harvested after 48 hour post-transfection with changing with fresh DMEM at 24 hours and lysed in reporter lysis buffer (Promega). Aliquots were used for CAT and luciferase assays. Both activities were normalized to protein concentration determined by using a modified Bradford assay (Bio-Rad).

The binding data obtained, which demonstrate that the compounds of the invention inhibit TAT-peptide TAR-RNA interaction, are summarized in Table I:

TABLE I

BINDING CONSTANTS

| Compound | Kd (nM) |
|---|---|
| AA | 639 |
| AB | 523 |
| AC | 215 |
| AD | 2079 |
| AE | 1111 |
| AF | 491 |
| AG | 403 |
| AH | 460 |
| AI | 603 |
| AJ | 4313 |
| AK | 1716 |
| AL | 2717 |
| AM | 183 |
| AN | 183 |
| AO | 120 |
| AP | 1494 |
| AQ | 2079 |
| AR | 376 |
| AS | 147 |
| AT | 165 |
| AU | 147 |
| AV | 325 |
| AW | 89 |
| AX | 165 |
| AY | 403 |
| AZ | 147 |
| BA | 460 |
| BB | 256 |
| BC | 183 |
| BD | 235 |
| BE | 678 |
| BF | 147 |
| BG | 431 |
| BH | 2527 |
| BI | 202 |
| BJ | 202 |
| BK | 930 |
| BL | 718 |
| BM | 403 |
| BN | 3151 |
| BO | 183 |
| BP | 2191 |
| BQ | 235 |
| BR | 5591 |
| BS | 639 |
| BT | 202 |
| BU | 1418 |
| BV | 403 |

TABLE I-continued

BINDING CONSTANTS

| Compound | Kd (nM) |
|---|---|
| BW | 678 |
| BX | 202 |
| BY | 183 |
| BZ | 130 |
| CA | 460 |
| CB | 603 |
| CC | 567 |
| CD | 567 |
| CE | 301 |
| CF | 567 |
| CG | 603 |
| CH | 865 |
| CI | 981 |
| CJ | 1256 |
| CK | 1111 |
| CL | 130 |
| CM | 491 |
| CN | 235 |
| CO | 147 |
| CP | 678 |
| CQ | 2353 |
| CR | 981 |
| CS | 491 |
| CT | 147 |
| CU | 718 |
| CV | 567 |
| CW | 3976 |
| CX | 256 |
| CY | 523 |
| CZ | 183 |
| DA | 301 |
| DB | 256 |
| DC | 5113 |
| DD | 567 |
| DE | 120 |
| DF | 31369 |
| DG | 235 |
| DH | 7689 |
| DI | 235 |
| DJ | 603 |
| DK | 1111 |
| DL | 678 |
| DM | 256 |
| DN | 678 |
| DO | 1035 |
| DP | 774 |
| DQ | 6136 |
| DR | 460 |
| DS | 3151 |
| DT | 215 |
| DU | 639 |
| DV | 500 |
| DW | 50 |
| DX | 500 |
| DY | 150 |

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

A number of references have been cited, the entire disclosures of which are incorporated herein by reference.

What is claimed is:

1. A compound of formula I:

and pharmaceutically acceptable salts thereof, wherein each Y is independently a radical having the structure of II, III, or IV:

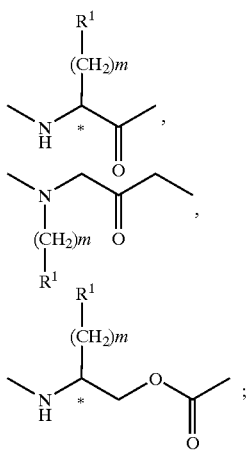

each $R_1$ is independently selected from the group consisting of —NH$_2$, —NHC(=NH)NH$_2$, and —CH$_2$C(=NH)NH$_2$;
each m is independently an integer ranging from 3 to 7;
each * is an (R) or (S) chiral center; and
with the proviso that at least one Y is a radical having the structure of IV.

2. The compound of claim 1, wherein at least two Y are independently a radical having the structure of IV.

3. The compound of claim 1, wherein each Y is independently a radical having the structure of IV.

4. The compound of claim 1, selected from the group consisting of:

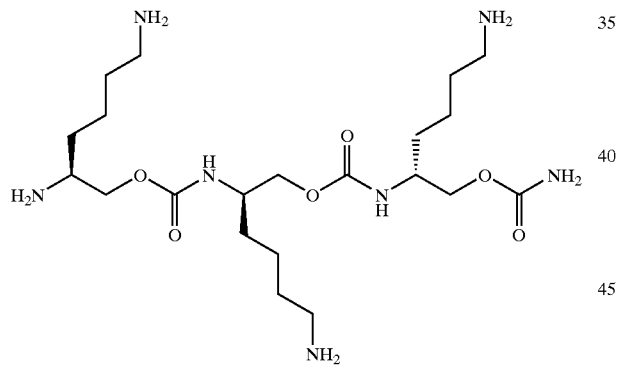

Carbamic acid 6-amino-2-[6-amino-2-(2,6-diamino-hexyloxycarbonylamino)-hexyloxycarbonylamino]-hexyl ester (Compound AA);

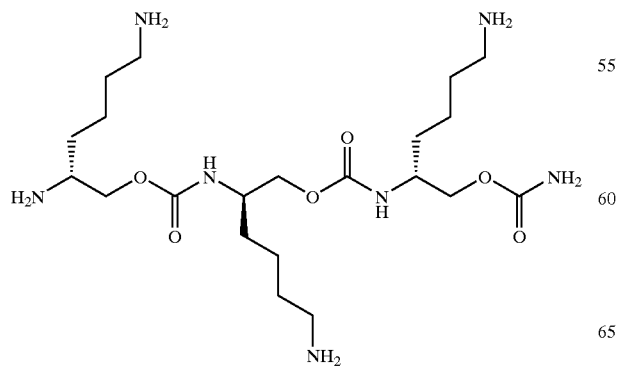

Carbamic acid 6-amino-2-[6-amino-2-(2,6-diamino-hexyloxycarbonylamino)-hexyloxycarbonylamino]-hexyl ester (Compound AB);

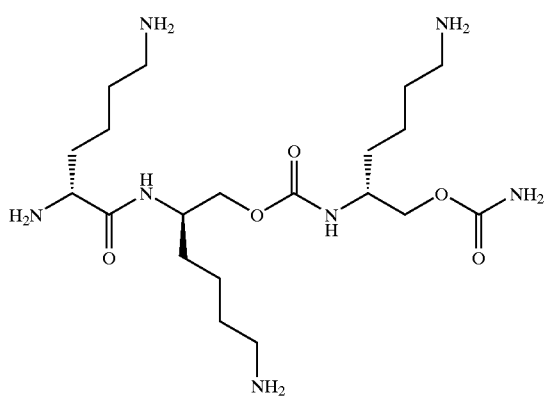

Carbamic acid 6-amino-2-[6-amino-2-(2,6-diamino-hexanoylamino)-hexyloxycarbonylamino]-hexyl ester (Compound AC);

Carbamic acid 6-amino-2-[6-amino-2-(2,6-diamino-hexanoylamino)-hexyloxycarbonylamino]-hexyl ester (Compound AD);

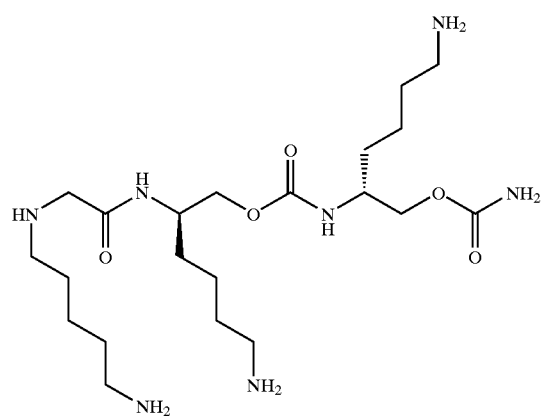

Carbamic acid 6-amino-2-{6-amino-2-[2-(5-amino-pentylamino)-acetylamino]-hexyloxycarbonylamino}-hexyl ester (Compound AE);

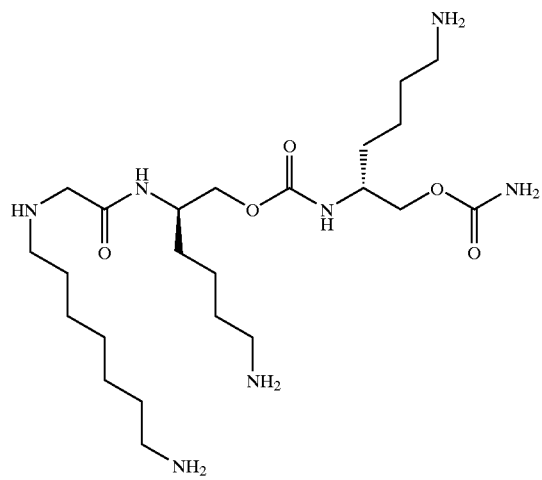

Carbamic acid 6-amino-2-{6-amino-2-[2-(7-amino-heptylamino)-acetylamino]-hexyloxycarbonylamino}-hexyl ester (Compound AF);

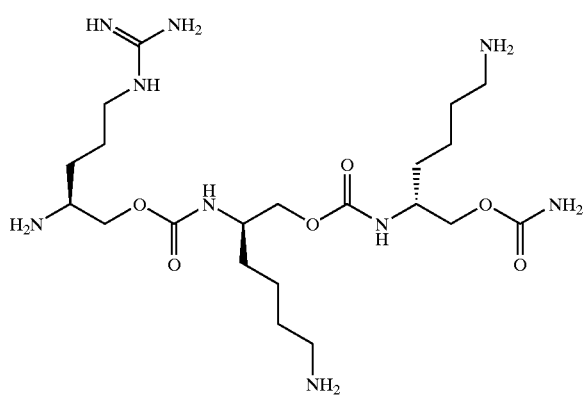

Carbamic acid 6-amino-2-{6-amino-2-[2-(4-amino-butylamino)-acetylamino]-hexyloxycarbonylamino}-hexyl ester (Compound AG);

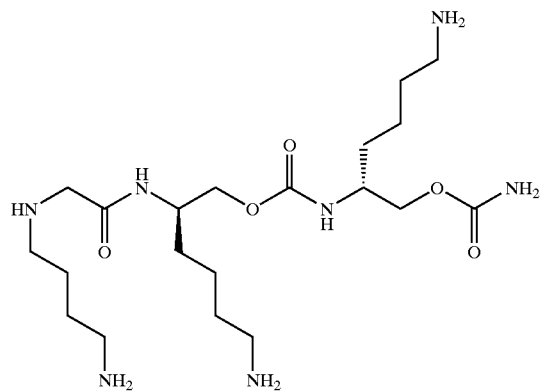

Carbamic acid 6-amino-2-[6-amino-2-(2-amino-5-guanidino-pentyloxycarbonylamino)-hexyloxycarbonylamino]-hexyl ester (Compound AH);

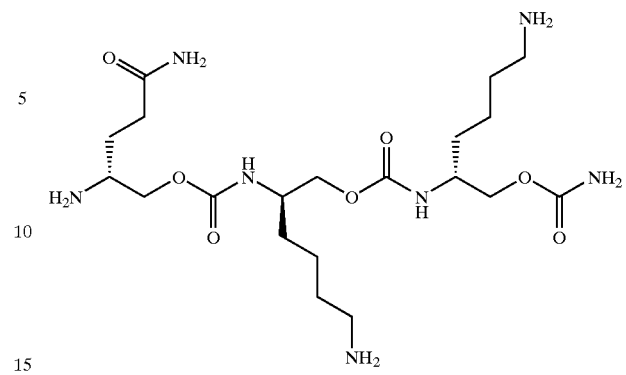

Carbamic acid 6-amino-2-[6-amino-2-(2-amino-4-carbamoyl-butoxycarbonylamino)-hexyloxycarbonylamino]-hexyl ester (Compound AI);

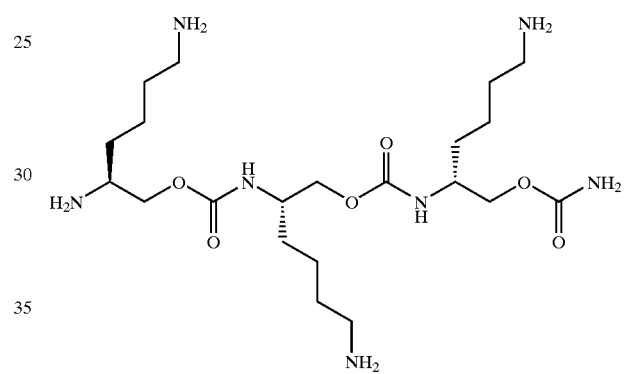

Carbamic acid 6-amino-2-[6-amino-2-(2,6-diamino-hexyloxycarbonylamino)-hexyloxycarbonylamino]-hexyl ester (Compound AJ);

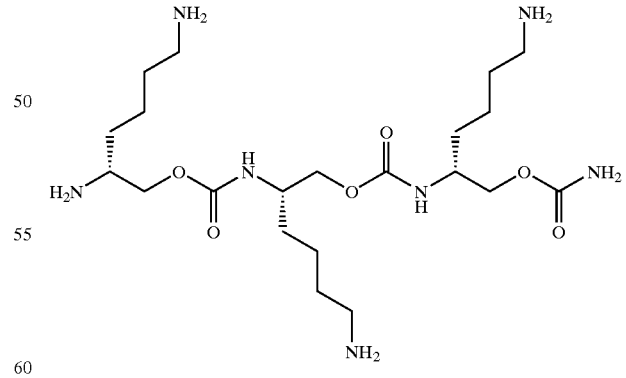

Carbamic acid 6-amino-2-[6-amino-2-(2,6-diamino-hexyloxycarbonylamino)-hexyloxycarbonylamino]-hexyl ester (Compound AK);

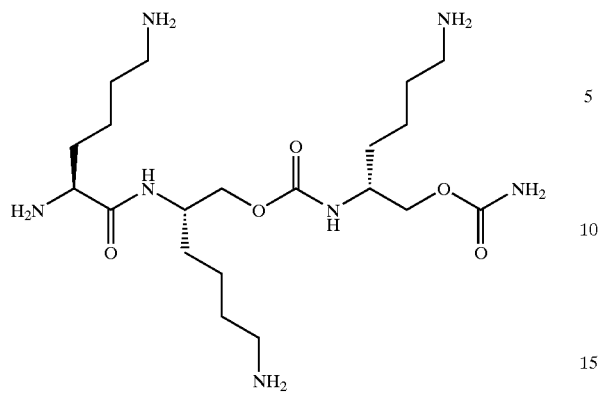

Carbamic acid 6-amino-2-[6-amino-2-(2,6-diamino-hexanoylamino)-hexyloxycarbonylamino]-hexyl ester (Compound AL);

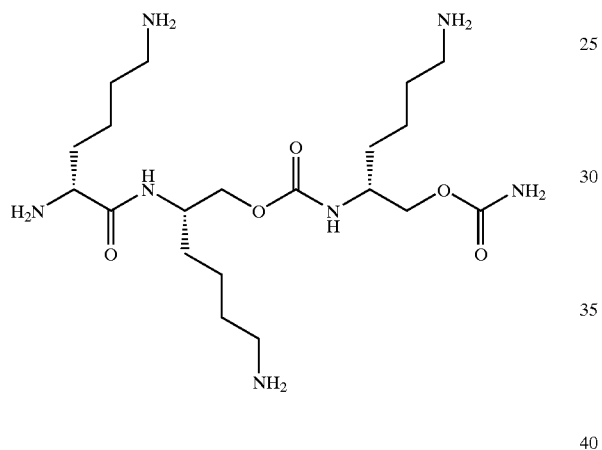

Carbamic acid 6-amino-2-[6-amino-2-(2,6-diamino-hexanoylamino)-hexyloxycarbonylamino]-hexyl ester (Compound AM);

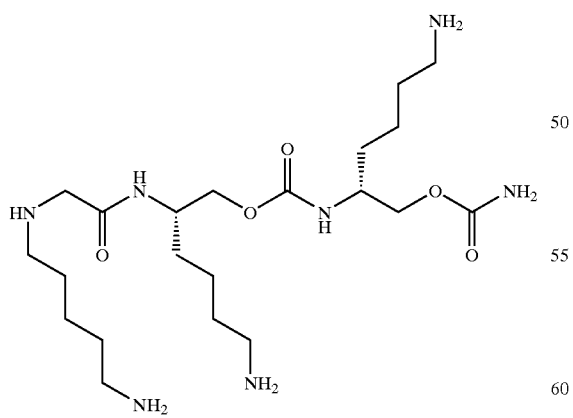

Carbamic acid 6-amino-2-{6-amino-2-[2-(5-amino-pentylamino)-acetylamino]-hexyloxycarbonylamino}-hexyl ester (Compound AN);

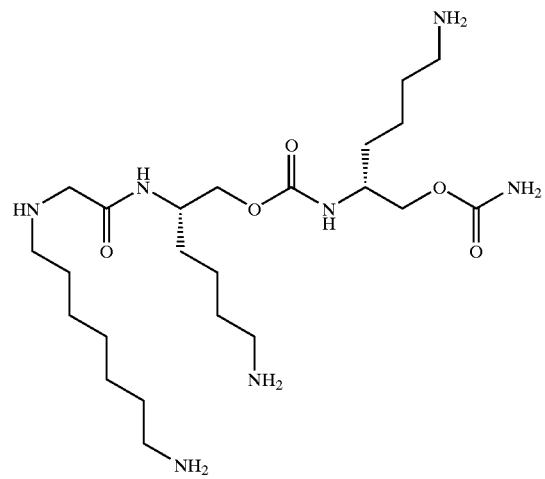

Carbamic acid 6-amino-2-{6-amino-2-[2-(7-amino-heptylamino)-acetylamino]-hexyloxycarbonylamino}-hexyl ester (Compound AO);

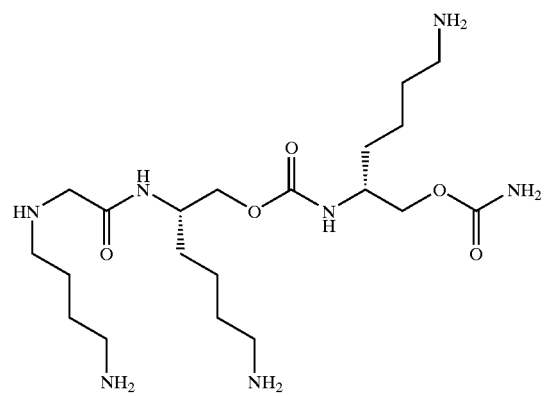

Carbamic acid 6-amino-2-{6-amino-2-[2-(4-amino-butylamino)-acetylamino]-hexyloxycarbonylamino}-hexyl ester (Compound AP);

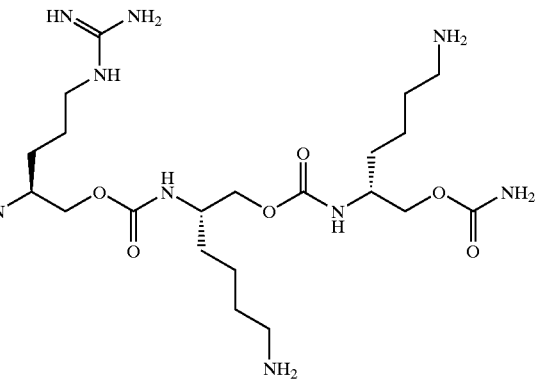

Carbamic acid 6-amino-2-[6-amino-2-(2-amino-5-guanidino-pentyloxycarbonylamino)-hexyloxycarbonylamino]-hexyl ester (Compound AQ);

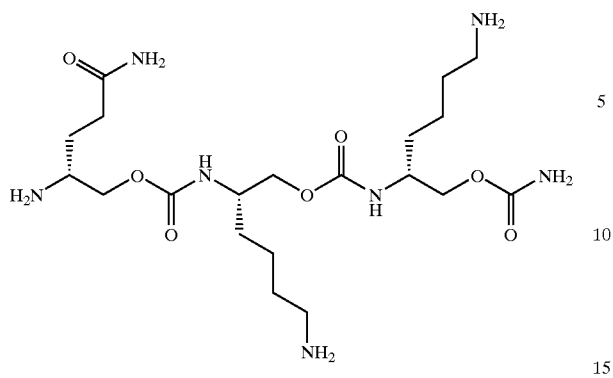

Carbamic acid 6-amino-2-[6-amino-2-(2-amino-4-carbamoyl-butoxycarbonylamino)-hexyloxycarbonylamino]-hexyl ester (Compound AR);

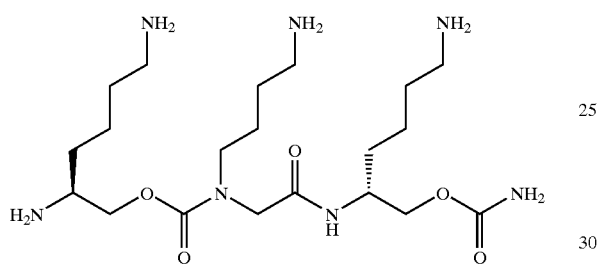

Carbamic acid 6-amino-2-{2-[(4-amino-butyl)-(2,6-diamino-hexyloxycarbonyl)-amino]-acetylamino}-hexyl ester (Compound AS);

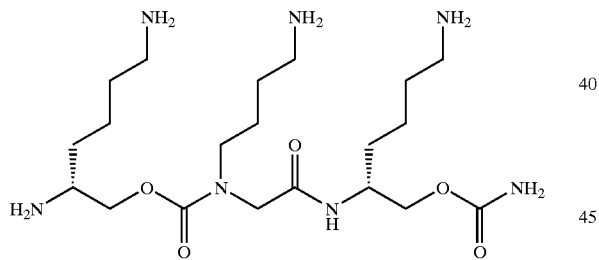

Carbamic acid 6-amino-2-{2-[(4-amino-butyl)-(2,6-diamino-hexyloxycarbonyl)-amino]-acetylamino}-hexyl ester (Compound AT);

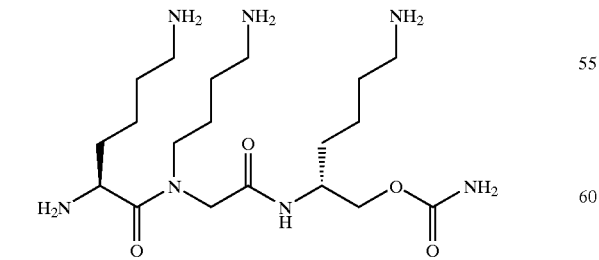

Carbamic acid 6-amino-2-{2-[(4-amino-butyl)-(2,6-diamino-hexanoyl)-amino]-acetylamino}-hexyl ester (Compound AU);

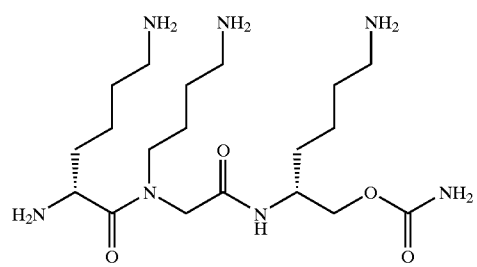

Carbamic acid 6-amino-2-{2-[(4-amino-butyl)-(2,6-diamino-hexanoyl)-amino]-acetylamino}-hexyl ester (Compound AV);

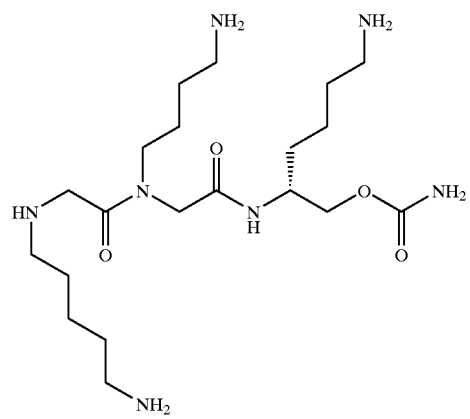

Carbamic acid 6-amino-2-(2-{(4-amino-butyl)-[2-(4-amino-butylamino)-acetyl]-amino}-acetylamino)-hexyl ester (Compound AW);

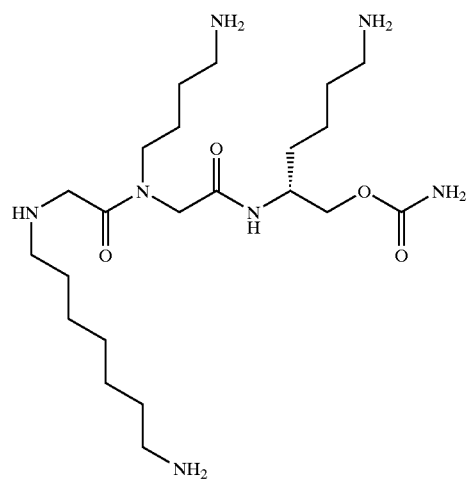

Carbamic acid 6-amino-2-(2-{(4-amino-butyl)-[2-(7-amino-heptylamino)-acetyl]-amino}-acetylamino)-hexyl ester (Compound AX);

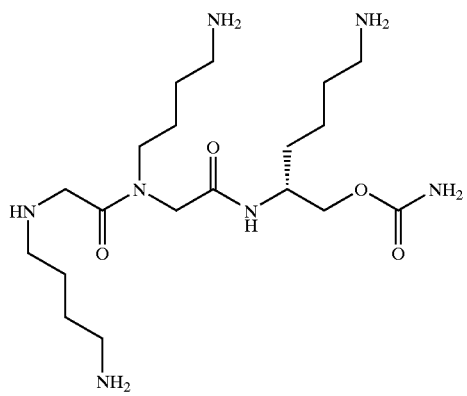

Carbamic acid 6-amino-2-(2-{(4-amino-butyl)-[2-(4-amino-butylamino)-acetyl]-amino}-acetylamino)-hexyl ester (Compound AY);

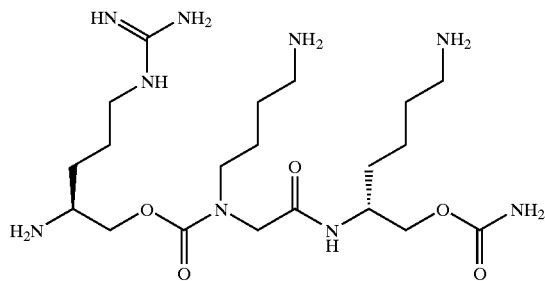

Carbamic acid 6-amino-2-{2-[(4-amino-butyl)-(2-amino-5-guanidino-pentyloxycarbonyl)-amino]-acetylamino}-hexyl ester (Compound AZ);

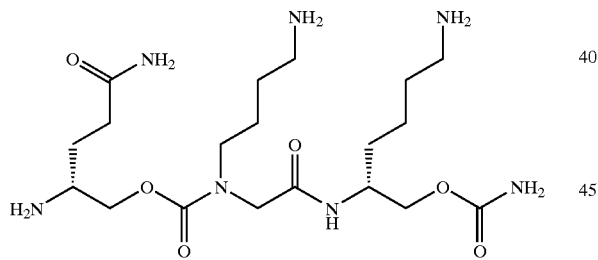

Carbamic acid 6-amino-2-{2-[(4-amino-butyl)-(2-amino-4-carbamoyl-butoxycarbonyl)-amino]-acetylamino}-hexyl ester (Compound BA);

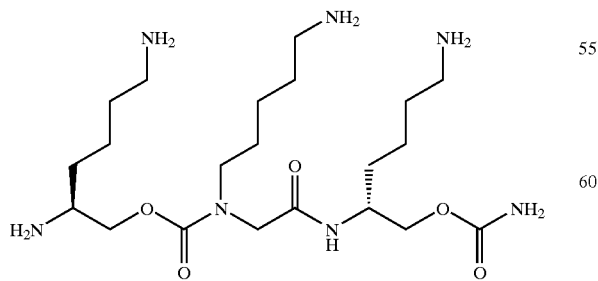

Carbamic acid 6-amino-2-{2-[(5-amino-pentyl)-(2,6-diamino-hexyloxycarbonyl)-amino]-acetylamino}-hexyl ester (Compound BB);

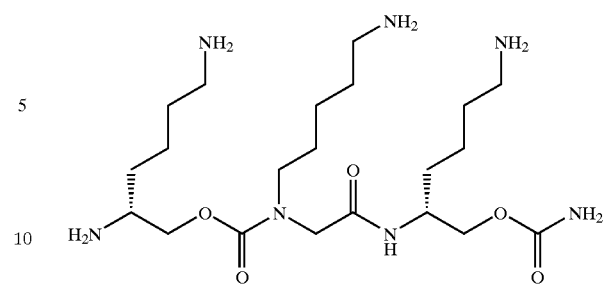

Carbamic acid 6-amino-2-{2-[(5-amino-pentyl)-(2,6-diamino-hexyloxycarbonyl)-amino]-acetylamino}-hexyl ester (Compound BC);

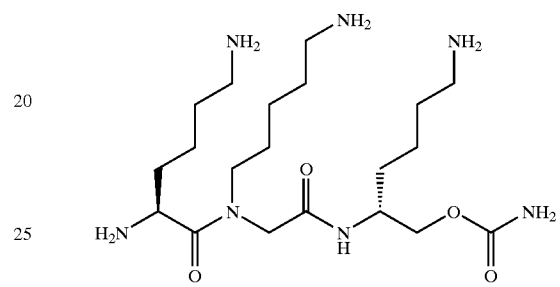

Carbamic acid 6-amino-2-{2-[(5-amino-pentyl)-(2,6-diaminohexanoyl)-amino]-acetylamino}-hexyl ester (Compound BD);

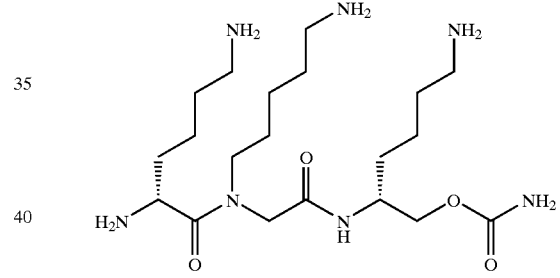

Carbamic acid 6-amino-2-{2-[(5-amino-pentyl)-(2,6-diamino-hexanoyl)-amino]-acetylamino}-hexyl ester (Compound BE);

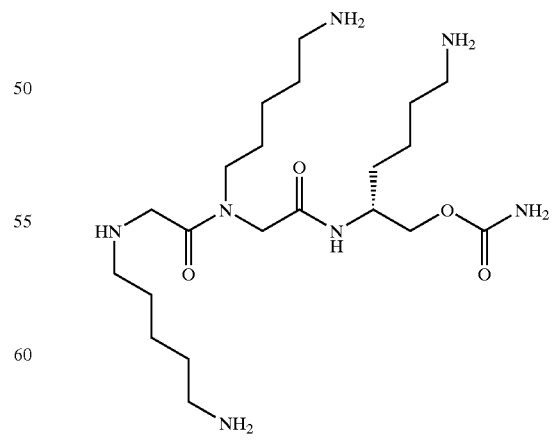

Carbamic acid 6-amino-2-(2-{(5-amino-pentyl)-[2-(5-amino-pentylamino)-acetyl]-amino}-acetylamino)-hexyl ester (Compound BF);

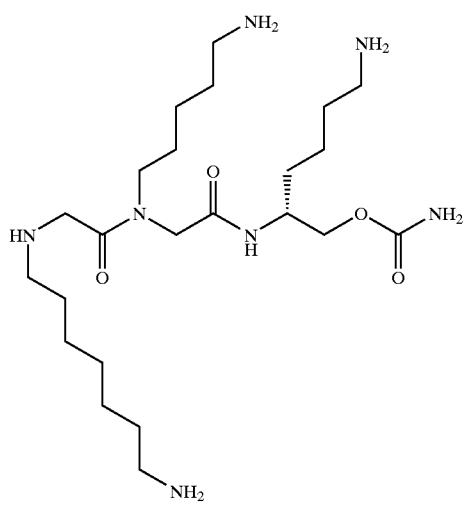

Carbamic acid 6-amino-2-{2-[[2-(7-amino-heptylamino)-acetyl]-(5-amino-pentyl)-amino]-acetylamino}-hexyl ester (Compound BG);

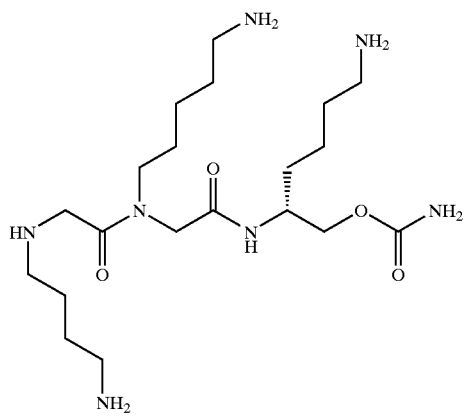

Carbamic acid 6-amino-2-{2-[[2-(4-amino-butylamino)-acetyl]-(5-amino-pentyl)-amino]-acetyl amino}-hexyl ester (Compound BH);

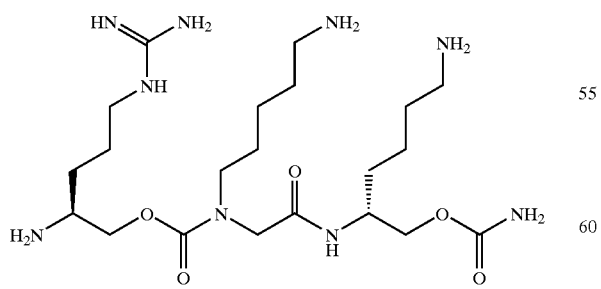

Carbamic acid 6-amino-2-{2-[(2-amino-5-guanidino-pentyloxycarbonyl)-(5-amino-pentyl)-amino]-acetylamino}-hexyl ester (Compound BI);

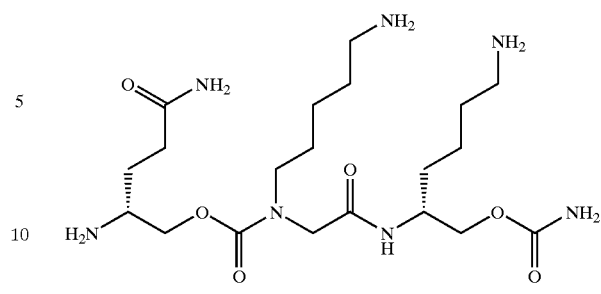

Carbamic acid 6-amino-2-{2-[(2-amino-4-carbamoyl-butoxycarbonyl)-(5-amino-pentyl)-amino]-acetylamino}-hexyl ester (Compound BJ);

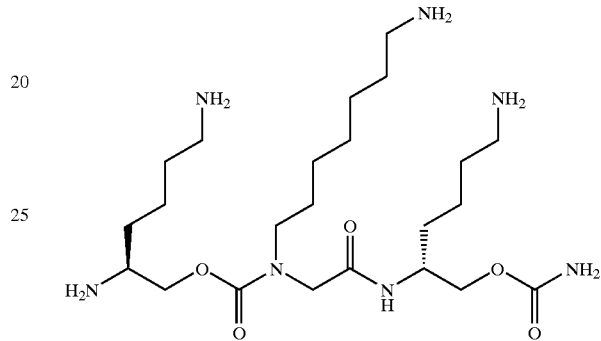

Carbamic acid 6-amino-2-{2-[(7-amino-heptyl)-(2,6-diamino-hexyloxycarbonyl)-amino]-acetylamino}-hexyl ester (Compound BK);

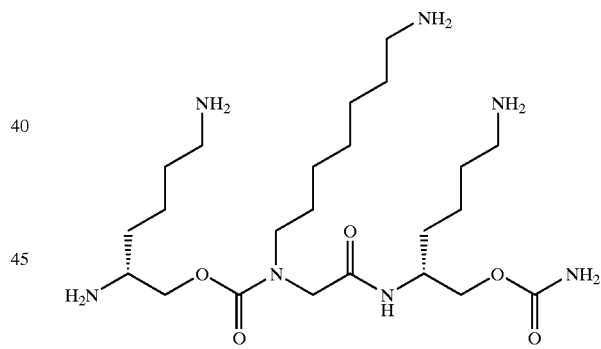

Carbamic acid 6-amino-2-{2-[(7-amino-heptyl)-(2,6-diamino-hexyloxycarbonyl)-amino]-acetylamino}-hexyl ester (Compound BL);

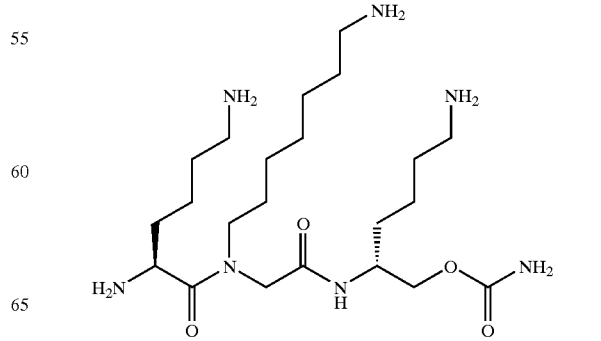

Carbamic acid 6-amino-2-{2-[(7-amino-heptyl)-(2,6-diamino-hexanoyl)-amino]-acetylamino}-hexyl ester (Compound BM);

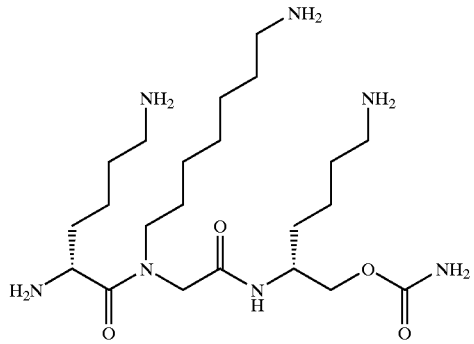

Carbamic acid 6-amino-2-{2-[(7-amino-heptyl)-(2,6-diamino-hexanoyl)-amino]-acetylamino}-hexyl ester (Compound BN);

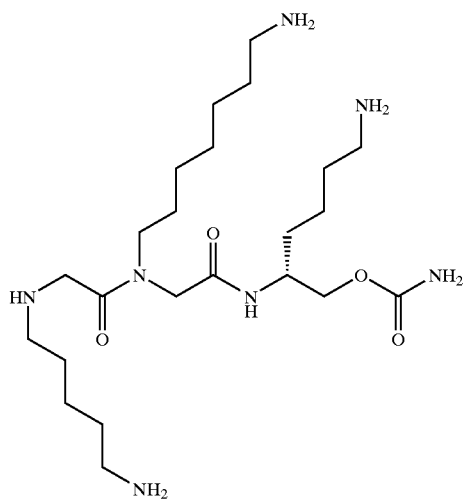

Carbamic acid 6-amino-2-(2-{(7-amino-heptyl)-[2-(5-amino-pentylamino)-acetyl]-amino}-acetylamino)-hexyl ester (Compound BO);

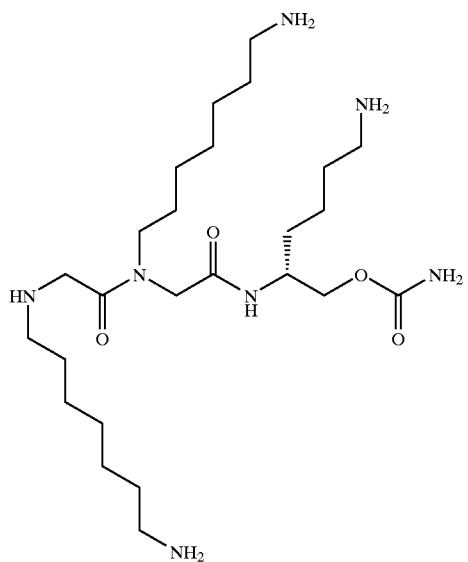

Carbamic acid 6-amino-2-(2-{(7-amino-heptyl)-[2-(7-amino-heptylamino)-acetyl]-amino}-acetylamino)-hexyl ester (Compound BP);

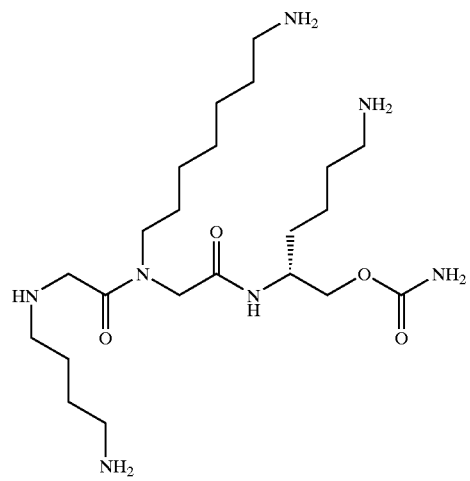

Carbamic acid 6-amino-2-{2-[[2-(4-amino-butylamino)-acetyl]-(7-amino-heptyl)-amino]-acetylamino}-hexyl ester (Compound BQ);

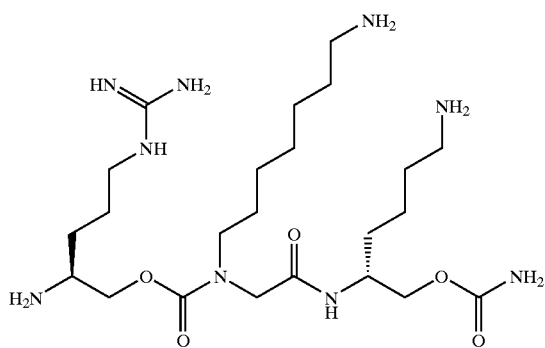

Carbamic acid 6-amino-2-{2-[(2-amino-5-guanidino-pentyloxycarbonyl)-(7-amino-heptyl)-amino]-acetylamino}-hexyl ester (Compound BR);

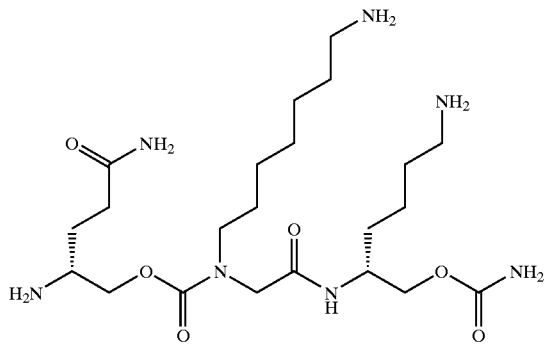

Carbamic acid 6-amino-2-{2-[(2-amino-4-carbamoyl-butoxycarbonyl)-(7-amino-heptyl)-amino]-acetylamino}-hexyl ester (Compound BS);

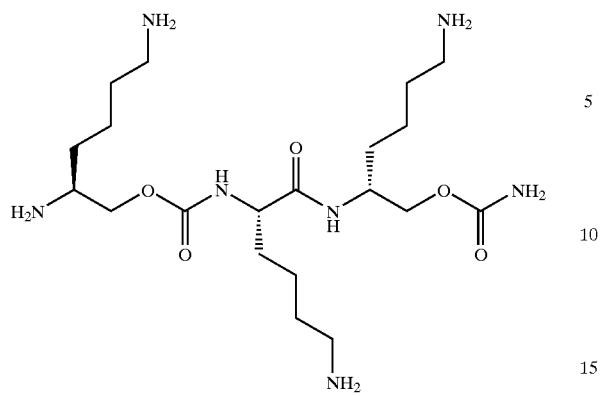

Carbamic acid 6-amino-2-[6-amino-2-(2,6-diamino-hexyloxycarbonylamino)-hexanoylamino]-hexyl ester (Compound BT);

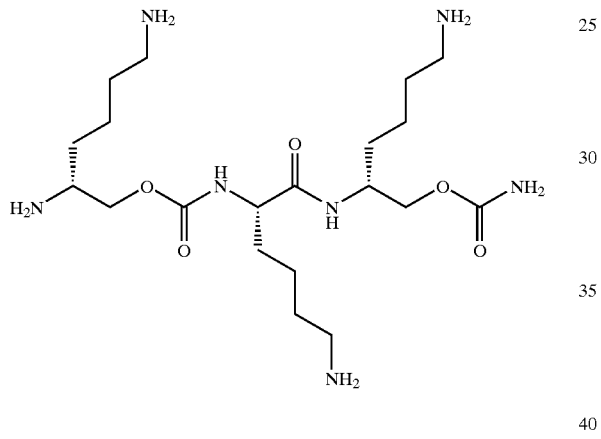

Carbamic acid 6-amino-2-[6-amino-2-(2,6-diaminohexyloxycarbonylamino)-hexanoylamino]-hexyl ester (Compound BU);

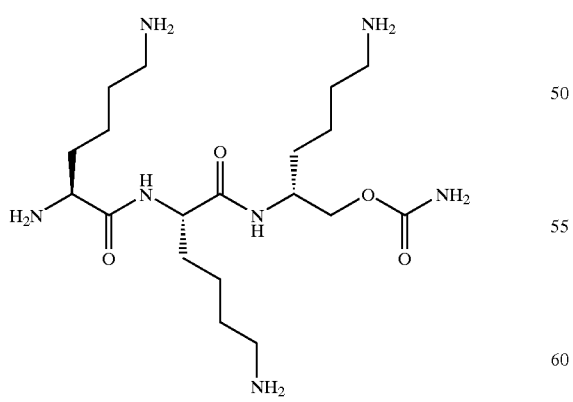

Carbamic acid 6-amino-2-[6-amino-2-(2,6-diaminohexanoylamino)-hexanoylamino]-hexyl ester (Compound BV);

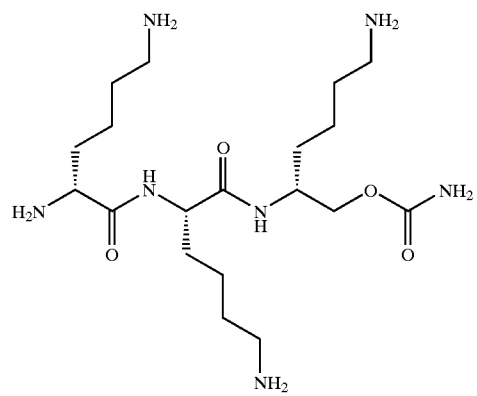

Carbamic acid 6-amino-2-[6-amino-2-(2,6-diaminohexanoylamino)-hexanoylamino]-hexyl ester (Compound BW);

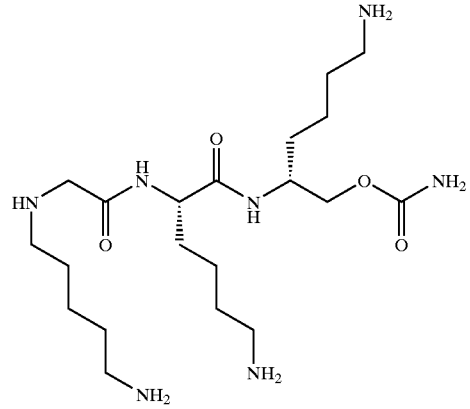

Carbamic acid 6-amino-2-{6-amino-2-[2-(5-aminopentylamino)-acetylamino]-hexanoylamino}-hexyl ester (Compound BX);

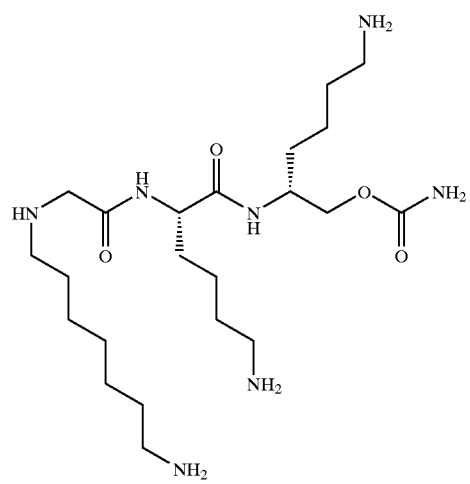

Carbamic acid 6-amino-2-{6-amino-2-[2-(7-aminoheptylamino)-acetylamino]-hexanoylamino}-hexyl ester (Compound BY);

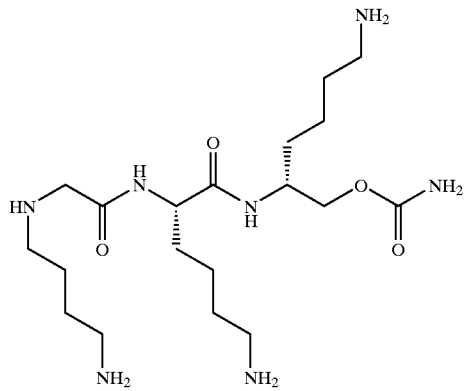

Carbamic acid 6-amino-2-{6-amino-2-[2-(4-amino-butylamino)-acetylamino]-hexanoylamino}-hexyl ester (Compound BZ);

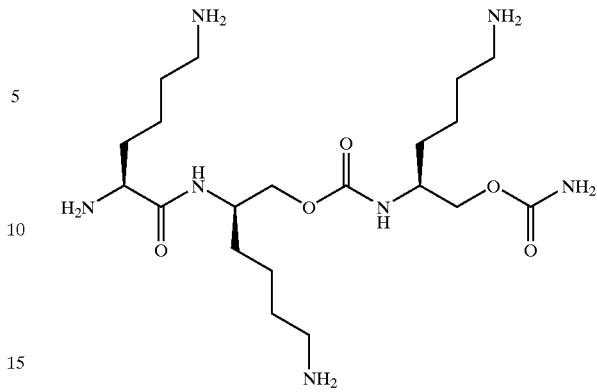

Carbamic acid 6-amino-2-[6-amino-2-(2,6-diamino-hexanoylamino)-hexyloxycarbonylamino]-hexyl ester (Compound CC);

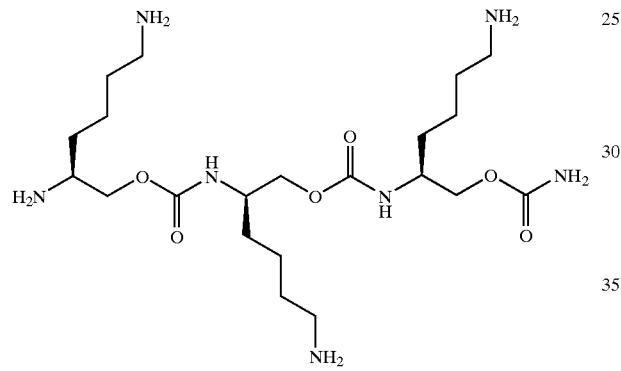

Carbamic acid 6-amino-2-[6-amino-2-(2,6-diamino-hexyloxycarbonylamino)-hexyloxycarbonylamino]-hexyl ester (Compound CA);

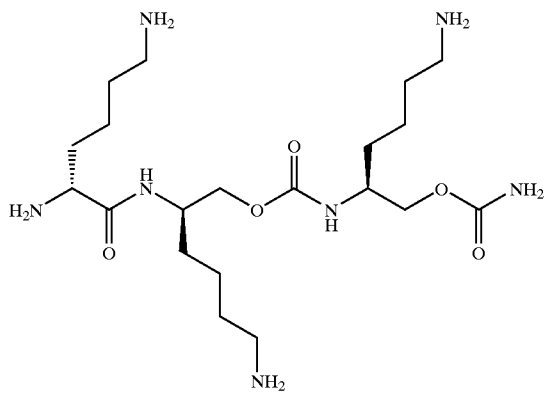

Carbamic acid 6-amino-2-[6-amino-2-(2,6-diamino-hexanoylamino)-hexyloxycarbonylamino]-hexyl ester (Compound CD);

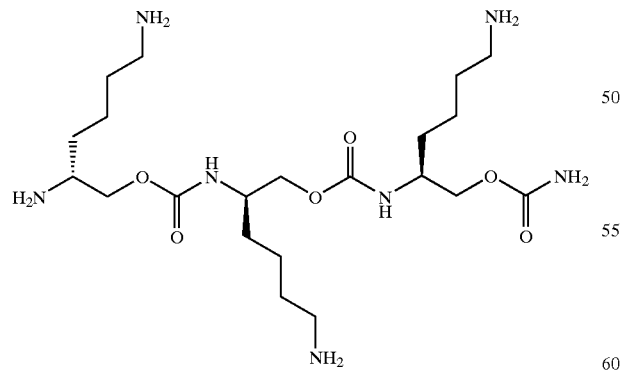

Carbamic acid 6-amino-2-[6-amino-2-(2,6-diamino-hexyloxycarbonylamino)-hexyloxycarbonylamino]-hexyl ester (Compound CB);

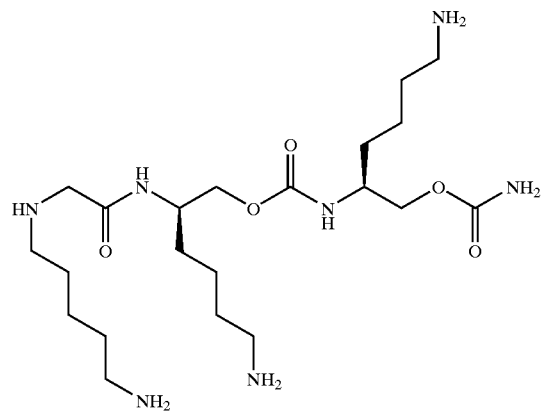

Carbamic acid 6-amino-2-{6-amino-2-[2-(5-amino-pentylamino)-acetylamino]-hexyloxycarbonylamino}-hexyl ester (Compound CE);

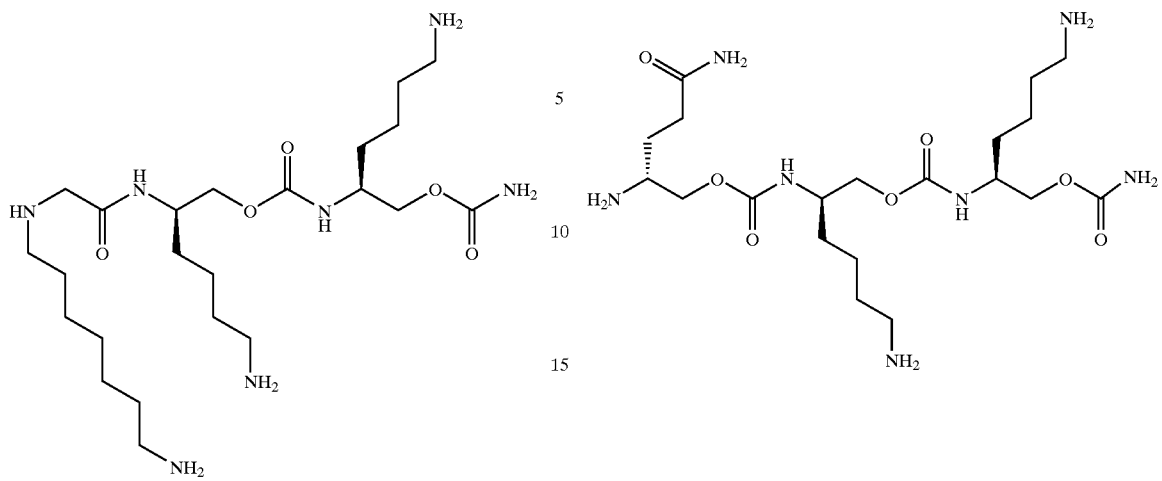

Carbamic acid 6-amino-2-{6-amino-2-[2-(7-amino-heptylamino)-acetylamino]-hexyloxycarbonylamino}-hexyl ester (Compound CF);

Carbamic acid 6-amino-2-[6-amino-2-(2-amino-5-guanidino-pentyloxycarbonylamino)-hexyloxycarbonylamino]-hexyl ester (Compound CI);

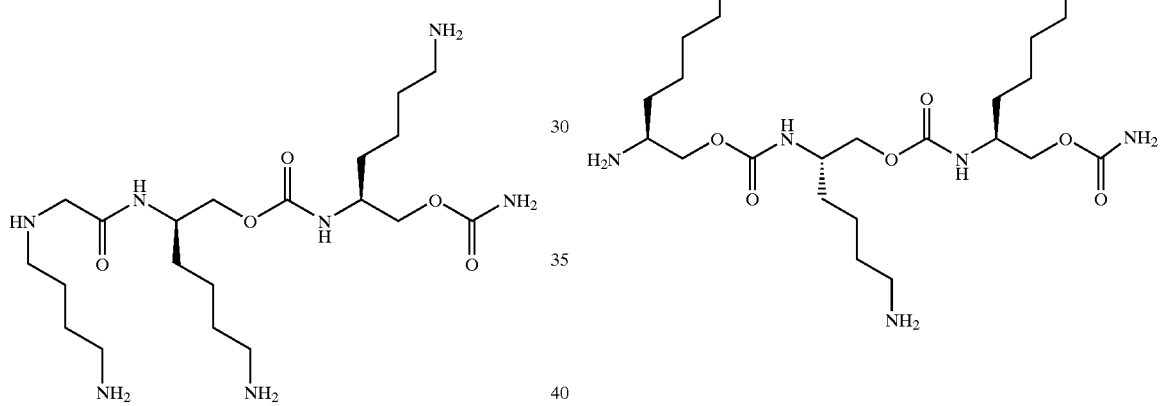

Carbamic acid 6-amino-2-{6-amino-2-[2-(4-amino-butylamino)-acetylamino]-hexyloxycarbonylamino}-hexyl ester (Compound CG);

Carbamic acid 6-amino-2-[6-amino-2-(2,6-diamino-hexyloxycarbonylamino)-hexyloxycarbonylamino]-hexyl ester (Compound CJ);

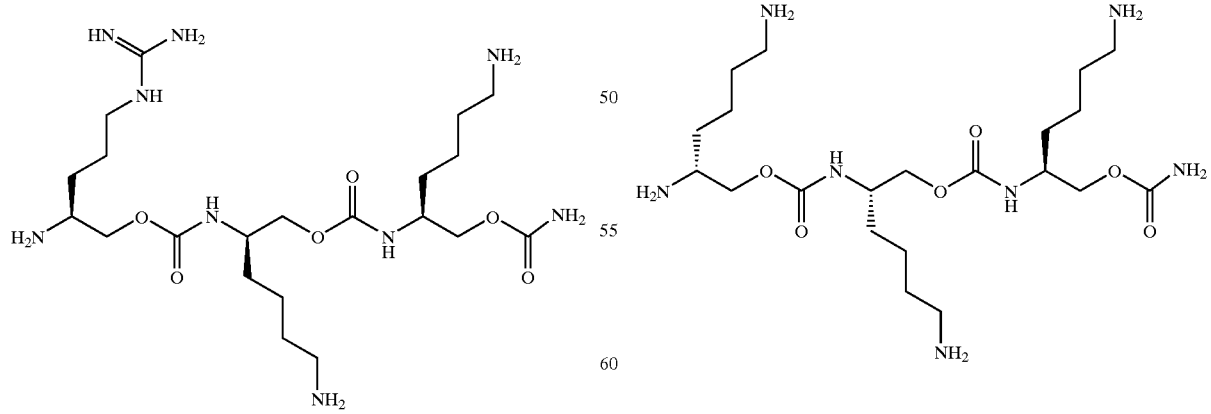

Carbamic acid 6-amino-2-[6-amino-2-(2-amino-5-guanidino-pentyloxycarbonylamino)-hexyloxycarbonylamino]-hexyl ester (Compound CH);

Carbamic acid 6-amino-2-[6-amino-2-(2,6-diamino-hexyloxycarbonylamino)-hexyloxycarbonylamino]-hexyl ester (Compound CK);

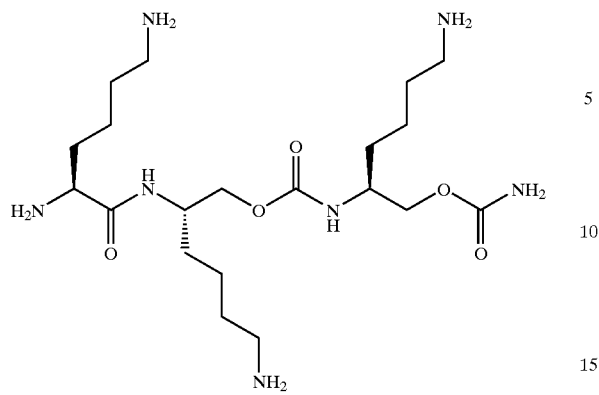

acid 6-amino-2-[6-amino-2-(2,6-diamino-hexanoylamino)-hexyloxy Carbamic carbonylamino]-hexyl ester (Compound CL);

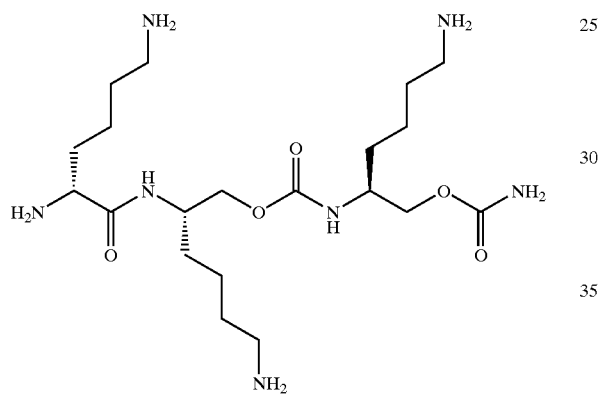

Carbamic acid 6-amino-2-[6-amino-2-(2,6-diamino-hexanoylamino)-hexyloxycarbonylamino]-hexyl ester (Compound CM);

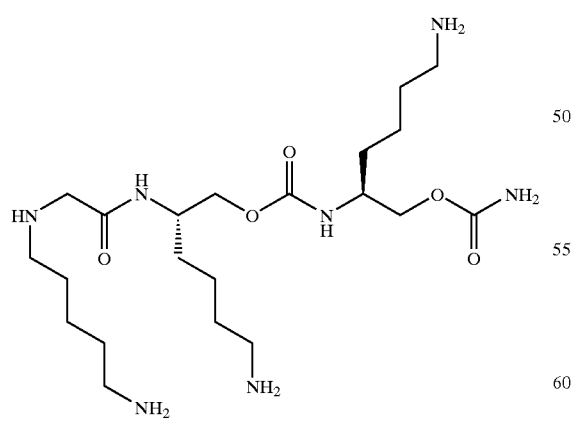

Carbamic acid 6-amino-2-{6-amino-2-[2-(5-amino-pentylamino)-acetylamino]-hexyloxycarbonylamino}-hexyl ester (Compound CN);

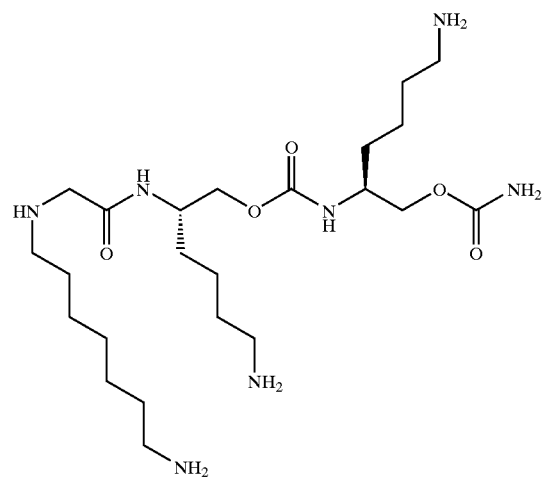

Carbamic acid 6-amino-2-{6-amino-2-[2-(7-amino-heptylamino)-acetylamino]-hexyloxycarbonylamino}-hexyl ester (Compound CO);

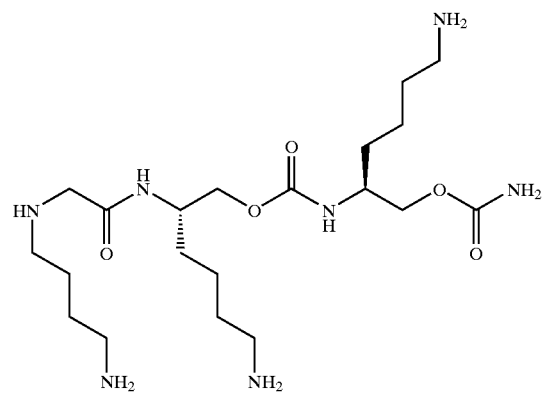

Carbamic acid 6-amino-2-{6-amino-2-[2-(4-amino-butylamino)-acetylamino]-hexyloxycarbonylamino}-hexyl ester (Compound CP);

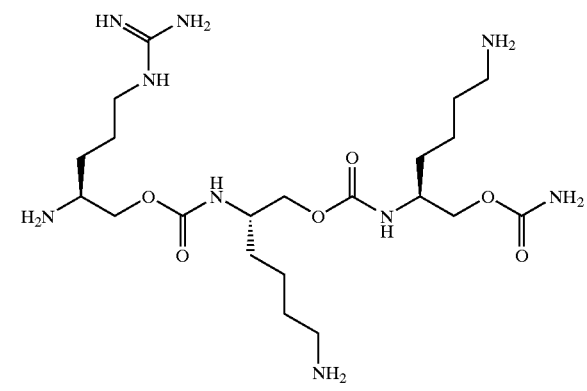

Carbamic acid 6-amino-2-[6-amino-2-(2-amino-5-guanidino-pentyloxycarbonylamino)-hexyloxycarbonylamino]-hexyl ester (Compound CQ);

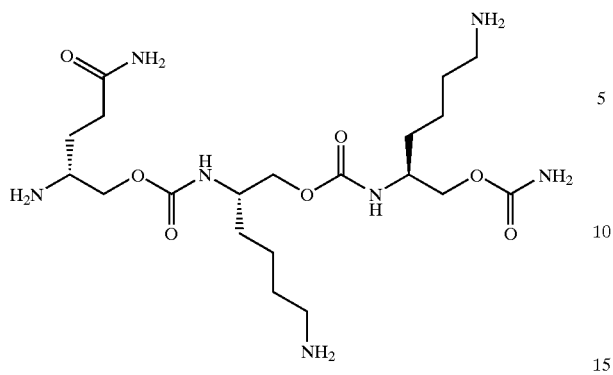

Carbamic acid 6-amino-2-[6-amino-2-(2-amino-4-carbamoyl-butoxycarbonylamino)-hexyloxycarbonylamino]-hexyl ester (Compound CR);

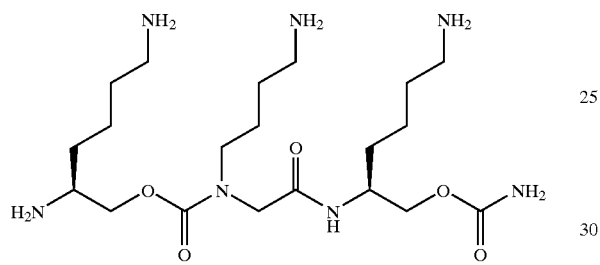

Carbamic acid 6-amino-2-{2-[(4-amino-butyl)-(2,6-diamino-hexyloxycarbonyl)-amino]-acetylamino}-hexyl ester (Compound CS);

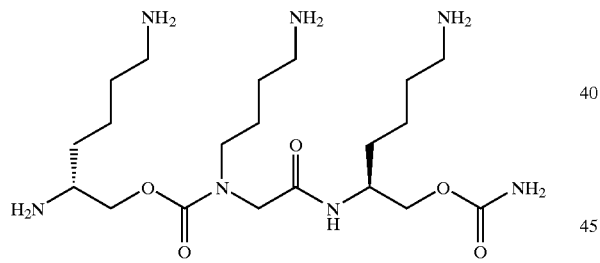

Carbamic acid 6-amino-2-{2-[(4-amino-butyl)-(2,6-diamino-hexyloxycarbonyl)-amino]-acetylamino}-hexyl ester (Compound CT);

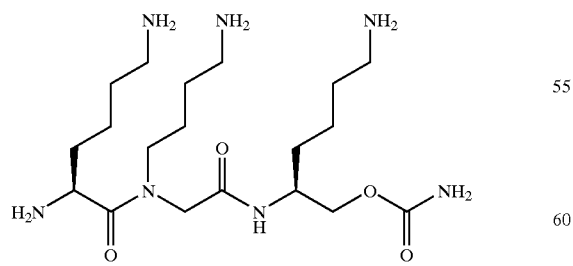

Carbamic acid 6-amino-2-{2-[(4-amino-butyl)-(2,6-diamino-hexanoyl)-amino]-acetylamino}-hexyl ester (Compound CU);

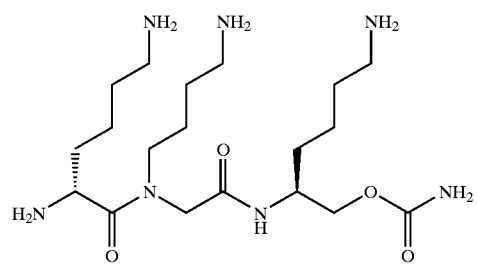

Carbamic acid 6-amino-2-{2-[(4-amino-butyl)-(2,6-diamino-hexanoyl)-amino]-acetylamino}-hexyl ester (Compound CV);

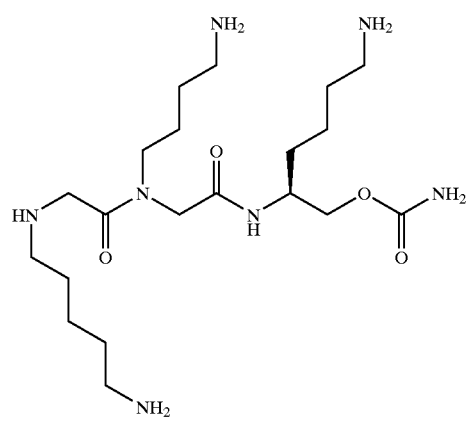

Carbamic acid 6-amino-2-(2-{(4-amino-butyl)-[2-(5-amino-pentylamino)-acetyl]-amino}-acetylamino)-hexyl ester (Compound CW);

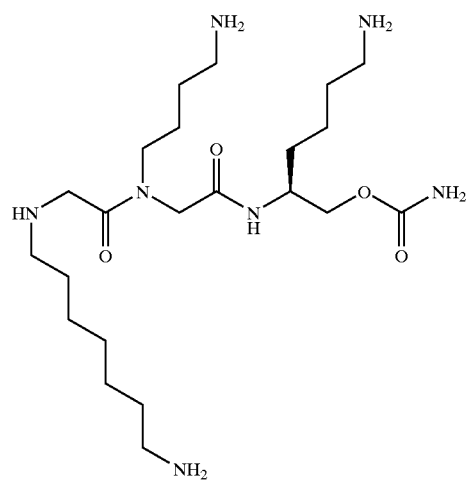

Carbamic acid 6-amino-2-(2-{(4-amino-butyl)-[2-(7-amino-heptylamino)-acetyl]-amino}-acetylamino)-hexyl ester (Compound CX);

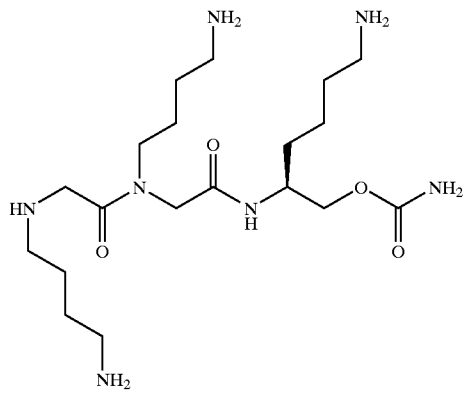

Carbamic acid 6-amino-2-(2-{(4-amino-butyl)-[2-(4-amino-butylamino)-acetyl]-amino}-acetylamino)-hexyl ester (Compound CY);

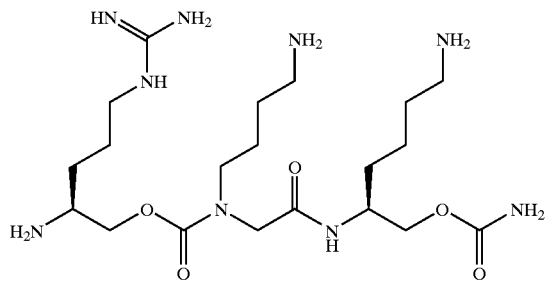

Carbamic acid 6-amino-2-{2-[(4-amino-butyl)-(2-amino-5-guanidino-pentyloxycarbonyl)-amino]-acetylamino}-hexyl ester (Compound CZ);

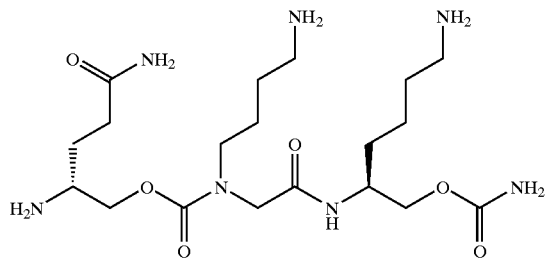

Carbamic acid 6-amino-2-{2-[(4-amino-butyl)-(2-amino-4-carbamoyl-butoxycarbonyl)-amino]-acetylamino}-hexyl ester (Compound DA);

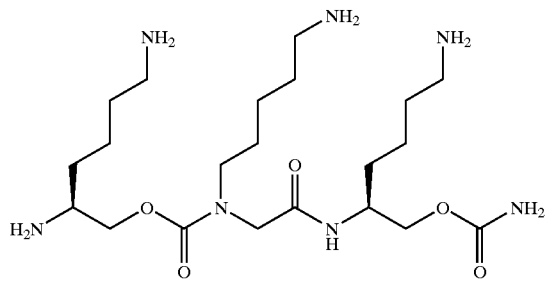

Carbamic acid 6-amino-2-{2-[(5-amino-pentyl)-(2,6-diamino-hexyloxycarbonyl)-amino]-acetylamino}-hexyl ester (Compound DB);

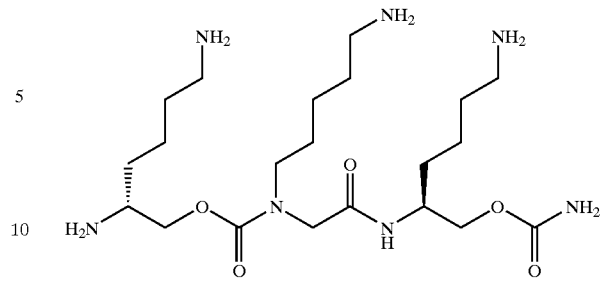

Carbamic acid 6-amino-2-{2-[(5-amino-pentyl)-(2,6-diamino-hexyloxycarbonyl)-amino]-acetylamino}-hexyl ester (Compound DC);

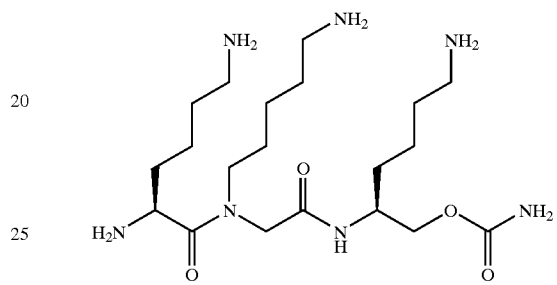

Carbamic acid 6-amino-2-{2-[(5-amino-pentyl)-(2,6-diamino-hexanoyl)-amino]-acetylamino}-hexyl ester (Compound DD);

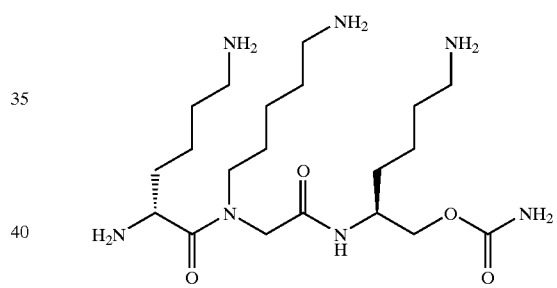

Carbamic acid 6-amino-2-{2-[(5-amino-pentyl)-(2,6-diamino-hexanoyl)-amino]-acetylamino}-hexyl ester (Compound DE);

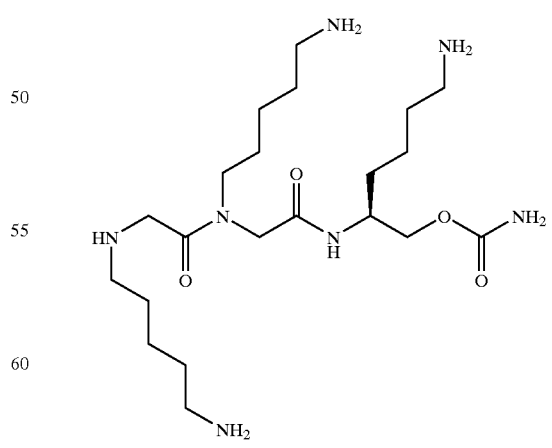

Carbamic acid 6-amino-2-(2-{(5-amino-pentyl)-[2-(5-amino-pentylamino)-acetyl]-amino}-acetylamino)-hexyl ester (Compound DF);

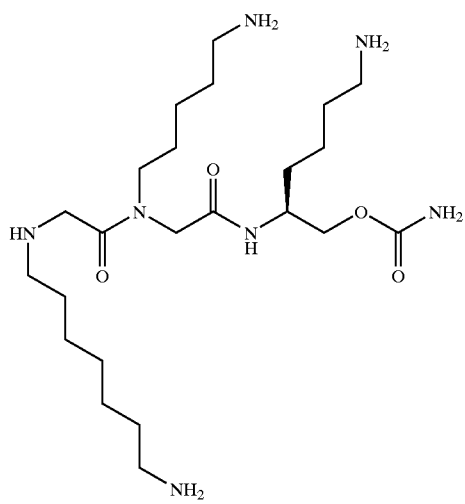

Carbamic acid 6-amino-2-{2-[[2-(7-amino-heptylamino)-acetyl]-(5-amino-pentyl)-amino]-acetylamino}-hexyl ester (Compound DG);

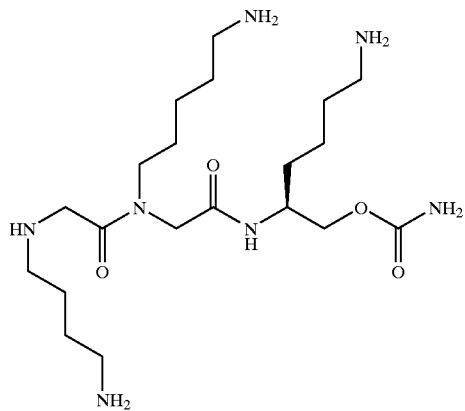

Carbamic acid 6-amino-2-{2-[[2-(4-amino-butylamino)-acetyl]-(5-amino-pentyl)-amino]-acetylamino}-hexyl ester (Compound DH);

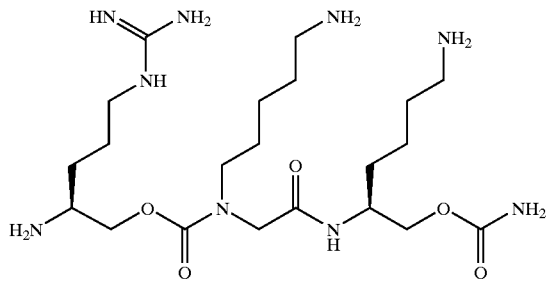

Carbamic acid 6-amino-2-{2-[(2-amino-5-guanidino-pentyloxycarbonyl)-(5-amino-pentyl)-amino]-acetylamino}-hexyl ester (Compound DI);

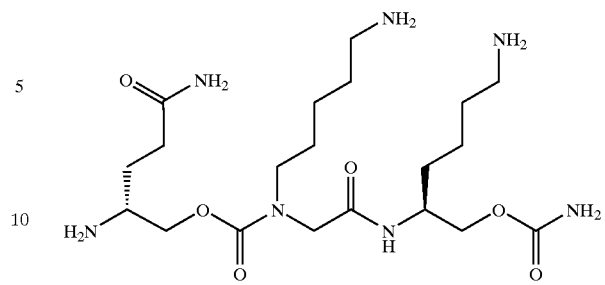

Carbamic acid 6-amino-2-{2-[(2-amino-4-carbamoyl-butoxycarbonyl)-(5-amino-pentyl)-amino]-acetylamino}-hexyl ester (Compound DJ);

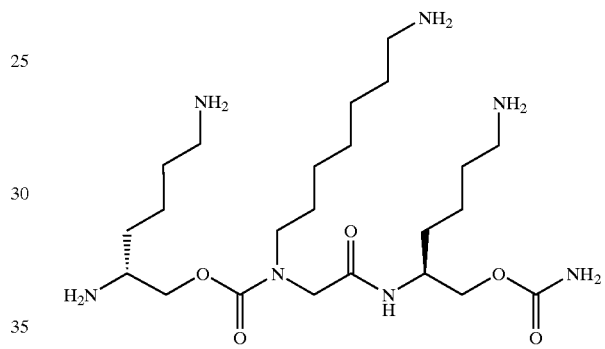

Carbamic acid 6-amino-2-{2-[(7-amino-heptyl)-(2,6-diamino-hexyloxycarbonyl)-amino]-acetylamino}-hexyl ester (Compound DK);

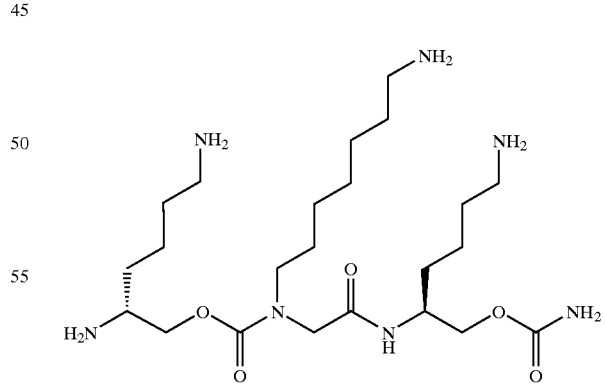

Carbamic acid 6-amino-2-{2-[(7-amino-heptyl)-(2,6-diamino-hexyloxycarbonyl)-amino]-acetylamino}-hexyl ester (Compound DL);

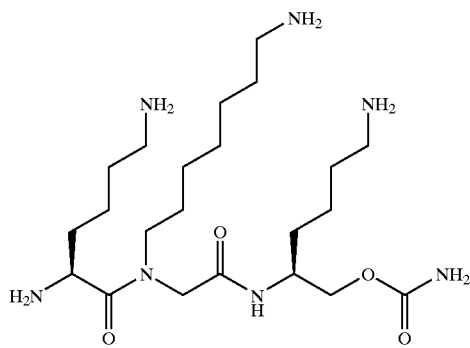

Carbamic acid 6-amino-2-{2-[(7-amino-heptyl)-(2,6-diamino-hexanoyl)-amino]-acetylamino}-hexyl ester (Compound DM);

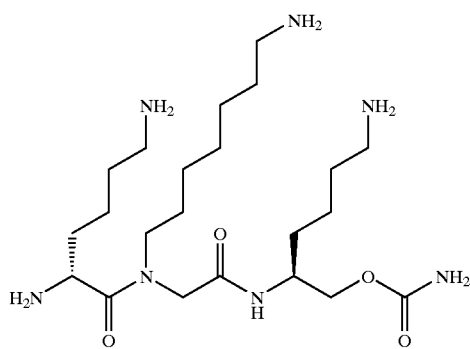

Carbamic acid 6-amino-2-{2-[(7-amino-heptyl)-(2,6-diamino-hexanoyl)-amino]-acetylamino}-hexyl ester (Compound DN);

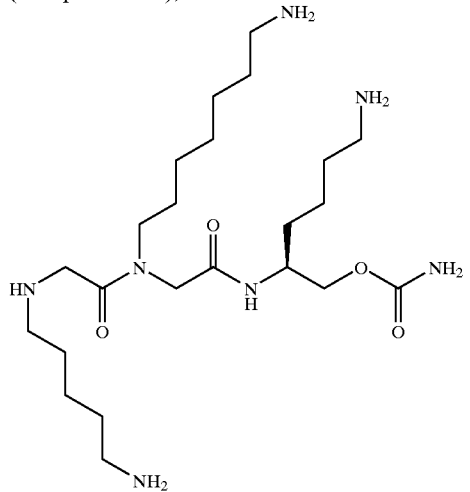

Carbamic acid 6-amino-2-(2-{(7-amino-heptyl)-[2-(5-amino-pentylamino)-acetyl]-amino}-acetylamino)-hexyl ester (Compound DO);

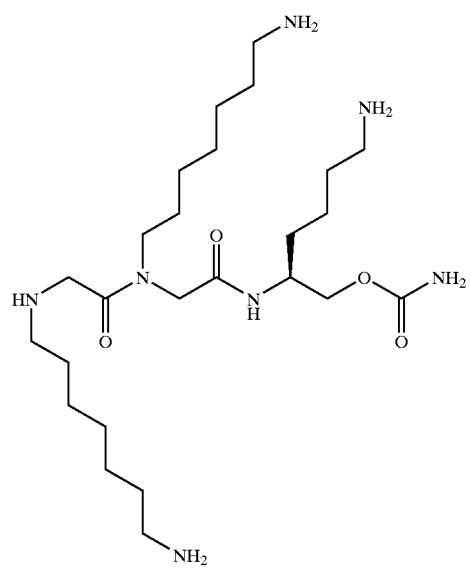

Carbamic acid 6-amino-2-(2-{(7-amino-heptyl)-[2-(7-amino-heptylamino)-acetyl]-amino}-acetylamino)-hexyl ester (Compound DP);

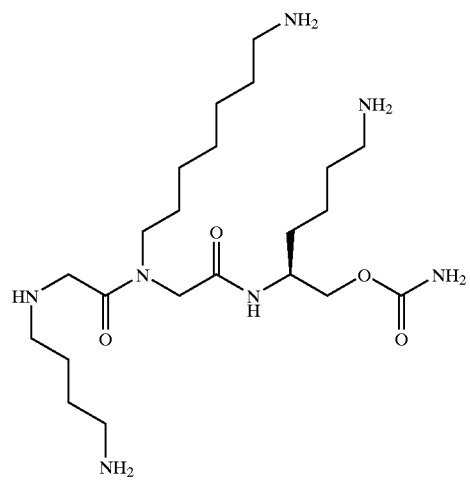

Carbamic acid 6-amino-2-{2-[[2-(4-amino-butylamino)-acetyl]-(7-amino-heptyl)-amino]-acetylamino}-hexyl ester (Compound DQ);

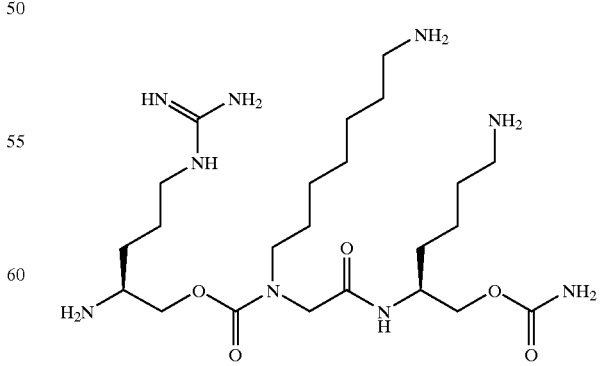

Carbamic acid 6-amino-2-{2-[(2-amino-5-guanidino-pentyloxycarbonyl)-(7-amino-heptyl)-amino]-acetylamino}-hexyl ester (Compound DR);

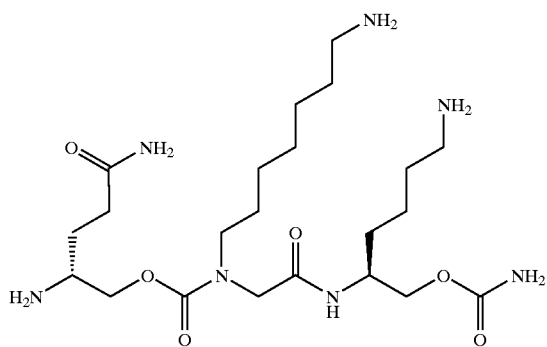

Carbamic acid 6-amino-2-{2-[(2-amino-4-carbamoyl-butoxycarbonyl)-(7-amino-heptyl)-amino]-acetylamino}-hexyl ester (Compound DS);

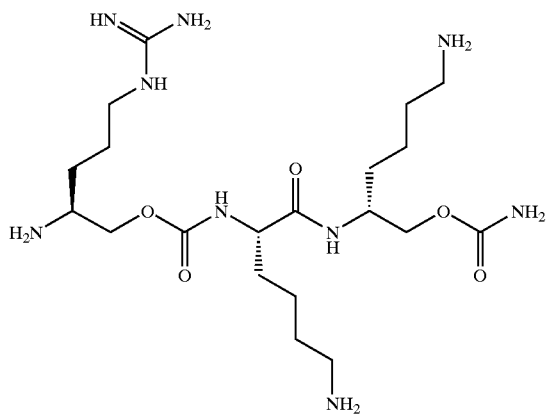

Carbamic acid 6-amino-2-[6-amino-2-(2-amino-5-guanidino-pentyloxycarbonylamino)-hexanoylamino]-hexyl ester (Compound DT);

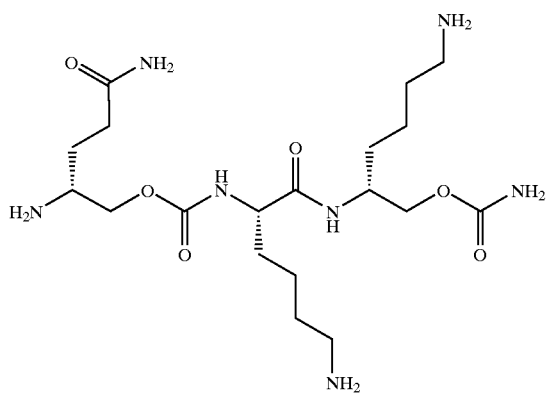

Carbamic acid 6-amino-2-[6-amino-2-(2-amino-4-carbamoyl-butoxycarbonylamino)-hexanoylamino]-hexyl ester (Compound DU); and pharmaceutically acceptable salts thereof.

5. A composition comprising a therapeutically effective amount of a compound of claim 1.

6. A composition comprising a therapeutically effective amount of a compound of claim 4.

7. The composition of claim 5, further comprising a pharmaceutically acceptable vehicle.

8. The composition of claim 5, further comprising an anticancer agent.

9. The composition of claim 5, further comprising an anti-inflammatory agent.

10. The composition of claim 5, further comprising an antiviral agent.

11. A method for treating cancer, inflammation, or a viral infection in a patient, comprising administering to a patient in need of such treatment or prevention a therapeutically effective amount of a compound of claim 1.

12. A method for treating cancer, inflammation, or a viral infection in a patient, comprising administering to a patient in need of such treatment or prevention a therapeutically effective amount of a compound of claim 4.

13. The method of claim 11, wherein the cancer is selected from the group consisting of leukemia, acute leukemia, acute lymphocytic leukemia, acute myelocytic leukemia, myeloblastic, promyelocytic, myelomonocytic, monocytic, erythroleukemia, chronic leukemia, chronic myelocytic, (granulocytic) leukemia, chronic lymphocytic leukemia, Polycythemia vera, lymphoma, Hodgkin's disease, non-Hodgkin's disease, Multiple myeloma, Waldenström's macroglobulinemia, Heavy chain disease, solid tumors, sarcomas and carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, and neuroblastomaretinoblastoma.

14. The method of claim 11, wherein the inflammation is selected from the group consisting of eczema, inflammatory bowel disease, rheumatoid arthritis, asthma, psoriasis, ischemia/reperfusion injury, ulcerative colitis and acute respiratory distress syndrome.

15. The method of claim 11, wherein the viral infection is selected from the group consisting of infections caused by hepatitis B, hepatitis C, rotavirus, human immunodeficiency virus type I (HIV-I), human immunodeficiency virus type II (HIV-II), human T-cell lymphotropic virus type I (HTLV-I), human T-cell lymphotropic virus type II (HTLV-II), AIDS, DNA viruses such as hepatitis type B and hepatitis type C virus; parvoviruses, such as adeno-associated virus and cytomegalovirus; papovaviruses such as papilloma virus, polyoma viruses, and SV40; adenoviruses; herpes viruses such as herpes simplex type I (HSV-I), herpes simplex type II (HSV-II), and Epstein-Barr virus; poxviruses, such as variola (smallpox) and vaccinia virus; and RNA viruses, such as human immunodeficiency virus type I (HIV-I), human immunodeficiency virus type II (HIV-II), human T-cell lymphotropic virus type I (HTLV-I), human T-cell lymphotropic virus type II (HTLV-II), influenza virus, measles virus, rabies virus, Sendai virus, picornaviruses such as poliomyelitis virus, coxsackieviruses, rhinoviruses, reoviruses, togaviruses such as rubella virus (German measles) and Semliki forest virus, arboviruses, and hepatitis type A virus.

* * * * *